US009212352B2

(12) United States Patent
Martin et al.

(10) Patent No.: US 9,212,352 B2
(45) Date of Patent: Dec. 15, 2015

(54) POLYPEPTIDES HAVING NUCLEIC ACID BINDING ACTIVITY

(75) Inventors: Patrick K. Martin, Redwood City, CA (US); David A. Simpson, Redwood City, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

(21) Appl. No.: 13/619,099

(22) Filed: Sep. 14, 2012

(65) Prior Publication Data

US 2013/0164817 A1 Jun. 27, 2013

Related U.S. Application Data

(63) Continuation of application No. 11/327,195, filed on Jan. 6, 2006, now Pat. No. 8,349,600.

(60) Provisional application No. 60/641,987, filed on Jan. 6, 2005.

(51) Int. Cl.
*C12N 9/12* (2006.01)
*C07K 14/00* (2006.01)
*C12N 9/96* (2006.01)
*C07K 14/195* (2006.01)
*C12Q 1/68* (2006.01)

(52) U.S. Cl.
CPC .............. *C12N 9/1252* (2013.01); *C07K 14/00* (2013.01); *C07K 14/195* (2013.01); *C12N 9/96* (2013.01); *C12Q 1/6832* (2013.01); *C07K 2319/80* (2013.01)

(58) Field of Classification Search
USPC .......................................... 435/194; 530/350
See application file for complete search history.

(56) References Cited

U.S. PATENT DOCUMENTS

| 6,627,424 | B1 | 9/2003 | Wang |
| 8,349,600 | B2 | 1/2013 | Martin et al. |
| 2003/0228616 | A1 | 12/2003 | Arezi et al. |

FOREIGN PATENT DOCUMENTS

| EP | 1833969 | 12/2010 |
| WO | 03/046149 | 6/2003 |
| WO | 2004/042086 | 5/2004 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*

Fitz-Gibbon, "Genome Sequence of the Hypertherophilic Crenarchaeon Pyrobaculum Aerophilum", Genbank Accession No. AAL62754, 2002, 1 page.
Fitz-Gibbon, "Genome Sequence of the Hypertherophilic Crenarchaeon Pyrobaculum Aerophilum", Genbank Accession No. AE009441, 2002, 1 page.
Fitz-Gibbon, S et al., "Genome Sequence of the Hypertherophilic Crenarchaeon Pyrobaculum Aerophilum", Genbank Accession No. AAL64739, 2002, 1 page.
Fitz-Gibbon, S et al., "Genome Sequence of the Hypertherophilic Crenarchaeon Pyrobaculum Aerophilum", *PNAS*, vol. 99, No. 2, Jan. 22, 2002, 984-989.
Guagliardi, A et al., "Annealing of Complementary DNA Strands Above the Melting Point of the Duplex Promoted by an Archael Protein", *Journal of Molecular Biology*, vol. 267, No. 4, London, Great Britain, Apr. 11, 1997, 841-848.
Hardy, C. et al., "Biochemical characterization of DNA-binding proteins from Pyrobaculum aerophilum and Aeropyrum pernix", *Extremophiles: Life Under Extreme Conditions*, vol. 12, No. 2, Mar. 2008, 235-246.
PCT/US2006/000191; Invitation to Pay Additional Fees Including Annex to Form PCTG/ISA/2006, Communication relating to the Results of the Partial International Search mailed Sep. 26, 2006, 6 pages.
PCT/US2006/000191; Notification Concerning Transmittal of International Preliminary Report on Patentability mailed Jul. 19, 2007, 16 pages.
PCT/US2006/000292; Invitation to Pay Additional Fees Including Annex to Form PCTG/ISA/2006, Communication relating to the Results of the Partial International Search mailed Sep. 12, 2006, 6 pages.
PCT/US2006/000292; Notification Concerning Transmittal of International Preliminary Report on Patentability mailed Jul. 19, 2007, 11 pages.
PCT/US2006/000292; Notification of Transmittal of the International Search Report and the Written Opinion of the International Searching Authority, or the Declaration mailed Jan. 18, 2007, 20 pages.
Promega Corporation, "PCR Master Mix", Product Sheet, Part No. 9PIM750, USA, Apr. 2004, 2 pages.
Saiki, et al., "Enzymatic Amplicalion of β-Globin Genomic Sequences and Reslriction Site Analvsis for Diagnosis of Sickle Cell Anemia", *Science*, vol. 230, No. 4732, Dec. 20, 1985, 1350-1354.

\* cited by examiner

*Primary Examiner* — Richard Hutson

(57) ABSTRACT

Polynucleotides having nucleic acid binding activity are provided. Methods of stabilizing a nucleic acid duplex are provided. Methods of promoting the annealing of complementary nucleic acid strands are provided. Methods of increasing the processivity of a DNA polymerase are provided. Methods of enhancing the activity of a nucleic acid modification enzyme are provided. Fusion proteins are provided. Methods of using fusion proteins are provided. Kits are provided.

22 Claims, No Drawings

POLYPEPTIDES HAVING NUCLEIC ACID BINDING ACTIVITY

This application is a continuation application of U.S. patent application Ser. No. 11/327,195, filed Jan. 6, 2006 which claims the benefit of priority to U.S. Provisional Application No. 60/641,987, filed Jan. 6, 2005.

I. FIELD

Polypeptides having nucleic acid binding activity are provided. Methods of using polypeptides having nucleic acid binding activity are provided. Fusion proteins and methods of using fusion proteins are provided.

II. INTRODUCTION

Polypeptides with nucleic acid binding activity are present in lower organisms, such as archaea, and higher organisms, such as eukaryotes. See, e.g., Pereira et al. (1997) *Proc. Nat'l Acad. Sci. USA* 94:12633-12637; and Motz et at. (2002) *J. Biol. Chem.* 277: 16179-16188. Polypeptides with nucleic acid binding activity have various functions. For example, certain polypeptides with nucleic acid binding activity, such as histones and histone-like proteins, are involved in the packaging of chromatin into higher order structures. See, e.g., Pereira et al. (1997) *Proc. Nat'l Acad. Sci. USA* 94:12633: 12637. Certain other polypeptides with nucleic acid binding activity may play a role as processivity factors in DNA replication. See, e.g., Motz et al. (2002) *J. Biol. Chem.* 277: 16179-16188.

III. SUMMARY

In certain embodiments, an isolated polypeptide comprising an amino acid sequence having at least 80% identity to SEQ ID NO:1 is provided, wherein the polypeptide has nucleic acid binding activity. In certain embodiments, the isolated polypeptide comprises the amino acid sequence of SEQ ID NO:1 or a fragment thereof having nucleic acid binding activity.

In certain embodiments, an isolated polynucleotide is provided, wherein the isolated polynucleotide comprises a polynucleotide sequence encoding a polypeptide comprising an amino acid sequence having at least 80% identity to SEQ ID NO: 1, wherein the polypeptide has nucleic acid binding activity. In certain embodiments, the isolated polynucleotide comprises the polynucleotide sequence of SEQ ID NO:2. In certain embodiments, the isolated polynucleotide comprises the polynucleotide sequence of SEQ ID NO:3. In certain embodiments, a vector comprising the isolated polynucleotide is provided. In certain embodiments, a host cell comprising the vector is provided. In certain embodiments, a method of producing a polypeptide comprising an amino acid sequence having at least 80% identity to SEQ ID NO:1, wherein the polypeptide has nucleic acid binding activity, is provided, wherein the method comprises culturing, the host cell under conditions suitable for expression of the polypeptide and isolating the polypeptide so expressed.

In certain embodiments, an isolated polypeptide comprising an amino acid sequence having at least 80% identity to SEQ ID NO:4 is provided, wherein the polypeptide has nucleic acid binding activity. In certain embodiments, the isolated polypeptide comprises the amino acid sequence of SEQ ID NO:4 or a fragment thereof having nucleic acid binding activity.

In certain embodiments, an isolated polynucleotide is provided, wherein the isolated polynucleotide comprises a polynucleotide sequence encoding a polypeptide comprising an amino acid sequence having at least 80% identity to SEQ ID NO:4, wherein the polypeptide has nucleic acid binding activity. In certain embodiments, the isolated polynucleotide comprises, the polynucleotide sequence of SEQ ID NO:5. In certain embodiments, a vector comprising the isolated polynucleotide is provided. In certain embodiments, a host cell comprising the vector is provided. In certain embodiments, a method of producing a polypeptide comprising an amino acid sequence having at least 80% identity to SEQ ID NO:4, wherein the polypeptide has nucleic acid binding activity, is provided, wherein the method comprises culturing the host cell under conditions suitable for expression of the polypeptide and isolating the polypeptide so expressed.

In certain embodiments, an isolated polypeptide comprising an amino acid sequence having at least 80% identity to SEQ ID NO:6 is provided, wherein the polypeptide has nucleic acid binding activity. In certain embodiments, the isolated polypeptide comprises the amino acid sequence of SEQ ID NO:6 or a fragment thereof having nucleic acid binding activity.

In certain embodiments, an isolated polynucleotide is provided, wherein the isolated polynucleotide comprises a polynucleotide sequence encoding a polypeptide comprising an amino acid sequence having at least 80% identity to SEQ ID NO:6, wherein the polypeptide has nucleic acid binding activity. In certain embodiments, the isolated polynucleotide comprises, the polynucleotide sequence of SEQ ID NO:7. In certain embodiments, a vector comprising the isolated polynucleotide is provided. In certain embodiments, a host cell comprising the vector is provided. In certain embodiments, a method of producing a polypeptide comprising an amino acid sequence having at least 80% identity to SEQ ID NO:6, wherein the polypeptide has nucleic acid binding activity, is provided, wherein the method comprises culturing the host cell under conditions suitable for expression of the polypeptide and isolating the polypeptide so expressed.

In certain embodiments, an isolated polypeptide comprising the amino acid sequence of SEQ ID NO:28 is provided, wherein the polypeptide has:
nucleic acid binding activity.

In certain embodiments, a fusion protein is provided, wherein the fusion protein comprises, a polypeptide comprising the amino acid sequence of SEQ ID NO:28, wherein the polypeptide has nucleic acid binding activity, and a nucleic acid polymerase.

In certain embodiments, a fusion protein is provided, wherein the fusion protein comprises an amino acid sequence, of a Crenarchaeal nucleic acid binding polypeptide or a fragment thereof having nucleic acid binding activity, and a nucleic acid polymerase.

In certain embodiments, a fusion protein is provided, wherein the fusion protein comprises an amino acid sequence having at least 80% identity to SEQ ID NO:1, wherein the polypeptide has nucleic acid binding activity, and a nucleic acid polymerase. In certain embodiments, the nucleic acid polymerase is a thermostable DNA polymerase. In certain embodiments, the polypeptide comprises the amino acid sequence of SEQ ID NO:1 or a fragment of SEQ ID NO:1 that has nucleic acid binding activity.

In certain embodiments, a fusion protein is provided, wherein the fusion protein comprises an amino acid sequence having at least 80% identity to SEQ ID NO:4, wherein the polypeptide has nucleic acid binding activity, and a nucleic acid polymerase. In certain embodiments, the nucleic acid polymerase is a thermostable DNA polymerase. In certain embodiments, the polypeptide comprises the amino acid sequence of SEQ ID NO:4 or a fragment of SEQ ID NO:4 that has nucleic acid binding activity.

In certain embodiments, a fusion protein is provided, wherein the fusion protein comprises an amino acid sequence having at least 80% identity to SEQ ID NO:6, wherein the polypeptide has nucleic acid binding activity, and a nucleic acid polymerase. In certain embodiments, the nucleic acid polymerase is a thermostable DNA polymerase. In certain embodiments, the polypeptide comprises the amino acid sequence of SEQ ID NO:6 or a fragment of SEQ ID NO:6 that has nucleic acid binding activity.

In certain embodiments, a fusion protein comprising an amino acid sequence selected from SEQ ID NOs:23, 24, 26; 27, 34, 35, 37, 38, 40, 41, 43, and 44 is provided.

In certain embodiments, a method of stabilizing a nucleic acid duplex is provided, wherein the method comprises combining the nucleic acid duplex with a polypeptide comprising the amino acid sequence of SEQ ID NO:28, wherein the polypeptide has nucleic acid binding activity.

In certain embodiments, a method of stabilizing a nucleic acid duplex is provided, wherein the method comprises combining the nucleic acid duplex with a polypeptide comprising an amino acid sequence of a Crenarchaeal nucleic acid binding polypeptide or a fragment thereof having nucleic acid binding activity.

In certain embodiments, a method of stabilizing a nucleic acid duplex is provided, wherein the method comprises combining the nucleic acid duplex with a polypeptide comprising an amino acid sequence having at least 80% identity to SEQ ID NO:1, wherein the polypeptide has nucleic acid binding activity. In certain embodiments, the polypeptide comprises the amino acid sequence of SEQ ID NO:1 or a fragment of SEQ ID NO:1 that has nucleic acid binding activity.

In certain embodiments, a method of stabilizing a nucleic acid duplex is provided, wherein the method comprises combining the nucleic acid duplex with a polypeptide comprising an amino acid sequence having at least 80% identity to SEQ ID NO:4, wherein the polypeptide has nucleic acid binding activity. In certain embodiments, the polypeptide comprises the amino acid sequence of SEQ ID NO:4 or a fragment of SEQ ID NO:4 that has nucleic acid binding activity.

In certain embodiments, a method stabilizing a nucleic acid duplex is provided, wherein the method comprises combining the nucleic acid duplex with a polypeptide comprising an amino acid sequence having at least 80% identity to SEQ ID NO:6, wherein the polypeptide has nucleic acid binding activity. In certain embodiments, the polypeptide comprises the amino acid sequence of SEQ ID NO:6 or a fragment of SEQ ID NO:6 that has nucleic acid binding activity.

In certain embodiments, a method of promoting the annealing of complementary nucleic acid strands is provided, wherein the method comprises combining the complementary nucleic acid strands with a polypeptide comprising the amino acid sequence of SEQ ID NO:28, wherein the polypeptide has nucleic acid binding activity.

In certain embodiments, a method of promoting the annealing of complementary nucleic acid strands is provided, wherein the method comprises combining the complementary nucleic acid strands with a polypeptide comprising an amino acid sequence of a Crenarchaeal nucleic acid binding polypeptide or a fragment thereof having nucleic acid binding activity.

In certain embodiments, a method of promoting the annealing of complementary nucleic acid strands is provided, wherein the method comprises combining the complementary nucleic acid strands with a polypeptide comprising an amino acid sequence having at least 80% identity to SEQ ID NO:1, wherein the polypeptide has nucleic acid binding activity. In certain embodiments, the polypeptide comprises the amino acid sequence of SEQ ID NO:1 or a fragment of SEQ ID NO:1 that has nucleic acid binding activity.

In certain embodiments, a method of promoting the annealing of complementary nucleic acid strands is provided, wherein the method comprises combining the complementary nucleic acid strands with a polypeptide comprising an amino acid sequence having at least 80% identity to SEQ ID NO:4, wherein the polypeptide has nucleic acid binding activity. In certain embodiments, the polypeptide comprises the amino acid sequence of SEQ ID NO:4 or a fragment of SEQ ID NO:4 that has nucleic acid binding activity.

In certain embodiments, a method of promoting the annealing of complementary nucleic acid strands is provided, wherein the method comprises combining the complementary nucleic acid strands with a polypeptide comprising an amino acid sequence having at least 80% identity to SEQ ID NO:6, wherein the polypeptide has nucleic acid binding activity. In certain embodiments, the polypeptide comprises the amino acid sequence of SEQ ID NO:6 or a fragment of SEQ ID NO:6 having nucleic acid binding activity.

In certain embodiments, a method of increasing the processivity of a DNA polymerase is provided, wherein the method comprises combining a reaction mixture comprising the DNA polymerase with a polypeptide comprising the amino acid sequence of SEQ ID NO:28, wherein the polypeptide has nucleic acid binding activity.

In certain embodiments, a method of increasing the processivity of a DNA polymerase is provided, wherein the method comprises combining a reaction mixture comprising the DNA polymerase with a polypeptide comprising an amino acid sequence of a Crenarchaeal nucleic acid binding polypeptide or fragment thereof having nucleic acid binding activity.

In certain embodiments, a method of increasing the processivity of a DNA polymerase is provided, wherein the method comprises combining a reaction mixture comprising the DNA polymerase with a polypeptide comprising an amino acid sequence having at least 80% identity to SEQ ID NO:1, wherein the polypeptide has nucleic acid binding activity. In certain embodiments, the polypeptide comprises the amino acid sequence of SEQ ID NO:1 or a fragment of SEQ ID NO:1 that has nucleic acid binding activity.

In certain embodiments, a method of increasing the processivity of a DNA polymerase is provided, wherein the method comprises combining a reaction mixture comprising the DNA polymerase with a polypeptide comprising an amino acid sequence having at least 80% identity to SEQ ID NO:4, wherein the polypeptide has nucleic acid binding activity. In certain embodiments, the polypeptide comprises the amino acid sequence of SEQ ID NO:4 or a fragment of SEQ ID NO:4 that has nucleic acid binding activity.

In certain embodiments; a method of increasing the processivity of a DNA polymerase is provided, wherein the method comprises combining a reaction mixture comprising the DNA polymerase with a polypeptide comprising an amino acid sequence having at least 80% identity to SEQ ID NO:6, wherein the polypeptide has nucleic acid binding activity. In certain embodiments, the polypeptide comprises the amino acid sequence of SEQ ID NO:6 or a fragment of SEQ ID NO:6 that has nucleic acid binding activity.

In certain embodiments, a kit is provided, wherein the kit comprises a polypeptide comprising the amino acid sequence of SEQ ID NO:28, wherein the polypeptide has nucleic acid binding activity, and a nucleic acid modification enzyme.

In certain embodiments, a kit is provided, wherein the kit comprises a polypeptide comprising an amino acid sequence of a Crenarchaeal nucleic acid binding polypeptide or a fragment thereof having nucleic acid binding activity, and a nucleic acid modification enzyme.

In certain embodiments, a kit is provided, wherein the kit comprises a polypeptide comprising an amino acid sequence having at least 80% identity to SEQ ID NO:1, wherein the polypeptide has nucleic acid binding activity, and a nucleic acid modification enzyme. In certain embodiments, the polypeptide comprises the amino acid sequence of SEQ ID NO:1 or a fragment of SEQ ID NO:1 that has nucleic acid binding activity.

In certain embodiments, a kit is provided, wherein the kit comprises a polypeptide comprising an amino acid sequence having at least 80% identity to SEQ ID NO:4, wherein the polypeptide has nucleic acid binding activity, and a nucleic acid modification enzyme. In certain embodiments, the polypeptide comprises the amino acid sequence of SEQ ID NO:4 or a fragment of SEQ ID NO:4 that has nucleic acid binding activity.

In certain embodiments, a kit is provided, wherein the kit comprises a polypeptide comprising an amino acid sequence having at least 80% identity to SEQ ID NO:6, wherein the polypeptide has nucleic acid binding activity, and a nucleic acid modification enzyme. In certain embodiments, the polypeptide comprises the amino acid sequence of SEQ ID NO:6 or a fragment thereof having nucleic acid binding activity.

In certain embodiments of any of the above kits, the nucleic acid modification enzyme is a thermostable DNA polymerase.

In certain embodiments, a kit is provided, wherein the kit comprises any of the above fusion proteins and deoxyribonucleotides.

IV. DETAILED DESCRIPTION OF VARIOUS EMBODIMENTS

In this application, the use of the singular includes the plural unless specifically stated otherwise. In this application, the word "a" or "an" means "at least one" unless specifically stated otherwise. In this application, the use of "or" means "and/or" unless stated otherwise. Furthermore, the use of the term "including," as, well as other forms, such as "includes" and "included," is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated literature and similar materials defines a term that contradicts that term's definition in this application, this application controls.

A. Certain Definitions

It is to be understood that both the foregoing general description and the following detailed description are exemplary and explanatory only and are not restrictive of the invention, as claimed.

"Crenarchaeal nucleic acid binding polypeptide" refers to a naturally occurring Crenarchaeal polypeptide that has a molecular weight of about 6 to 11 kilodaltons and a predicted isoelectric point of about 9 to 11; that comprises less than or equal to 4 arginine residues and less than or equal to 15 lysine residues; that has nucleic acid binding activity; and that has an amino acid sequence that is less than 50% identical to the amino acid sequence of Sso7d (SEQ ID NO:30). The Crenarchaea include, but are not limited to, members of the genus *Pyrobaculum, Thermoproteus, Thermocladium, Caldivirga, Thermofilum, Staphylothermus, Ignicocus, Aeropyrum, Pyrodictium, Pyrolobus, Sulfolobus*, and *Metallosphaera*. See, e.g., Fitz-Gibbon et al. (2002) *Proc. Nat'l Acad. Sci. USA* 99:984-989.

"Nucleic acid binding activity" refers to the activity of a polypeptide in binding nucleic acid in at least one of the following two band-shift assays. In the first assay (based on the assay of Guagliardi et al. (1997) *J. Mol. Biol.* 267:841-848), double stranded nucleic acid (the 452-bp HindIII-EcoRV fragment from the *S. solfataricus* lacS gene) is labeled with $^{32}$P to a specific activity of at least about $2.5 \times 10^7$ cpm/ug (or at least about 4000 cpm/fmol) using standard methods. See, e.g., Sambrook et at (2001) *Molecular Cloning: A Laboratory Manual* ($3^{rd}$ ed., Cold Spring Harbor. Laboratory Press, NY), at 9.63-9.75 (describing end-labeling of nucleic acids). A reaction mixture is prepared containing at least about 0.5 μg of the polypeptide in about 10 μl of binding buffer (50 mM sodium phosphate buffer (pH 8.0), 10% glycerol, 25 mM KCl, 25 mM $MgCl_2$). The reaction mixture is heated to 37° C. for ten minutes. About $1 \times 10^4$ to $5 \times 10^4$ cpm (or about 0.5-2 ng) of the labeled double stranded nucleic acid is added to the reaction mixture and incubated for an additional ten minutes. The reaction mixture is loaded onto a native polyacrylamide gel in 0.5× Tris-borate buffer. The reaction mixture is subjected to electrophoresis at room temperature. The gel is dried and subjected to autoradiography using standard methods. Any detectable decrease in the mobility of the labeled double stranded nucleic acid indicates formation of a binding complex between the polypeptide and the double stranded nucleic acid. Such nucleic acid binding activity may be quantified using standard densitometric methods to measure the amount of radioactivity in the binding complex relative to the total amount of radioactivity in the initial reaction mixture.

In the second assay (based on the assay of Mai et al. (1998) *J. Bacteriol.* 180:2560-2563), about 0.5 μg each of negatively supercoiled circular pBluescript KS(−) plasmid and nicked circular pBluescript KS(−) plasmid (Stratagene, La Jolla, Calif.) are mixed with a polypeptide at a polypeptide/DNA mass ratio of about ≥2.6. The mixture is incubated for 10 minutes at 40° C. The mixture is subjected to 0.8% agarose gel electrophoresis. DNA is visualized using an appropriate dye. Any detectable decrease in the mobility of the negatively supercoiled circular plasmid and/or nicked circular plasmid indicates formation of a binding complex between the polypeptide and the plasmid.

"Fusion protein" refers to a protein comprising two or more domains joined either covalently or noncovalently, wherein two or more of the domains do not naturally occur in a single protein.

"Nucleic acid polymerase" refers to a polypeptide that catalyzes the synthesis of a polynucleotide using an existing polynucleotide as a template.

"Polymerase activity" refers to the activity of a nucleic acid polymerase in catalyzing the template-directed synthesis of a new polynucleotide. Polymerase activity is measured using the following assay, which is based on that of Lawyer et al.

(1989) *J. Biol. Chem.* 264:6427-647. Serial dilutions of polymerase are prepared in dilution buffer (20 mM Tris Cl, pH 8.0, 50 mM KCl, 0.5% NP 40, and 0.5% Tween-20). For each dilution, 5 µl is removed and added to 45 µl of a reaction mixture containing 25 mM TAPS (pH 9.25), 50 mM KCl, 2 mM MgCl$_2$, 0.2 mM dATP, 0.2 mM dGTP, 0.2 mM dTTP, 0.1 mM dCTP, 12.5 µg activated DNA, 100 µM [α-$^{32}$P] dCTP (0.05 µCi/nmol) and sterile deionized water. The reaction mixtures are incubated at 37° C. (or 74° C. for thermostable DNA polymerases) for 10 minutes and then stopped by immediately cooling the reaction to 4° C. and adding 10 µl of ice-cold 60 mM EDTA. A 25 µl aliquot is removed from each reaction mixture. Unincorporated radioactively labeled dCTP is removed from each aliquot by gel filtration (Centri-Sep, Princeton Separations, Adelphia, N.J.). The column eluate is mixed with scintillation fluid (1 ml). Radioactivity in the column eluate is quantified with a scintillation counter to determine the amount of product synthesized by the polymerase. One unit of polymerase activity is defined as the amount of polymerase necessary to synthesize 10 nmole of product in 30 minutes.

"DNA Polymerase" refers to a nucleic acid polymerase that catalyzes the template-directed synthesis of DNA.

"Processivity" refers to the extent of polymerization by a nucleic acid polymerase during a single contact between the polymerase and its template. The extent of polymerization refers to the number of nucleotides added by the polymerase during a single contact between the polymerase and its template.

"Thermostable DNA polymerase" refers to a DNA polymerase that, at a temperature higher than 37° C., retains its ability to add at least one nucleotide onto the 3' end of a primer or primer extension product that is annealed to a target nucleic acid sequence. In certain embodiments, a thermostable DNA polymerase remains active at a temperature greater than about 37° C. In certain embodiments, a thermostable DNA polymerase remains active at a temperature greater than about 42° C. In certain embodiments, a thermostable DNA polymerase remains active at a temperature greater than about 50° C. In certain embodiments, a thermostable DNA polymerase remains active at a temperature greater than about 60° C. In certain embodiments, a thermostable DNA polymerase remains active at a temperature greater than about 70° C. In certain embodiments, a thermostable DNA polymerase remains active at a temperature greater than about 80° C. In certain embodiments, a thermostable polymerase remains active at a temperature greater than about 90° C.

"Percent identity" or "% identity," with reference to nucleic acid sequences, refers to the percentage of identical nucleotides between at least two polynucleotide sequences aligned using the Basic Local Alignment Search Tool (BLAST) engine. See Tatusova et al. (1999) *FEMS Microbiol Lett.* 174:247-250. The BLAST engine (version 2:2.10) is provided to the public by the National Center for Biotechnology Information (NCBI), Bethesda, Md. To align two polynucleotide sequences, the "Blast 2 Sequences" tool is used, which employs the "blastn" program with parameters set at default values as follows:
 Matrix: not applicable
 Reward for match: 1
 Penalty for mismatch: −2
 Open gap: 5 penalties
 Extension gap: 2 penalties
 Gap_x dropoff: 50
 Expect: 10.0
 Word size: 11
 Filter: on "Percent identity" or "% identity," with reference to polypeptide sequences, refers to the percentage of identical amino acids between at least two polypeptide sequences aligned using the Basic Local Alignment Search Tool (BLAST) engine. See Tatusova et at. (1999) *FEMS Microbiol Lett.* 174:247-250. The BLAST engine (version 2.2.10) is provided to the public by the National Center for Biotechnology Information (NCBI), Bethesda, Md. To align two polypeptide sequences, the "Blast 2 Sequences" tool is used, which employs the "blastp" program with parameters set at default value as follows:
 Matrix: BLOSUM62
 Open gap: 11 penalties
 Extension gap: 1 penalty
 Gap_x dropoff: 50
 Expect: 10.0
 Word size: 3
 Filter: on The terms "polypeptide," "peptide," and "protein" are used interchangeably herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

A "fragment" of a reference polypeptide refers to a contiguous stretch of amino acids from any portion of the reference polypeptide. A fragment may be of any length that is less than the length of the reference polypeptide.

A "variant" of a reference polypeptide refers to a polypeptide having one or more amino acid substitutions, deletions, or insertions relative to the reference polypeptide. Exemplary conservative substitutions include, but are not limited to, those set forth below:

TABLE 1

Exemplary Amino Acid Substitutions

| Original Residues | Exemplary Substitutions |
|---|---|
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala, Phe, Norleucine |
| Leu | Norleucine, Ile, Val, Met, Ala, Phe |
| Lys | Arg, 1,4 Diamino-butyric Acid, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala, Norleucine |

"Nucleic acid modification enzyme" refers to an enzymatically active polypeptide that acts on a nucleic acid substrate. Nucleic acid modification enzymes include, but are not limited to, nucleic acid polymerases (such as DNA polymerases and RNA polymerases), nucleases (including endonucleases, such as restriction endonucleases, and exonucleases, such as 3' or 5' exonucleases), gyrases, topoisomerases, methylases, and ligases.

"Melting temperature" or "Tm" refers to the temperature at which 50% of the base pairs in a double-stranded nucleic acid have denatured. "Predicted Tm" refers to the Tm calculated for a nucleic acid using the following equation:

$$Tm = 81.5°\,C. + 16.6\,\log_{10}[M^+] + 0.41(\%[G+C])$$

where [M⁺] is the monovalent cation concentration for M⁺≤0.5 M. See Sambrook et al. (2001) *Molecular Cloning: A Laboratory Manual* (3rd ed., Cold Spring Harbor Laboratory Press, NY) at 10.47.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 6 methyl-cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2 ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman (1989) *Practical Handbook of Biochemistry and Molecular Biology*, pages 385-394, (CRC Press, Boca Raton, Fla.) and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —NR₂ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14) aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anonmeric nucleotides, 2'-4'- and 3'-4'-linked and other "locked" or "LNA", bicyclic sugar modifications (see, e.g., PCT published application nos. WO 98/22489, WO 98/39352; and WO 99/14226). Exemplary LNA sugar analogs within a polynucleotide include, but are not limited to, the structures:

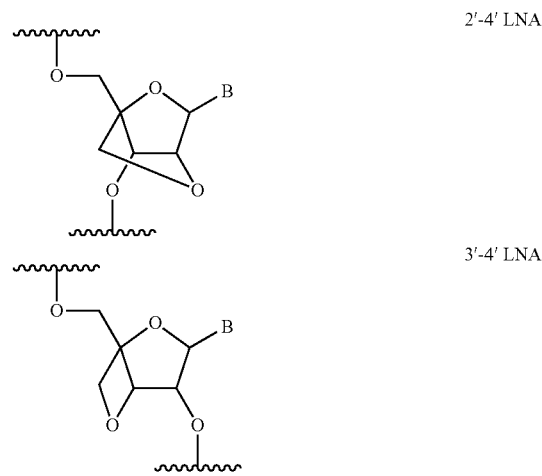

where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) *Nucl. Acids Res.* 21:4159-65; Fujimori (1990) *J. Amer. Chem. Soc.* 112:7435; Urata, (1993) *Nucleic Acids Symposium* Ser. No. 29:69-70). When the nucleotide base is purine, e.g. A or G, the ribose sugar is attached to the $N^9$-position of the nucleotide base. When the nucleotide base is pyrimidine; e.g., C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) *DNA Replication*, 2nd Ed., Freeman, San Francisco, Calif.).

One or more of the pentose carbons of a nucleotide may be substituted with a phosphate ester having the formula:

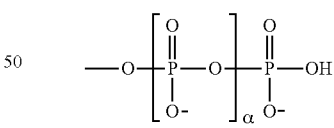

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and is sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

The term "nucleotide analog," as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphsosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers that can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide," "oligonucleotide," and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A" denotes deoxyadenosine or an analog thereof, "C" denotes deoxycytidine or an analog thereof, "G" denotes deoxyguanosine or an analog thereof, "T" denotes thymidine or an analog thereof, and "U" denotes uridine or an analog thereof, unless otherwise noted.

Nucleic acids include, but are not limited to, genomic DNA, cDNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample. Nucleic acids include, but are not limited to, synthetic or in vitro transcription products.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

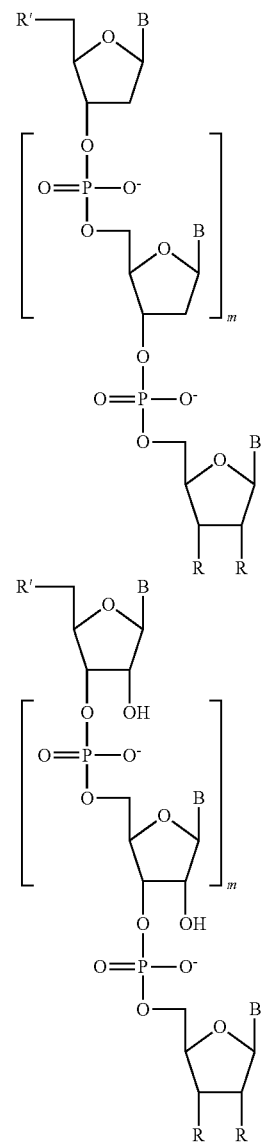

wherein each B is independently the base moiety of a nucleotide, e.g., a purine, a 7-deazapurine, a pyrimidine, or an analog nucleotide; each m defines the length of the respective nucleic acid and can range from zero to thousands, tens of thousands, or even more; each R is independently selected from the group comprising hydrogen, halogen, —R", —OR", and —NR"H", where each R" is independently (C1-C6) alkyl or (C5-C14) aryl, or two adjacent Rs are taken together to form a bond such that the ribose sugar is 2',3'-didehydroribose; and each R' is independently hydroxyl or

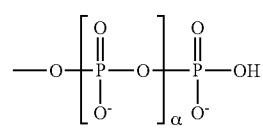

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid," "polynucleotide," and "oligonucleotide" may also include nucleic acid analogs, polynucleotide analogs and oligonucleotide analogs. The terms "nucleic acid analog", "polynucleotide analog" and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al.; 1991, Science 254:1497-1500; WO:92/20702; U.S. Pat. No. 5,719,262; U.S. Pat. No. 5,698,685;); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114:4006); 3'-thioformacetals (see, e.g., Jones at al., 1993, J. Org. Chem. 58:2983); sulfamates (see, e.g., U.S. Pat. No. 5,470,967); 2-aminoethylglycine, commonly referred to as PNA (see, e.g., Buchardt, WO 92/20702; Nielsen (1991) Science 254: 1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

In this application, a statement that one sequence is the same as or is complementary, to another sequence encompasses situations where both of the sequences are completely the same or complementary to one another, and situations where only a portion of one of the sequences is the same as, or is complementary to, a portion or the entirety of the other sequence. Here, the term "sequence" encompasses, but is not limited to, nucleic acid sequences, polynucleotides, oligonucleotides, probes, and primers.

In this application, a statement that one sequence is complementary to another sequence encompasses situations in which the two sequences have mismatches. Here, the term "sequence" encompasses, but is not limited to, nucleic acid sequences, polynucleotides, oligonucleotides, probes, and primers. Despite the mismatches, the two sequences should selectively hybridize to one another under appropriate conditions.

The term "selectively hybridize" means that, for particular identical sequences, a substantial portion of the particular identical sequences hybridize to a given desired sequence or sequences, and a substantial portion of the particular identical sequences do not hybridize to other undesired sequences. A "substantial portion of the particular identical sequences" in each instance refers to a portion of the total number of the particular identical sequences, and it does not refer to a portion of an individual particular identical sequence. In certain embodiments, "a substantial portion of the particular identical sequences" means at least 70% of the particular identical sequences. In certain embodiments, "a substantial portion of the particular identical sequences" means at least 80% of the particular identical sequences. In certain embodiments, "a substantial portion of the particular identical sequences means at least 90% of the particular identical sequences. In certain embodiments, "a substantial portion of the particular identical sequences" means at least 95% of the particular identical sequences.

In certain embodiments, the number of mismatches that may be present may vary in view of the complexity of the composition. Thus, in certain embodiments, the more complex the composition, the more likely undesired sequences will hybridize. For example, in certain embodiments, with a given number of mismatches, a probe may more likely hybridize to undesired sequences in a composition with the entire genomic DNA than in a composition with fewer DNA sequences, when the same hybridization and wash conditions are employed for both compositions. Thus, that given number of mismatches may be appropriate for the composition with fewer DNA sequences, but fewer mismatches may be more optimal for the composition with the entire genomic DNA.

In certain embodiments, sequences are complementary if they have no more than 20% mismatched nucleotides. In certain embodiments, sequences are complementary if they have no more than 15% mismatched nucleotides. In certain embodiments, sequences are complementary if they have no more than 10% mismatched nucleotides. In certain embodiments, sequences are complementary if they have no more than 5% mismatched nucleotides.

In this application, a statement that one sequence hybridizes or binds to another sequence encompasses situations where the entirety of both of the sequences hybridize or bind to one another, and situations where only a portion of one or both of the sequences hybridizes or binds to the entire other sequence or to a portion of the other sequence. Here, the term "sequence" encompasses, but is not limited to, nucleic acid sequences, polynucleotides, oligonucleotides, probes, and primers.

A "target," "target nucleic acid," or "target polynucleotide" refers to a nucleic acid comprising a sequence that can be distinguished by a probe or primer. In certain embodiments, a target polynucleotide is naturally occurring. In certain embodiments a target polynucleotide comprises synthetic molecules.

The term "primer" refers to a polynucleotide that anneals to a target polynucleotide and allows the synthesis from its 3' end of a sequence complementary to the target polynucleotide.

The term "primer extension reaction" refers to a reaction in which a polymerase catalyzes the template-directed synthesis of a nucleic acid from the 3' end of a primer. The term "primer extension product" refers to the resultant nucleic acid. A non-limiting exemplary primer extension reaction is the polymerase chain reaction (PCR).

The term "probe" comprises a polynucleotide that comprises a specific portion designed to hybridize in a sequence-specific manner with a complementary region of a specific nucleic acid sequence, e.g., a target polynucleotide. In certain embodiments, the specific portion of the probe may be specific for a particular sequence, or alternatively, may be degenerate, e.g., specific for a set of sequences.

The terms "annealing" and "hybridization" are used interchangeably and mean the base-pairing interaction of one nucleic acid with another nucleic acid that results in the formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

A "nucleic acid duplex" refers to any nucleic acid or portion of a nucleic acid that exists in double stranded form. Double stranded nucleic acid includes homoduplexes, such as double stranded DNA, and heteroduplexes, such as DNA: RNA or DNA:PNA heteroduplexes. Double stranded nucleic acid also includes, for example, a region of a nucleic acid strand to which a primer or probe has annealed.

B. Certain Nucleic Acid Binding Polypeptides from *Sulfolobus*

Certain small, basic DNA binding polypeptides from the hyperthermophilic archaeotes *Sulfolobus solfataricus* and *Sulfolobus acidocaldarius* have been discovered. These polypeptides, which include Sso7d and Sac7d, bind DNA in a sequence non-specific manner. See Gao et al. (1998) *Nature Struct. Biol.* 5:782-786; Robinson et al. (1998) *Nature* 392: 202-205; McAfee et al. (1995) *Biochem.* 34:10063-10077; and Baumann et al. (1994) *Nature Struct. Biol.* 1:808-819. Sso7d and Sac7d are of relatively low molecular weight (about 7 kDa) and are rich in lysine residues. Id. Certain lysine residues are believed to be involved in DNA binding. See Gao et al. (1998) *Nature Struct. Biol.* 5:782-786. Both protect double stranded DNA from thermal denaturation by increasing its melting temperature (Tm) by about 40° C. Id.; Robinson et al. (1998) *Nature* 392:202-205. Sso7d also promotes the annealing of complementary DNA strands at temperatures exceeding the predicted Tm of the resulting duplex. See Guagliardi et al. (1997) *J. Mol. Biol.* 267:841-848. Sso7d exhibits a strong preference for DNA strands that are complementary without any mismatches over DNA strands that contain even a single mismatch. See id.; U.S. Patent Application Publication No. US 2003/0022162 A1. It is postulated that small, basic polypeptides such as Sso7d and Sac7d protect the DNA of hyperthermophiles from denaturation and degradation in the hyperthermophilic environment, where temperatures approach or exceed 100° C. See Guagliardi et al. (1997) *J. Mol. Biol.* 267:841-848.

C. Certain Exemplary Components

In certain embodiments, an isolated polypeptide having nucleic acid binding activity is provided. A polypeptide having nucleic acid binding activity is also referred to herein as a "nucleic acid binding polypeptide." In certain embodiments, an isolated nucleic acid binding polypeptide has a relatively low molecular weight and basic isoelectric point. In certain embodiments, a nucleic acid binding polypeptide stabilizes a double stranded nucleic acid from denaturation or promotes the annealing of complementary nucleic acid strands. In certain embodiments, a fusion protein comprising a nucleic acid binding polypeptide is provided. In certain such embodiments, a fusion protein comprises a nucleic acid binding polypeptide joined to a nucleic acid modification enzyme, such as a DNA polymerase.

1. Nucleic Acid Binding Polypeptides

In certain embodiments, an isolated nucleic acid binding polypeptide comprises a Crenarchaeal nucleic acid binding polypeptide. In certain embodiments, a Crenarchaeal nucleic acid binding polypeptide comprises a naturally occurring polypeptide from the crenarchaeon *Pyrobaculum aerophilum*. In certain embodiments, a Crenarchaeal nucleic acid binding polypeptide comprises the amino acid sequence of SEQ ID NO:1; which can be found at GenBank accession numbers AAL64739 and AAL64814. SEQ ID NO:1 is encoded by the open reading frames "PAE3192" (SEQ ID NO:2) and "PAE3289" (SEQ ID NO:3) which are unannotated open reading frames identified in the complete genome sequence of *P. aerophilum*. See GenBank accession no. AE009441.

In certain embodiments, a Crenarchaeal nucleic acid binding polypeptide comprises the amino acid sequence of SEQ ID NO:4, which can be found at GenBank accession number AAL62754. SEQ ID NO:4 is encoded by the open reading frame "PAE0384" (SEQ ID NO:5), which is an unannotated open reading frame identified in the complete genome sequence of *P. aerophilum*. See GenBank accession no. AE009441.

SEQ ID NOs:1 and 4 are low molecular weight, basic proteins of 57 and 56 amino acids in length, respectively, with a predicted isoelectric point of about 10.5. SEQ ID.NO:1 contains 12 lysine residues and 2 arginine residues. SEQ ID NO:4 contains 11 lysine residues and 2 arginine residues. SEQ ID NOs:1 and 4 are about 97% identical to each other. SEQ ID NOs:1 and 4 are similar in size and charge to Sso7d, but they are not significantly identical to the amino acid sequence of Sso7d. Additionally, SEQ ID NO:1 contains a "KKOK" motif (SEQ ID NO: 47) near its N-terminus (residues 3 to 6 of SEQ ID NO:1). This motif resembles the "KQKK" motif (SEQ ID NO: 47) found at the C-terminus of Sso7d (residues 61-64 of SEQ ID NO:30). The location of these motifs at opposite termini of SEQ ID NO:1 and Sso7d may have resulted from gene rearrangements during the divergence of the different Crenarchaeal species. The KQKK motif (SEQ ID NO: 47) of Sso7d is discussed in Shehi et al. (2003) *Biochem.* 42:8362-8368.

In certain embodiments, an isolated nucleic acid binding polypeptide comprises a fragment of SEQ ID NO:1 that has at least one activity of a polypeptide comprising SEQ ID NO:1. Exemplary activities include, but are not limited to, the ability of SEQ ID NO:1 to bind nucleic acid, stabilize nucleic acid duplexes, promote annealing of complementary nucleic acid strands, increase the Tm of primers, enhance the activity of a nucleic acid modification enzyme, and increase the processivity of a polymerase. In certain embodiments, a fragment of SEQ ID NO:1 lacks N-terminal amino acids of SEQ ID NO:1. In certain such embodiments, the fragment of SEQ ID NO:1 lacks up to the first 12 N-terminal amino acids of SEQ ID NO:1. In certain embodiments, a fragment of SEQ ID NO:1 lacks C-terminal amino acids of SEQ ID NO:1. In certain such embodiments, the fragment of SEQ ID NO:1 lacks up to the last 12 C-terminal amino acids of SEQ ID NO:1. In certain embodiments, a fragment of SEQ ID NO:1 has a predicted isoelectric point of about 9-11.

In certain embodiments, an isolated nucleic acid binding polypeptide comprises a variant of a polypeptide comprising SEQ ID NO:1 that has at least one activity of a polypeptide comprising SEQ ID NO:1. In certain embodiments, a variant of a polypeptide comprising SEQ ID NO:1 comprises an amino acid sequence having from about 60% to about 99% identity to SEQ ID NO:1. For example, in certain embodiments, a variant of a polypeptide comprising SEQ ID NO:1 comprises an amino acid sequence having at least 60%, 65%, 70%, 75%, 80%, 85%, 90%, 95%, 97%, 98%, or 99% identity to SEQ ID NO:1. In certain such embodiments, the lysine and arginine residues of SEQ ID NO:1 are not substituted or deleted in the variant.

In certain embodiments, an isolated nucleic acid binding polypeptide comprises a fragment of SEQ ID NO:4 that has at least one activity of a polypeptide comprising SEQ ID NO:4. Exemplary activities include, but are not limited to, the ability of SEQ ID NO:4 to bind nucleic acid, stabilize nucleic acid duplexes, promote annealing of complementary nucleic acid strands, increase the Tm of primers, enhance the activity of a nucleic acid modification enzyme, and increase the processivity of a polymerase. In certain embodiments, a fragment of SEQ ID NO:4 lacks N-terminal amino acids of SEQ ID NO:4. In certain such embodiments, the fragment of SEQ ID NO:4 lacks up to the first 12 N-terminal amino acids of SEQ ID NO:4. In certain embodiments, a fragment of SEQ ID NO:4 lacks C-terminal amino acids of SEQ ID NO:4. In certain such embodiments, the fragment of SEQ ID NO:4 lacks up to the last 12 C-terminal amino acids of SEQ ID NO:4. In certain embodiments, a fragment of SEQ ID NO:4 has a predicted isoelectric point of about 9-11.

In certain embodiments, an isolated nucleic acid binding polypeptide comprises a variant of a polypeptide comprising SEQ ID NO:4 that has at least one activity of a polypeptide comprising SEQ ID NO:4. In certain embodiments, a variant of a polypeptide comprising SEQ ID NO:4 comprises an amino acid sequence having from about 60% to about 99% identity to SEQ ID NO:4. For example, in certain embodiments, a variant of a polypeptide comprising SEQ ID NO:4 comprises an amino acid sequence having at least 60%, 65%, 70%, 75%, 80%, 85%, 90%, 95%, 97%, 98%, or 99% identity to SEQ ID NO:4. In certain such embodiments, the lysine and arginine residues of SEQ ID NO:4 are not substituted or deleted in the variant.

In certain embodiments, a Crenarchaeal nucleic acid binding polypeptide comprises a naturally occurring polypeptide from the crenarchaeon *Aeropyrum pernix*. In certain embodiments, a Crenarchaeal nucleic acid binding polypeptide comprises the amino acid sequence of SEQ ID NO:6. SEQ ID NO:6 is 55 amino acids in length with a predicted isoelectric point of about 10.5. It contains 13 lysine residues and 3 arginine residues. SEQ ID NO:6 is similar in size and charge to Sso7d, but is not significantly identical to the amino acid sequence of Sso7d.

In certain embodiments, an isolated nucleic acid binding polypeptide comprises a fragment of SEQ ID NO:6 that has at least one activity of a polypeptide comprising SEQ ID NO:6. Exemplary activities include, but are not limited to, the ability of SEQ ID NO:6 to bind nucleic acid, stabilize nucleic acid duplexes, promote annealing of complementary nucleic acid strands, increase the Tm of primers, enhance the activity of a nucleic acid modification enzyme, and increase the processivity of a polymerase. In certain embodiments, a fragment of SEQ ID NO:6 lacks N-terminal amino acids of SEQ ID NO:6. In certain such embodiments, the fragment of SEQ ID NO:6 lacks up to the first 12 N-terminal amino acids of SEQ ID NO:6. In certain embodiments, a fragment of SEQ ID NO:6 lacks C-terminal amino acids of SEQ ID NO:6. In certain such embodiments, the fragment of SEQ ID NO:6 lacks up to the last 12 C-terminal amino acids of SEQ ID NO:6. In certain embodiments, a fragment of SEQ ID NO:6 has a predicted isoelectric point of about 9-11.

In certain embodiments, an isolated nucleic acid binding polypeptide comprises a variant of a polypeptide comprising SEQ ID NO:6 that has at least one activity of a polypeptide comprising SEQ ID NO:6. In certain embodiments, a variant of a polypeptide comprising SEQ ID NO:6 comprises an amino acid sequence having from about 60% to about 99% identity to SEQ ID NO:6. For example, in certain embodiments, a variant of a polypeptide comprising SEQ ID NO:6 comprises an amino acid sequence having at least 60%, 65%, 70%, 75%, 80%, 85%, 90%, 95%, 97%, 98%, or 99% identity to SEQ ID NO:6. In certain such embodiments, the lysine and arginine residues of SEQ ID NO:6 are not substituted or deleted in the variant.

In certain embodiments, an isolated polynucleotide comprising a nucleic acid sequence encoding SEQ ID NO:6 is provided. In certain embodiments, an isolated polynucleotide comprises a nucleic acid sequence encoding a fragment of SEQ ID NO:6 having at least one activity of a polypeptide comprising SEQ ID NO:6. In certain embodiments, an isolated polynucleotide comprises a nucleic acid sequence encoding a variant of a polypeptide comprising SEQ ID NO:6 having at least one activity of a polypeptide comprising SEQ ID NO:6.

In certain embodiments, an isolated polynucleotide comprising SEQ ID NO:7 is provided. In certain embodiments, an isolated polynucleotide comprises a fragment of SEQ ID NO:7 that encodes a polypeptide having at least one activity of a polypeptide comprising SEQ ID NO:6. In certain embodiments, an isolated polynucleotide comprises a variant of a polynucleotide comprising SEQ ID NO:7 that encodes a polypeptide having at least one activity of a polypeptide comprising SEQ ID NO:6. In certain embodiments, a variant of a polynucleotide comprising SEQ ID NO:7 comprises a nucleic acid sequence having from about 60% to about 99% identity to SEQ ID NO:7 and that encodes a polypeptide having at least one activity of a polypeptide comprising SEQ ID NO:6. For example, in certain embodiments, a variant of a polynucleotide comprising SEQ ID NO:7 comprises a nucleic acid sequence having at least 60%, 65%, 70%, 75%, 80%, 85%, 90%, 95%, 97%, 98%, or 99% identity to SEQ ID NO:7 and that encodes a polypeptide having at least one activity of a polypeptide comprising SEQ ID NO:6.

In certain embodiments, the length of an isolated polynucleotide is any number of nucleotides less than or equal to 10,000. For example, in certain embodiments, an isolated polynucleotide is less than or equal to 10,000, 9000, 8000, 7000, 6000, 5000, 4000, 3000, 2000, 1000, or 500 nucleotides in length. In certain embodiments, the length of an isolated polynucleotide does not include vector sequences.

In certain embodiments, a fragment or variant of a Crenarchaeal nucleic acid binding polypeptide has nucleic acid binding activity that is less than the nucleic acid binding activity of the Crenarchaeal nucleic acid binding polypeptide. In certain embodiments, a fragment or variant of a Crenarchaeal nucleic acid binding polypeptide has from about 10-20%, about 20-30%, about 30-40%, about 40-50%, about 50-60%, about 60-70%, about 70-80%, about 80-90%, or about 90-95% of the nucleic acid binding activity of the Crenarchaeal nucleic acid binding polypeptide.

The first of the two alignments below demonstrates that SEQ ID NOs:1 and 6 have 60% identity and 74% similarity as determined by the "Blast 2 Sequence" blastp program set at default parameters. (In calculating percent similarity, the blastp program includes both identical and similar amino acids. Similar amino acids are indicated by "+" signs in the alignments below.) The second of the two alignments below demonstrates that SEQ ID NOs:4 and 6 have 59% identity and 72% similarity as determined by the "Blast 2 Sequence" blastp program set at default parameters. In certain embodiments, one or more amino acids that are not conserved in at least one of the alignments below (i.e., amino acids that are not identical or similar) are substituted or deleted to create variants of polypeptides comprising SEQ ID NO:1, SEQ ID NO:4, or SEQ ID NO:6.

SEQ ID NO: 1:
1 MSKKQKLKFYDIKAKQAFETDQYEVIEKQTARGPMMFAVAKSPYTGIKVYRLLGKKK 57

M KK+K+KF+D+ AK+ +ETD YEV  K+T RG   FA AKSPYTG   YR+LGK

SEQ ID NO: 6:
1 MPKKEKIKFFDLVAKKYYETDNYEVEIKETKRGKFRFAKAKSPYTGKIFYRVLGKA 55

SEQ ID NO: 4:
1 MAKQKLKFYDIKAKQSFETDKYEVIEKETARGPMLFAVATSPYTGIKVYRLLGKKK 56

K+K+KF+D+ AK+ +ETD YEV  KET RG   FA A SPYTG   YR+LGK

SEQ ID NO: 6:
1 MPKKEKIKFFDLVAKKYYETDNYEVEIKETKRGKFRFAKAKSPYTGKIFYRVLGKA 55

Based on the above alignments, a consensus sequence for a nucleic acid binding polypeptide is provided as follows:

SEQ ID NO: 28
5' KXKXKFXDXXAKXXXETDXYEVXXKXTXRGXXXFAXAKSPYTGXX XYRXLGK 3'

In the above consensus sequence, "X" is any amino acid. In certain embodiments, an isolated nucleic acid binding polypeptide comprises an amino acid sequence that conforms to that consensus sequence. In certain such embodiments, the isolated nucleic acid binding polypeptide has at least one activity of a polypeptide comprising SEQ ID NO:1, SEQ ID NO:4, or SEQ ID NO:6.

In certain embodiments, a polynucleotide encoding a nucleic acid binding polypeptide is obtained by the polymerase chain reaction (PCR). Certain methods employing PCR are known to those skilled in the art. See, e.g., Sambrook et al. (2001) *Molecular Cloning: A Laboratory Manual*, Chapter 8 (3rd ed., Cold Spring Harbor Laboratory Press, NY). In certain embodiments, a polynucleotide comprising all or a portion of the coding sequence of a nucleic acid binding polypeptide is amplified using appropriate primers. In certain embodiments, restriction enzyme sites are included in the primers to facilitate cloning of the amplification product into an appropriate expression vector. In certain embodiments, the polynucleotide is amplified from genomic DNA or from cDNA of a crenarchaeote. The complete genome sequence of certain crenarchaeotes is published and may be used in designing primers for PCR. See, e.g., Fitz-Gibbon et al. (2002) *Proc. Nat'l Acad. Sci. USA* 99:984-989; Kawarabayasi (1999) *DNA Research* Supp:145-152; and She et al (2001) *Proc. Nat'l Acad. Sci. USA* 98:7835-7840.

In certain embodiments, a polynucleotide encoding a nucleic acid binding polypeptide is obtained by synthesizing individual oligonucleotides which are ligated end-to-end in vitro, with the resulting ligation product comprising the coding sequence of a nucleic acid binding polypeptide. In certain embodiments, the ligation product is amplified by PCR. In certain embodiments, the oligonucleotides overlap in sequence, and are extended by PCR, resulting in a PCR product comprising the coding sequence of a nucleic acid binding polypeptide. See, e.g., Stemmer et al. (1995) *Gene* 164:49-53; Gronlund et at (2003) *J. Biol. Chem.* 278:40144-40151. In certain embodiments, the PCR product is cloned into an appropriate expression vector.

In certain embodiments, a polynucleotide encoding a nucleic acid binding polypeptide is cloned into a suitable vector. In certain such embodiments, the vector is transferred (e.g., transformed or transfected) into a host cell. In certain embodiments, a polynucleotide encoding a nucleic acid binding polypeptide is cloned into an expression vector and, in certain embodiments, expressed in a suitable host cell. Certain exemplary expression vectors are available for use in certain host cells including, but not limited to, prokaryotes, yeast cells, insect cells, plant cells, and mammalian cells. See, e.g., Ausubel et al. (1991) *Current Protocols in Molecular Biology*, Chapter 16, John Wiley & Sons, New York. Certain expression vectors for the inducible expression of recombinant proteins in prokaryotes are known to those skilled in the art. For example, in certain embodiments, a polynucleotide encoding a nucleic acid binding polypeptide is cloned into an expression vector such that its transcription is under the control of an inducible promoter, such as the T7 bacteriophage promoter, the T5 promoter, or the tac promoter. See, e.g., the pET series of vectors (Invitrogen, Carlsbad, Calif.), the pQE series of vectors (Qiagen, Valencia, Calif.), or the pGEX series of vectors (Amersham Biosciences, Piscataway, N.J.). In certain embodiments, the recombinant expression vector is transformed into bacteria, such as *E. coli*. In certain embodiments, the expression of the nucleic acid binding polypeptide is induced by culturing the bacteria under certain growth conditions. For example, in certain embodiments, expression of the nucleic acid binding polypeptide is induced by addition of isopropylthio-β-galactoside (IPTG) to the culture medium.

In various embodiments of expression vectors, a polynucleotide encoding a tag, such as an affinity tag, is expressed in frame with a polynucleotide encoding a nucleic acid binding polypeptide. In certain embodiments, certain such tags can provide a mechanism for detection or purification of the nucleic acid binding polypeptide. Examples of tags include, but are not limited to, polyhistidine tags, which allow purification using nickel chelating resin, and glutathione S-transferase moieties, which allow purification using glutathione-based chromatography. In certain embodiments, an expression vector further provides a cleavage site between the tag and the nucleic acid binding polypeptide, so that the nucleic acid binding polypeptide may be cleaved from the tag following purification. In certain embodiments, e.g., embodiments using polyhistidine tags, the nucleic acid binding polypeptide is not cleaved from the tag. It has been reported that the presence of a polyhistidine tag on a recombinant DNA binding protein may enhance the interaction of the DNA binding protein with DNA. See, e.g., Buning et al (1996) *Anal. Biochem.* 234:227-230.

2. Fusion Proteins

In certain embodiments, fusion proteins are provided. In certain such embodiments, a fusion protein comprises any of the nucleic acid binding polypeptides described above joined to a nucleic acid modification enzyme. In certain such embodiments, the nucleic acid modification enzyme comprises a nucleic acid polymerase. In certain embodiments, the nucleic acid polymerase comprises a DNA polymerase.

a) Certain DNA Polymerases for Use in Fusion Proteins

Certain DNA polymerases are known to those skilled in the art. For example, DNA polymerases include DNA-dependent polymerases, which use DNA as a template, or RNA-dependent polymerases, such as reverse transcriptase, which use RNA as a template. Currently, DNA-dependent DNA polymerases fall into one of six families (A, B, C, D, X, and Y), with most falling into one of three families (A, B, and C). See, e.g., Ito et al. (1991) *Nuc. Acids. Research* 19:4045-4057; Braithwaite at al. (1993) *Nuc. Acids. Research* 21:787-802; Fileé et al. (2002) *J. Mol. Evol.* 54:763-773; and Albà (2001) *Genome Biol.* 2:3002.1-3002.4. Certain DNA polymerases may be single-chain polypeptides (e.g., certain family A and B polymerases) or multi-subunit enzymes (e.g., certain family C polymerases) with one of the subunits having polymerase activity. Id. In certain embodiments, a fusion protein comprises a DNA polymerase selected from a family A, B, C, D, X, or Y polymerase.

In certain embodiments, a fusion protein comprises a fragment or variant of an A, B, C, D, X, or Y polymerase having polymerase activity. In certain embodiments, a fusion protein comprises a family A DNA polymerase or a fragment or variant thereof having polymerase activity. In certain such embodiments, the family A polymerase is a bacterial family A polymerase, such as a polymerase from the genus *Bacillus*, *Thermus*, or *Thermotoga*. In certain such embodiments, the family A polymerase is Taq DNA polymerase (SEQ ID NO:32) or a fragment or variant thereof having polymerase activity. In certain embodiments, a fusion protein comprises a family B DNA polymerase or a fragment or variant thereof having polymerase activity. In certain such embodiments, the family B polymerase is an archaeal family B polymerase, such as a polymerase from the genus *Thermococcus* or *Pyrococcus*. In certain such embodiments, the family B polymerase is Pfu DNA polymerase (SEQ ID NO:31) or a fragment or variant thereof having polymerase activity.

In addition to polymerase activity, certain DNA polymerases also possess other activities, such as 3' to 5' exonuclease (proofreading) activity or 5' to 3' exonuclease activity. See, e.g., Fileé et al. (2002) *J. Mol. Evol.* 54:763-773; and Pavlov et al. (2004) *Trends in Biotech.* 22:253-260. In certain such DNA polymerases, polymerase activity and exonuclease activity are carried out by separate domains. The domain structure of certain DNA polymerases is known to those skilled in the art. See, e.g., id.; Albà (2001) *Genome Biol.* 2:3002.1-3002.4; and Steitz (1999) *J. Biol. Chem.* 274: 17395-17398.

In certain embodiments, a fusion protein comprises a "chimeric" DNA polymerase. In certain such embodiments, a chimeric DNA polymerase comprises a domain having polymerase activity from a particular DNA polymerase and a domain having exonuclease activity from a different DNA polymerase. See, e.g., U.S. Pat. Nos. 5,795,762 and 5,466,591.

In certain embodiments, a fusion protein comprises a DNA polymerase having both polymerase activity and exonuclease activity. In certain such embodiments, the exonuclease activity is 5' to 3' exonuclease activity. In certain such embodiments, the level of 5' to 3' exonuclease activity is reduced or eliminated relative to the level of 5' to 3' exonuclease activity of a native DNA polymerase. In certain such embodiments, mutation of a DNA polymerase results in reduction or elimination of 5' to 3' exonuclease activity. In certain such embodiments, one or more amino acid substitutions result in reduction or elimination of 5' to 3' exonuclease activity. Certain such substitutions are known to those skilled in the art. For example, substitution of a conserved glycine in certain thermostable DNA polymerases reduces or eliminates 5' to 3' exonuclease activity. See, e.g., U.S. Pat. Nos. 5,795,762 and 5,466,591 (describing the G46D substitution in Taq, Tth, and TZ05 DNA polymerases; the G43D substitution in Tsps17 DNA polymerase; and the G37D substitution in Tma and Taf DNA polymerases).

In certain embodiments, deletion of one or more amino acids from a DNA polymerase results in the reduction or elimination of 5' to 3' exonuclease activity. Certain such deletions are known to those skilled in the art. For example, certain N-terminal deletions of certain thermostable DNA polymerases reduce or eliminate 5' to 3' exonuclease activity. Exemplary N-terminal deletions include, but are not limited to, deletion of about the first 35-50 amino acid residues of a thermostable DNA polymerase. See, e.g., U.S. Pat. Nos. 5,795,762 and 5,466,591 (describing deletion of N-terminal amino acid residues up to and including the conserved glycine residues in Taq, Tth, TZ05, Tsps17, Tma, and Taf, described above). Exemplary N-terminal deletions further include, but are not limited to, deletion of about the first 70-80 amino acid residues of a thermostable DNA polymerase. See, e.g., U.S. Pat. Nos. 5,795,762 and 5,466,591 (describing deletion of N-terminal amino acid residues up to and including the following residues: Ala 77 (Taq DNA polymerase), Ala 78 (Tth DNA polymerase), Ala 78 (TZ05 DNA polymerase), Ala 74 (TSPS17 DNA polymerase), Leu 72 (Tma DNA polymerase), and Ile 73 (Taf DNA polymerase)). Exemplary N-terminal deletions further include, but are not limited to, deletion of the first 139 or the first 283 amino acid residues of Tma DNA polymerase. See, e.g., U.S. Pat. Nos. 5,795,762 and 5,466,591.

In certain embodiments, a fusion protein comprises a DNA polymerase that lacks an exonuclease domain. In certain such embodiments, the exonuclease domain is a 5' to 3' exonuclease domain. Exemplary DNA polymerases that lack a 5' to 3' exonuclease domain include, but are not limited to, the large ("Klenow") fragment of *E. coli* DNA polymerase I and the "Stoffel" fragment of Taq DNA polymerase, which lacks about the first 289-300 N-terminal amino acids of full-length Taq DNA polymerase. See Lawyer at al. (1989) *J. Biol. Chem.* 264:6427-6437 (describing a "Stoffel" fragment); Vainshtein et al. (1996) *Protein Science* 5:1785-1792.

In certain embodiments, a fusion protein comprises a DNA polymerase having one or more mutations that reduce the ability of the polymerase to discriminate against the incorporation of dideoxynucleotides. Certain exemplary mutations are described, for example, in U.S. Pat. No. 6,333,183; EP 0 745 676 B1; and U.S. Pat. No. 5,614,365. One such exemplary mutation is the F667Y mutation in Taq DNA polymerase. See, e.g., U.S. Pat. No. 5,614,365.

In certain embodiments, a fusion protein comprises a DNA polymerase having one or more mutations that reduce the ability of the polymerase to discriminate against the incorporation of fluorescently labeled nucleotides into polynucleotides. In certain embodiments, such "discrimination reduction" mutations occur within the nucleotide label interaction region of a DNA polymerase, which is described, for example, in U.S. Pat. No. 6,265,193. Exemplary discrimination reduction mutations are provided in U.S. Pat. No. 6,265, 193. In certain embodiments, a DNA polymerase further comprises one or more mutations in addition to one or more discrimination reduction mutations. In certain embodiments, such mutations include, but are not limited to, mutations that increase or decrease 3' to 5' exonuclease activity; increase or decrease 5' to 3' exonuclease activity; increase or decrease thermostability; increase or decrease processivity; and increase incorporation of dideoxynucleotides. In certain embodiments, a DNA polymerase comprises one or more discrimination reduction mutations and one or more mutations that decrease 3' to 5' exonuclease activity. In certain embodiments, a DNA polymerase comprises one or more discrimination reduction mutations and one or more mutations that increase incorporation of dideoxynucleotides. Such DNA polymerases are described, for example, in U.S. Pat. No. 6,265,193.

In certain, embodiments, a fusion protein comprises a thermostable DNA polymerase. In certain embodiments, a thermostable DNA polymerase is a naturally occurring thermostable DNA polymerase. In certain embodiments, a thermostable DNA polymerase is a fragment or variant of a naturally occurring thermostable DNA polymerase that possesses polymerase activity. Exemplary guidance for determining certain such fragments and variants is provided in Pavlov et al. (2004) *Trends in Biotech.* 22:253-260.

Certain exemplary thermostable DNA polymerases are known to those skilled in the art. See, e.g., Sambrook et al. (2001) *Molecular Cloning: A Laboratory Manual* ($3^{rd}$ ed., Cold Spring Harbor Laboratory Press, NY) at 8.10-8.11. Such thermostable DNA polymerases include, but are not limited to, DNA polymerases from the genus *Thermus, Thermococcus, Thermotoga, Bacillus,* and *Pyrococcus*. Certain exemplary thermostable DNA polymerases include, but are not limited to, DNA polymerases from *Thermus aquaticus* (e.g., Taq DNA polymerase), *Thermus brockianus* (e.g., Tbr polymerase), *Thermus flavus* (e.g., Tfl DNA polymerase), *Thermus caldophilus, Thermus filiformis, Thermus oshimai, Thermus thermophilus* (e.g., Tth DNA polymerase), and *Thermus ubiquitus*. Certain other thermostable DNA polymerases from *Thermus* include, but are not limited to, Tsps17 and TZ05. Certain fragments and variants of Taq, Tfl, Tth, Tsps17, and TZ05 DNA polymerases are known to those skilled in the art. See, e.g., Vainshtein et al. (1996) *Protein Science* 5:1785-1792 (discussing the Taq Stoffel fragment), EP 0 745 676 B1, WO 01/14568, US 2004/0005573 A1, U.S. Pat. No. 5,795,762, and U.S. Pat. No. 5,466,591.

In certain embodiments, a thermostable DNA polymerase comprises a DNA polymerase from *Thermococcus litoralis* (e.g., Tli polymerase), *Thermococcus kodakarensis* KOD1 (e.g., KOD DNA polymerase), or *Thermococcus gorgonarius* (e.g., Tgo DNA polymerase). Certain fragments and variants of KOD DNA polymerase are known to those skilled in the art. See, e.g., EP 1 154 017 A1. In certain embodiments, a thermostable DNA polymerase comprises a DNA polymerase from *Thermotoga neapolitana* (e.g., Tne DNA polymerase) or *Thermotoga maritima* (e.g., Tma DNA polymerase). See, e.g., US 2003/0092018 A1 and US 2003/0162201 A1. In certain embodiments, a thermostable DNA polymerase comprises a DNA polymerase from *Thermosipho africanus* (e.g., Taf DNA polymerase). Certain fragments and variants of Tma, Taf, and Tne DNA polymerases are known to those skilled in the art. See, e.g., US 2003/0092018 A1, US 2003/0162201 A1, U.S. Pat. No. 5,795,762; and U.S. Pat. No. 5,466,591.

Certain exemplary thermostable DNA polymerases include, but are not limited to, DNA polymerases from *Pyrococcus furiosus* (e.g., Pfu DNA polymerase), *Pyrococcus woesei* (e.g., Pwo polymerase), *Pyrococcus* spp. GB-D, and *Pyrolobus fumarius*. See, e.g., U.S. Pat. No. 6,489,150 B1, U.S. Pat. No. 6,673,585 B1, U.S. Pat. No. 5,948,666, U.S. Pat. No. 6,492,511, and EP 0 547 359 B1. Certain fragments and variants of Pfu polymerase are known to those skilled in the art. See, e.g., U.S. Pat. No. 6,333,183 B1. In certain embodiments, a thermostable DNA polymerase comprises a DNA polymerase from *Bacillus stearothermophilus* or a variant or fragment thereof, such as the "large fragment" of Bst DNA polymerase. In certain embodiments, a thermostable DNA polymerase comprises a DNA polymerase from the thermophilic bacterium designated Tsp JS1. See, e.g., US 2004/0005573 A1. Certain fragments and variants of a thermostable DNA polymerase from Tsp JS1 are known to those skilled in the art. Id.

b) Certain Recombinant Methods for Making Fusion Proteins

In various embodiments, a fusion protein comprising a nucleic acid binding polypeptide and a nucleic acid modification enzyme is produced using recombinant methods. In certain embodiments, a polynucleotide encoding a nucleic acid binding polypeptide and a polynucleotide encoding a nucleic acid modification enzyme are ligated together in the same reading frame, resulting in a polynucleotide encoding a fusion protein.

In certain embodiments, a polynucleotide encoding a nucleic acid binding polypeptide is obtained as described in Part IV: C.1 above.

In certain embodiments, a polynucleotide encoding a nucleic acid modification enzyme is obtained by the polymerase chain reaction (PCR). Certain methods employing PCR are known to those skilled in the art. In certain embodiments, a polynucleotide comprising all or a portion of the coding sequence of a nucleic acid modification enzyme is amplified using appropriate primers. In certain embodiments, restriction enzyme sites are included in the primers to facilitate cloning of the amplification product into an appropriate expression vector. In certain embodiments, the polynucleotide encoding a nucleic acid modification enzyme is a polynucleotide encoding a DNA polymerase. Polynucleotide sequences encoding certain DNA polymerases are known to those skilled in the art. See, e.g., Ito et al. (1991) *Nuc. Acids. Research* 19:4045-4057; Braithwaite et al. (1993) *Nuc. Acids. Research* 21:787-802; and Fileé et al. (2002) *J. Mol. Evol.* 54:763-773. In certain embodiments, the polynucleotide encoding a DNA polymerase is a polynucleotide encoding Taq DNA polymerase or a fragment or variant thereof having polymerase activity. In certain embodiments, the polynucleotide encoding a DNA polymerase is a polynucleotide encoding Pfu DNA polymerase or a fragment or variant thereof having polymerase activity.

In various embodiments, a polynucleotide encoding a fusion protein is cloned into a suitable vector. In certain such embodiments, the vector is transferred (e.g., transformed or transfected) into a suitable host cell. In certain embodiments, a polynucleotide encoding a fusion protein is cloned into an expression vector and, in certain embodiments, expressed in a suitable host cell. Certain exemplary expression vectors and host cells are known to those skilled in the art, as described in Part IV.C.1 above. In certain embodiments, the fusion protein is isolated from the host cell.

In certain embodiments of a fusion protein, a nucleic acid binding polypeptide is joined to the N-terminus of a nucleic acid modification enzyme. In certain embodiments of a fusion protein, a nucleic acid binding polypeptide is joined to the C-terminus of a nucleic acid modification enzyme. In certain embodiments of a fusion protein, a nucleic acid binding polypeptide is disposed internally within a nucleic acid modification enzyme.

In certain embodiments of a fusion protein, a nucleic acid binding polypeptide is joined to the N-terminus of a DNA polymerase. In certain embodiments, of a fusion protein, a nucleic acid binding polypeptide is joined to the C-terminus of a DNA polymerase. In certain embodiments of a fusion protein, a nucleic acid binding polypeptide is disposed internally within a DNA polymerase. Certain three dimensional structures of certain DNA polymerases are known to those skilled in the art. See, e.g. Steitz (1999) *J. Biol. Chem.* 274: 17395-17398; Albà (2001) *Genome Biol.* 2:3002.1-3002.4. Certain DNA polymerases typically have a "hand-like" three dimensional structure comprising "finger," "palm," and "thumb" domains. See, e.g., Steitz (1999) *J. Biol. Chem.* 274:17395-17398; Albà (2001) *Genome Biol.* 2:3002.1-3002.4. In certain embodiments of a fusion protein, wherein a nucleic acid binding polypeptide is disposed internally within a DNA polymerase, the nucleic acid binding polypeptide occurs within a loop in the "thumb" domain of the DNA polymerase. See, e.g., U.S. Pat. No. 5,972,603, e.g., FIG. 4.

In certain embodiments, one skilled in the art can routinely determine whether a DNA polymerase retains polymerase activity in the context of a fusion protein by assaying the fusion protein for polymerase activity.

c) Certain Other Methods for Making Fusion Proteins

In certain embodiments, a nucleic acid binding polypeptide is joined to a nucleic acid modification enzyme by chemical methods. In certain such embodiments, the nucleic acid modification enzyme is a DNA polymerase. In certain embodiments, a nucleic acid binding polypeptide is joined to a nucleic acid modification enzyme by a chemical coupling agent. Certain such methods are known to those skilled in the art. See, e.g., Hermanson, ed., *Bioconjugate Techniques* (Academic Press 1996).

d) Certain Linkers

In certain embodiments, a nucleic acid binding polypeptide is joined to a nucleic acid modification enzyme by a linker. In certain embodiments, a linker is a peptide, which is joined by peptide bonds to a nucleic acid binding polypeptide and to a nucleic acid modification enzyme. In certain embodiments, a linker is engineered into a fusion protein by standard recombinant methods. For example, in certain embodiments, a polynucleotide encoding a fusion protein is constructed, wherein a polynucleotide encoding a linker is in frame with and disposed between a polynucleotide encoding a nucleic acid modification enzyme and a polynucleotide encoding a nucleic acid binding polypeptide.

In certain embodiments, a linker is any whole number of amino acids less than or equal to 25. In certain embodiments, a linker does not form an α-helix or β-strand. In certain such embodiments, a linker forms an extended, or "loop," conformation. In certain embodiments, a linker sequence comprises one or more glycine residues. In certain embodiments, a suitable linker sequence is determined using the LINKER program. See, e.g., Crasto et al. (2000) *Protein Eng.* 13:309-312.

Other exemplary linkers include, but are not limited to, carbohydrate linkers, lipid linkers, fatty acid linkers, and polymeric linkers. Exemplary polymeric linkers include, but are not limited to, polyether linkers, such as polyethylene glycol (PEG).

D. Certain Exemplary Methods Using Nucleic Acid Binding Polypeptides

1. Stabilize Nucleic Acid Duplexes

In certain embodiments, one or more nucleic acid binding polypeptides are used to stabilize a nucleic acid duplex from denaturation at temperatures above the Tm of the nucleic acid duplex, thereby effectively increasing the Tm of the nucleic acid duplex. In certain such embodiments, one or more nucleic acid binding polypeptides are combined with a nucleic acid duplex. In certain such embodiments, the ratio of the concentration of a nucleic acid binding polypeptide to the concentration of the nucleic acid duplex (in nucleotides) is at least about 1:25, 1:10, 1:5, 1:3, 1:1, or any ratio wherein the concentration of the nucleic acid binding polypeptide exceeds that of the nucleic acid duplex.

2. Anneal Complementary Nucleic Acid Strands

In certain embodiments, one or more nucleic acid binding polypeptides are used to promote the annealing of complementary nucleic acid strands. In certain embodiments, annealing takes place with greater rapidity and specificity in the presence of a nucleic acid binding polypeptide than in the absence of a nucleic acid binding polypeptide. In certain embodiments, complementary nucleic acid strands are allowed to anneal in a composition comprising one or more nucleic acid binding polypeptides. In certain such embodiments, a nucleic acid binding polypeptide is present at any concentration from about 1 µg/ml to about 500 µg/ml. In certain embodiments, one or more nucleic acid binding polypeptides are used to favor the annealing of nucleic acid strands that are complementary without mismatches over the annealing of nucleic acid strands that are complementary with mismatches.

In certain embodiments, nucleic acid binding polypeptides are used in hybridization-based detection assays or primer extension assays in which a probe or primer is annealed to a target nucleic acid sequence. Certain examples of the use of nucleic acid binding polypeptides in certain such assays are provided below.

a) Hybridization-Based Detection Assays

In certain embodiments, one or more nucleic acid binding polypeptides are used to increase the efficiency, e.g., the speed and specificity, of a hybridization-based detection assay. Exemplary hybridization-based detection assays include, but, are not limited to, assays in which target nucleic acid is immobilized on a solid support and exposed to a labeled probe (see, e.g., Sambrook et al. (2001) *Molecular Cloning: A Laboratory Manual* (3$^{rd}$ ed., Cold Spring Harbor Laboratory Press, NY), e.g., at 6.33-6.58 (describing "Southern" hybridizations). In certain embodiments, exemplary hybridization-based detection assays include microarray-based assays in which target nucleic acid is labeled and exposed to a plurality of polynucleotides immobilized on a solid support. See id. Appendix 10. An example of the use of the nucleic acid binding polypeptide Sso7d in a microarray-based detection assay is described, e.g., in Hatakeyama, US 2003/0022162 A1.

In certain hybridization-based detection assays, a nucleic acid probe is exposed to a mixture of nucleic acids. Within that mixture is a target nucleic acid, which, comprises a sequence that is complementary to the probe. The probe specifically anneals to the target nucleic acid to form a hybridization complex under certain conditions, e.g., conditions in which the probe is exposed to the target nucleic acid for an appropriate length of time and at an annealing temperature below that of the predicted Tm of the probe.

In certain embodiments, one or more nucleic acid binding polypeptides are used to increase the Tm of a probe, thereby increasing the temperature at which the annealing may be carried out. In certain such embodiments, the annealing is carried out in the presence of one or more nucleic acid binding polypeptides. In certain such embodiments, the annealing takes place at any temperature from 10° C. below to 40° C. above the predicted Tm of the probe. In certain such embodiments, the annealing takes place at a temperature up to 40° C. above the predicted Tm of the probe. In certain embodiments in which a probe is an oligonucleotide of about 15-35 nucleotides, annealing takes place in the presence of one or more nucleic acid binding polypeptides at any temperature between 40° C. and 85° C.

In certain embodiments, one or more nucleic acid binding polypeptides are used to increase the Tm of a probe, thereby allowing the use of shorter probes. In certain such embodiments, the annealing is carried out in the presence of one or more nucleic acid binding polypeptides. In certain such embodiments, a probe is of any length between 12 and 25 nucleotides. In certain such embodiments, a probe is of any length between 12 and 19 nucleotides. In certain such embodiments, a probe is of any length between 12 and 16 nucleotides.

In certain embodiments, one or more nucleic acid binding polypeptides are used to decrease the duration of time to achieve annealing. In certain such embodiments, the annealing is carried out in the presence of one or more nucleic acid binding polypeptides. In certain such embodiments, the annealing takes place over any amount of time from about 0.5 minute to about three hours. In certain such embodiments, the annealing takes place over any amount of time from about 1 minute to about 30 minutes. In certain such embodiments, the annealing takes place over any amount of time from about 1 minute to about 15 minutes.

In certain embodiments of hybridization-based detection assays, a probe may selectively hybridize to a target nucleic acid that is complementary without mismatches to the probe. In certain embodiments, a probe may also selectively hybridize to a target nucleic acid that is complementary to the probe but that contains one or more mismatches relative to the probe. In certain embodiments, one or more nucleic acid binding polypeptides are used to favor the hybridization of a probe to a target nucleic acid that is complementary without mismatches to the probe over the hybridization of a probe to a target nucleic acid that is complementary but that contains one or more mismatches relative to the probe. Thus, in certain embodiments, the specificity of hybridization is increased. In certain such embodiments, annealing is carried out under any of the conditions of time or temperature described above. In certain such embodiments, annealing is carried out at a temperature greater than the predicted Tm of the probe.

In certain embodiments, because nucleic acid binding polypeptides can substantially increase the speed and specificity of a hybridization-based detection assay, such polypeptides can be used in certain hybridization-based "point-of-use" devices. Point-of-use devices are typically portable devices that allow rapid diagnosis or detection of a physiological or pathological condition, in certain instances, in a non-clinical or small-scale laboratory setting. An exemplary point-of-use device is, for example, a typical pregnancy test. An exemplary point-of-use device that uses hybridization-based detection is, for example, the Affirm VPIII Microbial Identification System (Becton Dickinson and Company—BD Diagnostics, Sparks, Md.), whereby the presence of certain vaginal pathogens is detected in vaginal swab specimens using an oligonucleotide hybridization assay. See Briselden et al. (1994) *J. Clin. Microbiol.* 32:148-52; Witt et al. (2002) *J. Clin. Microbiol.* 40:3057-3059.

In certain embodiments, one or more nucleic acid binding polypeptides can be used in a hybridization-based point-of-use device that diagnoses a pathological condition, such as an infection, by detecting genetic material from a pathogen in a biological sample from a host. In certain embodiments, the volume of a biological sample to be used with a point-of-use device is reduced in the presence of one or more nucleic acid binding polypeptides. In certain embodiments, the hybridization-based point-of-use device utilizes microarray technology.

In certain embodiments, because nucleic acid binding polypeptides can substantially increase the specificity of a hybridization-based detection assay, one or more nucleic acid binding polypeptides can be used in assays that detect mutations or polymorphisms in a target polynucleotide. For example, one or more nucleic acid binding polypeptides can be used in assays that detect single nucleotide polymorphisms (SNPs). For a review of SNP detection methods, see., e.g., Shi (2001) *Clinical Chem.* 47:164-172. In certain embodiments, one or more nucleic acid binding polypeptides are used in assays that detect rare copies of a target polynucleotide in a complex mixture of nucleic acids. For example, in certain such embodiments, the target polynucleotide comprises genetic material from a pathogen contained within a biological sample from a host.

b) Increase Tm of Primers in Primer Extension Reactions

In certain embodiments, one or more nucleic acid binding polypeptides are used to increase the Tm of a primer in a primer extension reaction. In certain primer extension reactions, such as PCR, one or more primers are annealed to a template nucleic acid. In PCR, e.g., the annealing typically takes place over 30 seconds at about 55° C., a temperature that is less than the predicted Tm of a typical primer of about 20-30 nucleotides. Sambrook et al. (2001) *Molecular Cloning: A Laboratory Manual* (3$^{rd}$ ed., Cold Spring Harbor Laboratory Press, NY) at 8.22.

In certain embodiments, one or more nucleic acid binding polypeptides are used to increase the Tm of a primer in a primer extension reaction, thereby increasing the temperature at which the annealing may be carried out. In certain such embodiments, the annealing is carried out in the presence of one or more nucleic acid binding polypeptides. In certain such embodiments, the annealing is carried out at any temperature from about 55° C. up to about 75° C. In certain such embodiments, the annealing is carried out at any temperature between 60° C. and 70° C. In certain embodiments, increased annealing temperature reduces certain primer artifacts, such as primer dimmers and hairpin formation.

In certain embodiments, one or more nucleic acid binding polypeptides are used to increase the Tm of a primer in a primer extension reaction, thereby allowing the use of shorter primers. In certain such embodiments, the annealing is carried out in the presence of one or more nucleic acid binding polypeptides. In certain such embodiments, a primer is of any length between 12 and 19 nucleotides. In certain such embodiments, a primer is of any length between 12 and 16 nucleotides.

3. Enhance Activity of Nucleic Acid Modification Enzymes

In certain embodiments, one or more nucleic acid binding polypeptides are used to enhance the activity of a nucleic acid modification enzyme. In certain such embodiments, one or more nucleic acid binding polypeptides are included in a composition comprising a nucleic acid modification enzyme and a nucleic acid, thus enhancing the activity of the nucleic acid modification enzyme. In various embodiments, the enhancement in the activity of a nucleic acid modification enzyme is demonstrated by comparing the activity of the nucleic acid modification enzyme in the presence of one or more nucleic acid binding polypeptides with its activity in the absence of one or more nucleic acid binding polypeptides. In certain embodiments, the following assays may be used to evaluate the activity of a nucleic acid modification enzyme:

In certain embodiments, the activity of a gyrase or topoisomerase is assessed by determining the change in the supercoiled state of a nucleic acid exposed to the gyrase or topoisomerase in the presence and in the absence of one or more nucleic acid binding polypeptides.

In certain embodiments, the activity of a nuclease is assessed by determining the amount of cleavage product produced by the nuclease in the presence and in the absence of one or more nucleic acid binding polypeptides. In certain such embodiments, the activity of a restriction endonuclease is assessed by exposing a nucleic acid to a restriction endonuclease in the presence and in the absence of one or more nucleic acid binding polypeptides. In certain such embodiments, the extent of digestion by the restriction endonuclease is determined by gel electrophoresis.

In certain embodiments, the activity of a methylase is determined by assessing the methylation state of a nucleic acid exposed to a methylase in the presence and in the absence of one or more nucleic acid binding polypeptides. In certain such embodiments, the methylation state of the nucleic acid is assessed, for example, by determining the extent to which the nucleic acid is cleaved by a methylation sensitive restriction endonuclease, such as MboI.

In certain embodiments, the activity of a ligase is assessed by determining the amount of ligation product produced by the ligase in the presence and in the absence of one or more nucleic acid binding polypeptides. In certain such embodiments, a circularized plasmid is linearized by a restriction endonuclease, isolated from the restriction endonuclease, and exposed to ligase in the presence and in the absence of one or more nucleic acid binding polypeptides. In certain such embodiments, the ligation reaction mixture is used to transform competent bacteria. In certain such embodiments, the number of transformants is proportional to the activity of the ligase.

In certain embodiments, the activity of a polymerase is assessed in the presence and in the absence of one or more nucleic acid binding polypeptides using the polymerase activity assay described above in Part IV.A.

4. Increase Processivity of a DNA Polymerase

In certain embodiments, one or more nucleic acid binding polypeptides are used to improve the performance of DNA polymerase. In certain such embodiments, improved performance of DNA polymerase is increased processivity of the DNA polymerase in a primer extension reaction. In certain embodiments, the primer extension reaction is PCR. For example, in certain embodiments, the inclusion of one or more nucleic acid binding polypeptides in a PCR reaction allows for more efficient amplification of targets under suboptimal conditions, such as high salt concentrations. Examples of certain high salt concentrations include from 60 mM KCl to 130 mM KCl for Taq DNA polymerase, and from 40 mM KCl to 130 mM KCl for Pfu polymerase. In certain embodiments, the inclusion of one or more nucleic acid binding polypeptides in a PCR reaction decreases the time of the extension step of PCR to, for example, minutes, ≤3 minutes, ≤2 minutes, ≤1 minute, or ≤30 seconds. In certain embodiments, the inclusion of one or more nucleic acid binding polypeptides in a PCR reaction allows for more efficient amplification of long targets, for example, targets from about 5 kb to about 20 kb.

E. Certain Methods Using Fusion Proteins

In certain embodiments, a fusion protein comprising a nucleic acid binding polypeptide and a nucleic acid modification enzyme is used in any method that uses a nucleic acid binding polypeptide (as described, for example, in Part IV.D. above), except that the fusion protein replaces the nucleic acid binding polypeptide in the method. In certain embodiments, a fusion protein comprising a nucleic acid binding polypeptide and a nucleic acid modification enzyme is used in any method that uses a nucleic acid binding polypeptide (as described, for example, in Part IV.D. above), except that the fusion protein is used in combination with the nucleic acid binding polypeptide in the method.

In certain embodiments, a fusion protein comprising a nucleic acid binding polypeptide and a nucleic acid modification enzyme is used in any reaction in which the nucleic acid modification enzyme alone can be used. In certain embodiments, a fusion protein comprising a nucleic acid binding polypeptide and a nucleic acid modification enzyme is used to improve the efficiency of any reaction in which the nucleic acid modification enzyme alone can be used. In certain such embodiments, a fusion protein comprising a nucleic acid binding polypeptide and a nucleic acid modification enzyme has increased activity relative to the nucleic acid modification enzyme alone. In certain such embodiments, the assays set forth in Part IV.D.3 above may be used to evaluate the activity of a nucleic acid modification enzyme or a fusion protein comprising a nucleic acid binding polypeptide and a nucleic acid modification enzyme. In certain embodiments, a fusion protein comprising a nucleic acid binding polypeptide and a DNA polymerase has increased processivity relative to the DNA polymerase alone.

In certain embodiments, a fusion protein comprising a nucleic acid binding polypeptide and a DNA polymerase is used in a primer extension reaction. In certain such embodiments, the fusion protein increases the efficiency of the primer extension reaction. In certain embodiments, a fusion protein comprising a nucleic acid binding polypeptide and a DNA polymerase is included in a primer extension reaction to increase the Tm of one or more primers in the reaction. In certain embodiments, the temperature at which annealing is carried out may be increased. In certain embodiments, shorter primers may be used.

In certain embodiments, a fusion protein comprising a nucleic acid binding polypeptide and a thermostable DNA polymerase is included in a PCR reaction. In certain such embodiments, the fusion protein increases the efficiency of PCR. In certain embodiments, a fusion protein comprising a nucleic acid binding polypeptide and a thermostable DNA polymerase is included in a PCR reaction that is conducted under suboptimal conditions, such as high salt concentrations. Exemplary high salt concentrations are described above in Part IV.D.4. In certain embodiments, a fusion protein comprising a nucleic acid binding polypeptide and a thermostable DNA polymerase is included in a PCR reaction to decrease the time of the extension step of PCR. Exemplary extension times are provided above in Part IV.D.4. In certain embodiments, a fusion protein comprising a nucleic acid binding polypeptide and a thermostable DNA polymerase is included in a PCR reaction to more efficiently amplify long targets. Exemplary target lengths are provided above in Part IV.D.4. In certain embodiments, a fusion protein comprising a nucleic acid binding polypeptide and a thermostable DNA polymerase is included in a PCR reaction to increase the amount of PCR amplification product.

In certain embodiments, a fusion protein comprising a nucleic acid binding polypeptide and a thermostable DNA polymerase is used in "hot start" PCR. In certain embodiments, "hot start" PCR is used to suppress non-specific binding of primer to template. See, e.g., Sambrook et al. (2001) *Molecular Cloning: A Laboratory Manual* (3$^{rd}$ ed., Cold Spring Harbor Laboratory Press, NY) at 8.110 (describing "hot start" PCR). In certain embodiments of "hot start" PCR, one or more components to be used in a PCR are prevented from functioning in the PCR until the reaction mixture reaches or exceeds a temperature at which non-specific priming does not occur. Id. For example, in certain embodiments of "hot start" PCR, an antibody to the thermostable DNA polymerase is used to reversibly block polymerase activity until a suitable temperature is reached. See, e.g., Kellogg et al. (1994) *Biotechniques* 16:1134-1137 (describing the use of antibodies to Taq DNA polymerase). In certain embodiments, a fusion protein comprising a nucleic acid binding polypeptide and a thermostable DNA polymerase is used in "hot start" PCR. In certain such embodiments, an antibody to the nucleic acid binding polypeptide is used to reversibly block nucleic acid binding activity and/or polymerase activity until a suitable temperature is reached.

F. Certain Kits

In various embodiments, kits are provided. In certain embodiments, a kit comprises any one or more of the nucleic acid binding polypeptides described above. In certain embodiments, a kit further comprises a nucleic acid modification enzyme. In certain such embodiments the nucleic acid modification enzyme is a DNA polymerase. In certain such embodiments, the DNA polymerase is a thermostable DNA polymerase. In certain embodiments, a kit further comprises deoxynucleotides. In certain embodiments, a kit further comprises dideoxynucleotides.

In certain embodiments, a kit comprises any one or more of the fusion proteins described above. In certain such embodiments, the fusion protein comprises a nucleic acid binding polypeptide and a DNA polymerase. In certain such embodiments, the DNA polymerase is a thermostable DNA polymerase. In certain embodiments, a kit further comprises deoxynucleotides. In certain embodiments, a kit further comprises dideoxynucleotides.

V. EXAMPLES

A. Cloning and Expression of Polynucleotides Encoding Nucleic Acid Binding Polypeptides A polynucleotide encoding SEQ ID NO:1 was constructed by ligating the following oligonucleotides (SEQ ID NOs:8-10) end-to-end, such that the 5' end of SEQ ID NO:9 was ligated to the 3' end of SEQ ID NO:8, and the 5' end of SEQ ID NO:10 was ligated to the 3' end of SEQ ID NO:9.

```
                                        SEQ ID NO: 8
5' atgtccaaga agcagaaact Gaagttctac gacatTaagg cgaagcaggc gtttgag 3'
                                        SEQ ID NO: 9
5' acCgaccagt acgaggttat tgagaagcag acCgcccgcg gtccgatgat gttcgcc 3'
                                        SEQ ID NO: 10
5' gtggccaaat cgccgtacac cggcatTaaa gtGtacCgCc tgttaggcaa gaagaaataa 3'
```

The capital letters in SEQ ID NOs:8-10 represent changes from the naturally occurring PAE3192 sequence (SEQ ID NO:2). Those changes were made to generate codons more favorable for the expression of SEQ ID NO:1 in *E. coli*. Those changes do not result in any alterations in the amino acid sequence of SEQ ID NO:1.

To ligate SEQ ID NOs:8-10 together, the following oligonucleotides (SEQ ID NOS:11-12) were first annealed to SEQ 10 NOs:8-10 as discussed below.

```
                                        SEQ ID NO: 11
     5' gtactggtcg gtctcaaacg cctg 3'
                                        SEQ ID NO: 12
     5' cgatttggcc acggcgaaca tcat 3'
```

SEQ ID NO:11 is complementary to the 3' end of SEQ ID NO:8 and the 5' end of SEQ ID NO:9. Thus, the annealing of SEQ ID NO:11 to SEQ ID NOs:8-9 created a region of double stranded DNA where SEQ ID NO:11 spans the junction of SEQ ID NOS:8-9. This region of double stranded DNA was a suitable substrate for DNA ligase. Likewise, SEQ ID NO:12 is complementary to the 3' end of SEQ ID NO:9 and the 5' end of SEQ ID NO:10. Thus, the annealing of SEQ ID NO:12 to SEQ ID NOS:9-10 created a region of double stranded DNA where SEQ ID NO:12 spans the junction of SEQ ID NOS:9-10.

SEQ 10 NOs:8-10 were then ligated. The resulting polynucleotide (SEQ ID NO:13) was amplified by PCR.

A polynucleotide encoding SEQ ID NO:6 was constructed by ligating the following oligonucleotides (SEQ ID NOs:14-16) end-to-end:

```
                                        SEQ ID NO: 14
5' atgccGaaga aggagaagat Taagttcttc gacctGgtcg ccaagaagta ctacgag 3'
                                        SEQ ID NO: 15
5' actgacaact acgaagtcga gatTaaggag actaagCgCg gcaagtttCg Cttcgcc 3'
                                        SEQ ID NO: 16
5' aaagccaaga gcccgtacac cggcaagatc ttctatCgCg tgctGggcaa agcctag 3'
```

The capital letters represent changes from the naturally occurring APE3192 sequence (SEQ ID NO:7). Those changes were made to generate codons more favorable for the expression of SEQ ID NO:6 in *E. coli*. Those changes do not result in any alterations in the amino acid sequence of SEQ ID NO:6.

The following oligonucleotides (SEQ ID NOs:17-18) were annealed to SEQ ID NOs:14-16 to create regions of double stranded DNA spanning the junctions between SEQ ID NOs:14-15 and SEQ ID NOs:15-16.

```
                                        SEQ ID NO: 17
     5' gtagttgtca gtctcgtagt actt 3'
                                        SEQ ID NO: 18
     5' gctcttggct tggcgaagc gaaa 3'
```

SEQ ID NOs:14-16 were then ligated. The resulting polynucleotide (SEQ ID NO:19) was amplified by PCR.

SEQ ID NO:13 was cloned into the pET16b vector (Novagen, Milwaukee, Wis.) using standard recombinant methods. That vector allows expression of the cloned sequences from the inducible T7 promoter. It also includes sequences encoding polyhistidine (10×His) (SEQ ID NO: 48) followed by a Factor Xa cleavage site upstream of the cloning site. Thus, the encoded proteins are tagged at their N-termini with a polyhistidine moiety. Recombinant vector comprising SEQ ID NO:13 was transformed into competent *E. coli* host cells using standard methods.

SEQ ID NO:19 was also cloned into the pET16b vector using standard recombinant methods. Recombinant vector comprising SEQ ID NO:19 was transformed into competent *E. coli* host cells using standard methods.

Host cells containing a recombinant vector comprising SEQ ID NO:13 are induced to express a tagged polypeptide comprising SEQ ID NO:1 by adding IPTG to the media in which the host cells are grown. The tagged polypeptide is isolated from the host cells by affinity chromatography using nickel-NTA resin. In certain embodiments, the polyhistidine tag is removed from the isolated polypeptide by treatment with Factor Xa.

Host cells containing a recombinant vector comprising SEQ ID NO:19 are induced to express a tagged polypeptide comprising SEQ ID NO:6 by adding IPTG to the media in which the host cells are grown. The tagged polypeptide is isolated from the host cells by affinity chromatography using nickel-NTA resin. In certain embodiments, the polyhistidine tag is removed from the isolated polypeptide by treatment with Factor Xa.

B. Use of Nucleic Acid Binding Polypeptides to Stabilize a DNA Duplex from Thermal Denaturation The ability of a nucleic acid binding polypeptide to stabilize a DNA duplex from thermal denaturation is demonstrated by the following assay, which measures the increase in the Tm of a nucleic acid in the presence of a nucleic acid binding polypeptide. See, e.g., Baumann et al. (1994) *Nature Struct. Biol.* 1:808-819; and McAfee et al. (1995) *Biochem.* 34:10063-10077. Poly(dI-dC) at a concentration of about 70 µM (in nucleotides) is combined with a nucleic acid binding polypeptide at a concentration of about 350 µM in 5 mM Tris.Cl (pH 7.0). Poly(dI-dC) at a concentration of about 70 µM (in nucleotides) in 5 mM Tris.Cl (pH 7.0) without a nucleic acid binding polypeptide is used as a negative control. The absorbance of the poly(dI-dC) with and without a nucleic acid binding polypeptide is measured at 260 nm as a function of temperature using a spectrophotometer. The temperature is increased in steps, and absorbance is measured at each step. For each step, the temperature is raised by 1° C. over 30 seconds, followed by a holding time of 60 seconds prior to the measuring of absorbance. A melting curve is generated based on the increase in absorbance as a function of temperature. The Tm (temperature at which 50% of the poly(dI-dC) is denatured) occurs at the inflection point of the melting curve. The Tm of poly(dI-dC) in the negative control is subtracted from the Tm of poly(dI-dC) in the presence of a nucleic acid binding polypeptide to determine the increase in Tm due to the presence of the nucleic acid binding polypeptide.

C. Use of Nucleic Acid Binding Polypeptides to Increase Processivity of a DNA Polymerase The ability of a nucleic acid binding polypeptide to increase the processivity of a DNA polymerase is assessed using a processivity assay based on that of Wang et al. (2004) *Nuc. Acids Res.* 32:1197-1207. A 5' FAM-labeled primer of sequence 5' gttttcccagtcacgacgttgtaaaacgacggcc 3' (SEQ ID NO:29) is added to single stranded M13mp18 DNA in a reaction composition comprising 10 mM Tris-HCl pH 8.8, 50 mM KCl, 2.5 mM MgCl$_2$, 250 µm dNTPs, and 0.1% Triton X-100. The concentrations of the primer and M13mp18 template are 50 nM and 80 nM, respectively. The primer is annealed to the single stranded M13mp18 DNA template by heating the mixture to 90° C. for 5 minutes, cooling to 72° C. at 0.1° C. per second, incubating at 72° C. for 10 minutes, and cooling to 4° C. at 0.1° C. per second. A thermostable DNA polymerase, such as Taq DNA polymerase, is added to the above reaction composition at a concentration of about 1:4000 (DNA polymerase:template).

Two parallel reactions are prepared. In one of the parallel reactions, a nucleic acid binding polypeptide is added to a final concentration of about 70 µg/ml in 20 µl of the above reaction composition. The second parallel reaction contains 20 µl of the above reaction composition with no added nucleic acid binding polypeptide.

DNA synthesis is initiated in the reaction compositions by incubating them at 72° C. Samples from each reaction are taken at various time points. The samples are diluted in gel loading dye, and the primer extension products in the samples are analyzed by denaturing polyacrylamide gel electrophoresis using an ABI 377 DNA Sequencer. The median product length is determined based on the integration of all detectable primer extension products. When the median product length does not change with an increase in reaction time or a decrease in polymerase concentration (to ensure that the template is in excess), that length is used as a measure of processivity.

D. Use of Nucleic Acid Binding Polypeptides to Increase the Efficiency (Speed and Specificity) of a Hybridization-Based Detection Assay 1. Annealing Assay The ability of a nucleic acid binding polypeptide to increase the specificity of a hybridization-based detection assay is measured using an annealing assay based on that of Guagliardi at al. (1997) *J. Mol. Biol.* 267:841-848. A first set of two reaction compositions is prepared as follows: In a first reaction composition, a single stranded M13mp18 circular DNA (0.05 pmol) is combined with an equal amount of $^{32}$P end-labeled oligonucleotide of sequence 5'-gtaaaacgacggc-cagt-3' (SEQ ID NO:20) in a buffered reaction mixture (20 mM Tris-HCl pH 7.5, 2 mM DTT, 5 mM MgCl$_2$, 100 µg/ml BSA). In a second reaction composition, single stranded M13mp18 circular DNA (0.05 pmol) is combined with an equal amount of $^{32}$P end-labeled oligonucleotide of sequence 5'-gtaaaacgtcggccagt-3' (SEQ ID NO:21) in a buffered reaction mixture (20 mM Tris-HCl pH 7.5, 2 mM DTT, 5 mM MgCl2, 100 µg/ml BSA). The nucleotide indicated in bold is a mismatch with respect to the M13mp18 DNA sequence. A nucleic acid binding polypeptide is added separately to both reaction compositions at a final concentration of about 5 µg/ml.

A second set of two reaction compositions is prepared. The second set is the same as the first set of reaction compositions, except that a nucleic acid binding polypeptide is not added to either the first or second reaction composition of the second set of reaction compositions. The final volume of each reaction composition is 10 µl.

The reaction compositions are incubated at 60° C. for three minutes. The reactions are stopped by adding 1% SDS in standard loading dye to each reaction composition. The reactions are analyzed by 1.5% agarose gel electrophoresis followed by autoradiography to visualize annealed product, which can be distinguished from unannealed probe by its slower mobility. Annealed product is quantified for each reaction using standard densitometric methods. An increase in the amount of annealed product in the first reaction compared to the second reaction is determined for both sets of reactions.

The ability of a nucleic acid binding polypeptide to increase the specificity of hybridization is demonstrated by a larger increase in the amount of annealed product for the first set of reactions compared to the second set of reactions.

2. Microarray-Based Assay

The ability of a nucleic acid binding polypeptide to increase the speed and specificity of a hybridization-based detection assay is also demonstrated by a decrease in the hybridization time (approximately 16 hours) required to perform a typical microarray-based detection assay. A typical microarray-based detection assay may be performed, for example, using the Mouse Genome Survey Microarray system (Applied Biosystems, Foster City, Calif.; P/N 4345065). That system includes reagents, hybridization controls, and reference nucleic acids that can be used to detect selective hybridization of a reference nucleic acid to a probe (i.e., a portion of a mouse cDNA) immobilized on a microarray. In an exemplary assay, a nucleic acid binding polypeptide is added to the hybridization solution at a concentration of about 50 to 250 µg/mL. The hybridization time is from about 1 to 30 minutes at a temperature of about 45° C. to 75° C. The arrays are washed, and hybridization is detected using the Chemiluminescence Detection Kit (Applied Biosystems, Foster City, Calif., P/N 4342142) according to the manufacturer's instructions. The arrays are analyzed using the Applied Biosystems 1700 Chemiluminescent Microarray Analyzer (Applied Biosystems, Foster City, Calif., P/N 4338036).

E. Construction and Expression of Fusion Proteins Comprising a Nucleic Acid Binding Polypeptide and a Thermostable DNA Polymerase 1. Fusion Proteins Comprising Pfu DNA Polymerase A fusion protein comprising SEQ ID NO:1 joined to the C-terminus of full length Pfu DNA polymerase was constructed as follows. An NdeI-XhoI restriction fragment comprising the coding sequence of full length Pfu DNA polymerase in frame with SEQ ID NO:13 was cloned into the NdeI and XhoI sites of the pET16b vector (Novagen, Milwaukee, Wis.) using standard recombinant methods. The resulting recombinant vector (pDS2r) encodes a fusion protein comprising SEQ ID NO:1 joined to the C-terminus of Pfu DNA polymerase by a Gly-Thr-Gly-Gly-Gly-Gly (SEQ ID NO: 49) peptide linker. A 10×His affinity tag (SEQ ID NO: 48) is present at the N-terminus of the fusion protein. The polynucleotide sequence encoding the fusion protein is shown in SEQ ID NO:22. The amino acid sequence of the fusion protein is shown in SEQ ID NO:23.

The recombinant vector pDS2r was transformed into competent E. coli host cells. Host cells comprising pDS2r were induced to express the fusion protein of SEQ ID NO:23 by adding IPTG to the media in which the host cells were grown. The fusion protein was isolated from the host cells by affinity chromatography using nickel-NTA resin.

In certain embodiments, the polyhistidine tag is removed from the fusion protein of SEQ ID NO:23 by treatment with Factor Xa to yield the fusion protein shown in SEQ ID NO:24.

A fusion protein comprising SEQ ID NO:6 joined to the C-terminus of full length Pfu DNA polymerase was constructed as follows: An NdeI-XhoI restriction fragment comprising the coding sequence of full length Pfu DNA polymerase in frame with SEQ ID NO:19 was cloned into the NdeI and XhoI sites of the pET16b vector using standard recombinant methods. The resulting recombinant vector (pDS1r) encodes a fusion protein comprising SEQ ID NO:6 joined to the C-terminus of Pfu DNA polymerase by a Gly-Thr-Gly-Gly-Gly-Gly (SEQ ID NO: 49) peptide linker. A 10×His affinity tag (SEQ ID NO: 48) is present at the N-terminus of the fusion protein. The polynucleotide sequence encoding the fusion protein is shown in SEQ ID NO:25. The amino acid sequence of the fusion protein is shown in SEQ ID NO:26.

The recombinant vector pDS1r was transformed into competent E. coli host cells. Host cells comprising pDS1r were induced to express the fusion protein of SEQ ID NO:26 by adding IPTG to the media in which the host cells were grown. The fusion protein was isolated from the host cells by affinity chromatography using nickel-NTA resin.

In certain embodiments, the polyhistidine tag is removed from the fusion protein of SEQ ID NO:26 by treatment with Factor Xa to yield the fusion protein shown in SEQ ID NO:27.

2. Fusion Proteins Comprising Taq DNA Polymerase

A fusion protein comprising SEQ ID NO:1 joined to the N-terminus of Taq DNA polymerase (SEQ ID NO:32 lacking the first two amino acid residues) was constructed as follows. SEQ ID NO:13 was cloned in frame at the 5' end of a polynucleotide encoding Taq DNA polymerase in the pET16b vector. The resulting recombinant vector (pDS17-7) encodes a fusion protein comprising SEQ ID NO:1 joined to the N-terminus of Taq DNA polymerase by a Gly-Gly-Val-Thr-Ser (SEQ ID NO: 50) peptide linker. A 10×His affinity tag (SEQ ID NO: 48) is present at the N-terminus of the fusion protein. The polynucleotide sequence encoding the fusion protein is shown in SEQ ID NO:33. The amino acid sequence of the fusion protein is shown in SEQ ID NO:34. The recombinant vector pDS17-7 was transformed into competent host cells.

Expression of the fusion protein is induced in the host cells using IPTG. The fusion protein is isolated from the host cells by affinity chromatography using nickel-NTA resin. In certain embodiments, the polyhistidine tag is removed from the fusion protein of SEQ ID NO:34 by treatment with Factor Xa to yield the fusion protein shown in SEQ ID NO:35.

A fusion protein comprising SEQ ID NO:6 joined to the N-terminus of Taq DNA polymerase (SEQ ID NO:32 lacking the first two amino acid residues) was constructed as follows. SEQ ID NO:19 was cloned in frame at the 5' end of a polynucleotide encoding Taq DNA polymerase in the pET16b vector. The resulting recombinant vector (pDS16-3) encodes a fusion protein comprising SEQ ID NO:6 joined to Taq DNA polymerase by a Gly-Gly-Val-Thr-Ser (SEQ ID NO: 50) peptide linker. A 10×His affinity tag (SEQ ID NO: 48) is present at the N-terminus of the fusion protein. The polynucleotide sequence encoding the fusion protein is shown in SEQ ID NO:36. The amino acid sequence of the fusion protein is shown in SEQ ID NO:37. The recombinant vector pDS16-3 was transformed into competent host cells.

Expression of the fusion protein is induced in the host cells using IPTG. The fusion protein is isolated from the host cells by affinity chromatography using nickel-NTA resin. In certain embodiments, the polyhistidine tag is removed from the fusion protein of SEQ ID NO:37 by treatment with Factor Xa to yield the fusion protein shown in SEQ ID NO:38.

A fusion protein comprising SEQ ID NO:1 joined to the N-terminus of a Stoffel fragment of Taq DNA polymerase (amino acid residues 291-832 of SEQ ID NO:32) was constructed as follows. SEQ ID NO:13 was cloned in frame at the 5' end of a polynucleotide encoding the Stoffel fragment in the pET16b vector. The resulting recombinant vector (pDS25-7) encodes a fusion protein comprising SEQ ID NO:1 joined to the N-terminus of the Stoffel fragment by a Gly-Gly-Val-Thr-Ser (SEQ ID NO: 50) peptide linker. A 10×His affinity tag (SEQ ID NO: 48) is present at the N-terminus of the fusion protein. The polynucleotide sequence encoding the fusion protein is shown in SEQ ID NO:39. The amino acid sequence of the fusion protein is shown in SEQ ID NO:40. The recombinant vector pDS25-7 was transformed into competent host cells.

Expression of the fusion protein is induced in the host cells using IPTG. The fusion protein is isolated from the host cells by affinity chromatography using nickel-NTA resin. In certain embodiments, the polyhistidine tag is removed from the fusion protein of SEQ ID NO:40 by treatment with Factor Xa to yield the fusion protein shown in SEQ ID NO:41.

A fusion protein comprising SEQ ID NO:6 joined to the N-terminus of a Stoffel fragment of Taq DNA polymerase (amino acid residues 291-832 of SEQ ID NO:32) was constructed as follows. SEQ ID NO:19 was cloned in frame at the 5' end of a polynucleotide encoding the Stoffel fragment in the pET16b vector. The resulting recombinant vector (pDS24-4) encodes a fusion protein comprising SEQ ID NO:6 joined to the N-terminus of the Stoffel fragment by a Gly-Gly-Val-Thr-Ser (SEQ ID NO: 50) peptide linker. A 10×His affinity tag (SEQ ID NO: 48) is present at the N-terminus of the fusion protein. The polynucleotide sequence encoding the fusion protein is shown in SEQ ID NO:42. The amino acid sequence of the fusion protein is shown in SEQ ID NO:43. The recombinant vector pDS24-4 was transformed into competent host cells.

Expression of the fusion protein is induced in the host cells using IPTG. The fusion protein is isolated from the host cells by affinity chromatography using nickel-NTA resin. In certain embodiments, the polyhistidine tag is removed from the fusion protein of SEQ ID NO:43 by treatment with Factor Xa to yield the fusion protein shown in SEQ ID NO:44.

F. Use of Fusion Proteins to Increase Processivity of Taq DNA Polymerase

The increase in processivity of a fusion protein comprising Taq DNA polymerase relative to Taq DNA polymerase alone is assessed using a processivity assay based on that of Wang et al. (2004) Nuc. Acids Res. 32:1197-1207. A 5' FAM-labeled primer of sequence 5' gttttcccagtcacgacgttgtaaaacgacggcc 3' (SEQ ID NO:29) is added to single stranded M13mp18 DNA in a mixture comprising 10 mM Tris-HCl pH 8.8, 50 mM KCl, 2.5 mM $MgCl_2$, 250 µm dNTPs, and 0.1% Triton X-100. The concentrations of the primer and M13mp18 template are 50 nM and 80 nM, respectively. The primer is annealed to the single stranded M13mp18 DNA template by heating the mixture to 96° C. for 5 minutes, cooling to 72° C. at 0.1° C. per second, incubating at 72° C. for 10 minutes, and cooling to 4° C. at 0.1° C. per second.

A reaction composition is prepared in which a fusion protein comprising Taq DNA polymerase is added at a molar concentration of about 1:4000 (fusion protein:template) to 20 µl of the above mixture. A control reaction composition is prepared in which Taq DNA polymerase is added at a molar concentration of about 1:4000 (DNA polymerase:template) to 20 µl of the above mixture. DNA synthesis is initiated in the reaction compositions by incubating them at 72° C. Samples from each reaction are taken at various time points. The samples are diluted in gel loading dye, and the primer extension products are analyzed by denaturing polyacrylamide gel electrophoresis using an ABI 377 DNA Sequencer. The median product length is determined based on the integration of all detectable primer extension products. When the median product length does not change with an increase in reaction time or a decrease in polymerase concentration, that length is used as a measure of processivity.

G. Use of Fusion Proteins to Increase Processivity of Pfu DNA Polymerase

The increase in processivity of a fusion protein comprising Pfu DNA polymerase relative to Pfu DNA polymerase alone is assessed using a processivity assay based on that of Wang et al. (2004) Nuc. Acids Res. 32:1197-1207. A 5' FAM-labeled primer of sequence 5' gttttcccagtcacgacgttgtaaaacgacggcc 3' (SEQ ID NO:29) is added to single stranded M13mp18 DNA in a mixture comprising 10 mM Tris-HCl pH 8.8, 50 mM KCl, 2.5 mM $MgCl_2$, 250 µm dNTPs, and 0.1% Triton X-100. The concentrations of the primer and M13mp18 template are 50 nM and 80 nM, respectively. The primer is annealed to the single stranded M13mp18 DNA template by heating the mixture to 90° C. for 5 minutes, cooling to 72° C. at 0.1° C. per second, incubating at 72° C. for 10 minutes, and cooling to 4° C. at 0.1° C. per second.

A reaction composition is prepared in which a fusion protein comprising Pfu DNA polymerase is added at a molar concentration of about 1:4000 (fusion protein:template) to 20 µl of the above mixture. A control reaction composition is prepared in which Pfu DNA polymerase is added at a molar concentration of about 1:4000 (DNA polymerase:template) to 20 µl of the above mixture. DNA synthesis is initiated in the reaction compositions by incubating them at 72° C. Samples from each reaction are taken at various time points. The samples are diluted in gel loading dye, and the primer extension products are analyzed by denaturing polyacrylamide gel electrophoresis using an ABI 377 DNA sequencer. The median product length is determined based on the integration of all detectable primer extension products. When the median product length does not change with an increase in reaction time or a decrease in polymerase concentration, that length is used as a measure of processivity.

One skilled in the art will readily recognize that the above assay may be modified so as to assess the processivity of a fusion protein comprising a DNA polymerase other than Taq or Pfu.

H. Use of Fusion Proteins in PCR

The ability of a fusion protein comprising a nucleic acid binding polypeptide and a thermostable DNA polymerase (e.g., Taq or Pfu) to increase the efficiency of PCR is demonstrated using a typical PCR reaction. An exemplary PCR reaction is prepared which contains PCR buffer (1×), dNTPs (200 µM each), template DNA (250 ng), forward and reverse primers (0.25 µM each) and fusion protein (about 0.5 to 2.5 units) in a final volume of 50 µl. As a control reaction, thermostable DNA polymerase alone is used in place of the fusion protein. The primers used in the PCR reaction are tPAF7 (5'-ggaagtacagctcagagttctgcagcacccctgc-3' (SEQ ID NO:45)) and tPAR10 (5'-gatgcgaaactgaggctggctgtactgtctc-3' (SEQ ID NO:46)). The template DNA is human genomic DNA (Roche, Indianapolis, Ind., P/N 1-691-112). The primers tPAF7 and tPAR10 amplify a product of approximately 5 kb from human genomic DNA. If the fusion protein being used in the PCR reaction comprises Pfu DNA polymerase, then the standard PCR buffer for Pfu (Stratagene; La. Jolla, Calif.) is used, except that the KCl concentration is elevated. The final working concentration (1×) of the buffer thus contains 20 mM Tris, pH 8:8; 10 mM $(NH_4)_2SO_4$, 0.1% Triton X-100, 2 mM $MgSO_4$, 100 µg/mL BSA and 60 mM KCl. If the fusion protein being used in the PCR reaction comprises Taq DNA polymerase, the standard PCR buffer for Taq (Applied Biosystems, Foster City, Calif.) is used. Cycling is performed as follows:

initial denaturation (98° C., 30 sec);
denaturation (98° C., 10 sec);
annealing (65° C., 10 sec); and ] 29 cycles -continued extension (72° C., 2 min);
and final extension (72° C., 10 min).

An aliquot of the reaction is analyzed by agarose gel electrophoresis along with an appropriate size standard, stained with ethidium bromide, and then visualized by fluorescence.

TABLE OF SEQUENCES

| SEQ ID NO: | Brief Description | Sequence |
|---|---|---|
| 1 | Pae3192 (protein) | MSKKQKLKFYDIKAKQAFETDQYEVIEKQTARGPMMFAVAKSPYTGIKVYRLLGKKK |
| 2 | PAE3192 (ORF) | atgtccaaga agcagaaact aaagttctac gacataaagg cgaagcaggc gtttgagact gaccagtacg aggttattga gaagcagact gcccgcggtc cgatgatgtt cgccgtggcc aaatcgccgt acaccggcat aaaagtatac agactgttag gcaagaagaa ataa |
| 3 | PAE3289 (ORF) | atgtccaaga agcagaaact aaagttctac gacataaagg cgaagcaggc gtttgagact gaccagtacg aggttattga gaagcagact gcccgcggtc cgatgatgtt cgccgtggcc aaatcgccgt acaccggcat aaaagtatac agactattag gcaagaagaa ataa |
| 4 | Pae0384 (protein) | MAKQKLKFYDIKAKQSFETDKYEVIEKETARGPM1FAVATSPYTGIKVYRLLGKKK |
| 5 | PAE0384 (ORF) | atggccaaac aaaaactaaa gttctacgac ataaaagcga acagtcctt cgaaacggac aaatacgagg tcattgagaa agagacggcc cgcgggccga tgttatttgc agtggcaacc tcgccgtaca ctggcataaa ggtgtacaga ctgttaggca agaagaaata a |
| 6 | Ape3192 | MPKKEKIKFFDLVAKKYYETDNYEVEIKETKRGKFRFAKAKSPYTGKIFYRVLGKA |
| 7 | APE3192 (ORF) | atgcccaaga aggagaagat aaagttcttc gacctagtcg ccaagaagta ctacgagact gacaactacg aagtcgagat aaaggagact aagaggggca gtttaggtt cgccaaagcc aagagcccgt acaccggcaa gatcttctat agagtgctag gcaaagccta g |
| 8 | p3192-a | atgtccaaga agcagaaact gaagttctac gacattaagg cgaagcaggc gtttgag |
| 9 | p3192-b | accgaccagt acgaggttat tgagaagcag accgcccgcg gtccgatgat gttcgcc |
| 10 | p3192-c | gtggccaaat cgccgtacac cggcattaaa gtgtaccgcc tgttaggcaa gaagaaataa |
| 11 | p3192-y | gtactggtcg gtctcaaacg cctg |
| 12 | P3192-Z | cgatttggcc acggcgaaca tcat |
| 13 | 8, 9, and 10 assembled | atgtccaaga agcagaaact gaagttctac gacattaagg cgaagcaggc gtttgagacc gaccagtacg aggttattga gaagcagacc gcccgcggtc cgatgatgtt cgccgtggcc aaatcgccgt acaccggcat taaagtgtac cgcctgttag gcaagaagaa ataa |
| 14 | ap3192-a | atgccgaaga aggagaagat taagttcttc gacctggtcg ccaagaagta ctacgag |
| 15 | ap3192-b | actgacaact acgaagtcga gattaaggag actaagegeg gcaagtttcg cttcgcc |
| 16 | ap3192-c | aaagccaaga gcccgtacac cggcaagatc ttctatcgcg tgctgggcaa agcctag |
| 17 | ap3192-y | gtagttgtca gtctcgtagt actt |
| 18 | ap3192-z | gctcttggct ttggcgaagc gaa |
| 19 | 14, 15, and 16 assembled | atgccgaaga aggagaagat taagttcttc gacctggtcg ccaagaagta ctacgagact gacaactacg aagtcgagat taaggagact aagcgcggca gtttcgctt cgccaaagcc aagagcccgt acaccggcaa gatcttctat cgcgtgctgg gcaaagccta g |
| 20 | oligo for annealing assay | gtaaaacgac ggccagt |
| 21 | mismatch oligo for annealing assay | gtaaaacgtc ggccagt |

TABLE OF SEQUENCES

| SEQ ID NO: | Brief Description | Sequence |
|---|---|---|
| 22 | polynucleotide encoding Pfu:Pae3192 fusion protein (including poly-His tag) | ccatgggccatcatcatcatcatcatcatcatcatcacagcagcggccatatcgaaggtc gtcatatgattttagatgtggattacataactgaagaaggaaaacctgttattaggctat tcaaaaagagaacggaaaatttaagatagagcatgatagaacttttagaccatacattt acgctcttctcagggatgattcaaagattgaagaagttaagaaaataacgggggaaaggc atggaaagattgtgagaattgttgatgtagagaaggttgagaaaaagtttctcggcaagc ctattaccgtgtggaaactttatttggaacatccccaagatgttcccactattagagaaa aagttagagaacatccagcagttgtggacatcttcgaatacgatattccatttgcaaaga gatacctcatcgacaaaggcctaataccaatggagggggaagaagagctaaagattcttg ccttcgatatagaaaccctctatcacgaaggaagagttttggaaaaggcccaattataa tgattagttatgcagatgaaaatgaagcaaaggtgattacttggaaaaacatagatcttc catacgttgaggttgtatcaagcgagagagagatgataaagagatttctcaggattatca gggagaaggatcctgacattatagttacttataatggagactcattcgacttcccatatt tagcgaaaagggcgaaaaaacttgggattaaattaaccattggaagagatggaagcgagc ccaagatgcagagaataggcgatatgacggctgtagaagtcaagggaagaatacatttcg acttgtatcatgtaataacaaggacaataaaatctcccaacatacacactagaggctgtat atgaagcaattttggaaagccaaaggagaaggtatacgccgacgagatagcaaaagcct gggaaagtggagagaaccttgagagagttgccaaatactcgatgaagatgcaaaggcaa cttatgaactcgggaaagaattccttccaatggaaattcagcttcaagattagttggac aacctttatgggatgtttcaaggtcaagcacagggaaccttgtagagtggttcttactta ggaaagcctacgaaagaaacgaagtagctccaaacaagccaagtgaagaggagtatcaaa gaaggctcagggagagctcacaggtggattcgttaaagagccgaaaaggggttgtggg aaaacatagtatacctagattttagagcccctatatccctcgattataattacccacaatg tttctcccgatactctaaatcttgagggatgcaagaactatgatatcgctcctcaagtag gccacaagttctgcaaggacatccctggttttataccaagtctcttgggacatttgttag aggaaagacaaaagattaagacaaaaatgaaggaaactcaagatcctatagaaaaaatac tccttgactatagacaaaagcgataaaactcttagcaaattctttctacggatatatatg gctatgcaaaagcaagatggtactgtaaggagtgtgctgagagcgttactgcctggggaa gaaagtacatcgagttagtatggaaggagctcgaagaaaagtttggatttaaagtcctct acattgacactgatggtctctatgcaactatcccaggaggagaaagtgaggaaataaaga aaaggctctagaatttgtaaaatacataaattcaaagctccctggactgctagagcttg aatatgaagggttttataagagggaggggattcttcgttacgaagaaggaggtatgcagtaataac atgaagaaggaaaagtcattactcgtggtttagagatagttaggagagattggagtgaaa ttgcaaaagaaactcaagctagagttttggagacaatactaaaacacggagatgttgaag aagctgtgagaatagtaaaagaagtaatacaaaagcttgccaattatgaaattccaccag agaagctcgcaatatatgagcagataacaagaccattacatgagtataaggcgataggtc ctcacgtagctgttgcaaaaactagctgctaaaggagttaaaataaagccaggaatgg taattggatacatagtacttagaggcgatggtccaattagcaataggcaattctagctg aggaatacgatcccaaaaagcacaagtatgacgcagaatattacattgagaaccaggttc ttccagcggtacttaggatattggagggatttggatacagaaaggaagacctcagatacc aaaagacaagacaagtcggcctaacttcctggcttaacattaaaaaatccggtaccggcg gtggcggtatgtccaagaagcagaaactgaagttctacgacattaaggcgaagcaggcgt ttgagaccgaccagtacgaggttattgagaagcagaccgcccgcggtccgatgatgttcg ccgtggccaaatcgccgtacaccggcattaaagtgtaccgcctgttaggcaagaagaaat aactcgag |
| 23 | amino acid sequence of Pfu:Ape3192 fusion protein (including poly-His tag) | MGHHHHHHHHHHSSGHIEGRHMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPPAKRYLIDKGLIPMEGEEELKILAFDIETLYHEGEEFGKGPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE AVRIVKEVIQKLANYEIPPEKLAIYEQITRPLHEYKAIGPHVAVAKKLAAKGVKIKPGMV IGYIVLRGDGPISNRAILAEEYDPKKHKYDAEYYIENQVLPAVLRILEGFGYRKEDLRYQ KTRQVGLTSWLNIKKSGTGGGGMSKKQKLKFYDIKAKQAFETDQYEVIEKQTARGPMMFA VAKSPYTGIKVYRLLGKKK |
| 24 | amino acid sequence of Pfu:Pae3192 fusion protein (after removal of poly-His tag) | HMILDVDYITEEGKPVIRLFKKENGKFKIEHDRTFRPYIY ALLRDDSKIEEVKKITGERHGKIVRIVDVEKVEKKFLGKPITVWKLYLEHPQDVPTIREK VREHPAVVDIFEYDIPPAKRYLIDKGLIPMEGEEELKILAFDIETLYHEGEEFGKGPIIM ISYADENEAKVITWKNIDLPYVEVVSSEREMIKRFLRIIREKDPDIIVTYNGDSFDFPYL AKRAEKLGIKLTIGRDGSEPKMQRIGDMTAVEVKGRIHFDLYHVITRTINLPTYTLEAVY EAIFGKPKEKVYADEIAKAWESGENLERVAKYSMEDAKATYELGKEFLPMEIQLSRLVGQ PLWDVSRSSTGNLVEWFLLRKAYERNEVAPNKPSEEEYQRRLRESYTGGFVKEPEKGLWE NIVYLDFRALYPSIIITHNVSPDTLNEGCKNYDIAPQVGHKFCKDIPGFIPSLLGHLLE ERQKIKTKMKETQDPIEKILLDYRQKAIKLLANSFYGYYGYAKARWYCKECAESVTAWGR KYIELVWKELEEKFGFKVLYIDTDGLYATIPGGESEEIKKKALEFVKYINSKLPGLLELE YEGFYKRGFFVTKKRYAVIDEEGKVITRGLEIVRRDWSEIAKETQARVLETILKHGDVEE |

| SEQ ID NO: | Brief Description | Sequence |
|---|---|---|
| | | AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKSGTGGGMSKKQKLKFYDIKAKQAFETDQYEVIEKQTARGPMMFA<br>VAKSPYTGIKVYRLLGKKK |
| 25 | polynucleotide encoding Pfu: Ape3192 fusion protein (including poly-His tag) | ccatgggccatcatcatcatcatcatcatcatcatcacagcagcggccatatcgaaggtc<br>gtcatatgattttagatgtggattacataactgaagaaggaaaacctgttattaggctat<br>tcaaaaaagagaacggaaaatttaagatagagcatgatagaacttttagaccatacattt<br>acgctcttctcagggatgattcaaagattgaagaagttaagaaaataacgggggaaaggc<br>atggaaagattgtgagaattgttgatgtagagaaggttgagaaaaagtttctcggcaagc<br>ctattaccgtgtgtgaaactttatttggaacatccccaagatgttcccactattagagaaa<br>aagttagagaacatccagcagttgtggacatcttcgaatacgatattccatttgcaaaga<br>gatacctcatcgacaaaggcctaataccaatggagggggaagaagagctaaagattcttg<br>ccttcgatatagaaaccctctatcacgaaggagaagagttttggaaaaggcccaattataa<br>tgattagttatgcagatgaaaatgaagcaaaggtgattacttggaaaaaacatagatcttc<br>catacgttgaggttgtatcaagcgagagagagatgataaagagatttctcaggattatca<br>gggagaaggatcctgacattatagttacttataatggagactcattcgacttcccatatt<br>tagcgaaaagggcagaaaaacttgggattaaattaaccattggaagagatggaagcgagc<br>ccaagatgcagagaataggcgatatgacggctgtagaagtcaagggaagaatacatttcg<br>acttgtatcatgtaataacaaggacaataaatctcccaacatacacactagaggctgtat<br>atgaagcaatttttggaaagccaaaggagaaggtatacgccgacgagatagcaaaagcct<br>gggaaagtgagagaaaccttgagagagttgccaaatactcgatgaagatgcaaaagcgaa<br>cttatgaactcgggaaagaattccttccaatggaaattcagcttttcaagattagttggac<br>aacctttatgggatgtttcaaggtcaagcacagggaaccttgtagagtggttcttactta<br>ggaaagcctacgaaagaaacgaagtagctccaaacaagccaagtgaagaggagtatcaaa<br>gaaggctcagggagagctcacacaggtggattcgttaaagagccagaaaaggggtgtggg<br>aaaacatagtatacctagattttagagcccctatatccctcgattataattacccacaatg<br>tttctcccgatactctaaatcttgagggatgcaagaactatgatatcgctcctcaagtag<br>gccacaagttctgcaaggacatccctggttttataccaagtctcttgggacatttgttag<br>aggaaagacaaaagattaagacaaaaatgaaggaaactcaagatcctatagaaaaaatac<br>tccttgactatagacaaaaagcgataaaactcttagcaaattcttttctacggatattat<br>gctatgcaaaagcaagatggtactgtaaggagtgtgctgagagcgttactgcctgggaa<br>gaaagtacatcgagttagtatggaaggagctcgaagaaaagtttggatttaaagtcctct<br>acattgacactgatggtctctatgcaactatcccaggaggagaaagtgaggaaataaga<br>aaaaggctctagaatttgtaaaatacataaattcaaagctccctggactgctagagcttg<br>aatatgaagggttttataagagggggattcttcgttacgaagaagaggtatgcagtaatag<br>atgaagaaggaaaagtcattactcgtggtttagagatagttaggagagattggagtgaaa<br>ttgcaaaagaaactcaagctagagttttggagacaatactaaaacacggagatgttgaag<br>aagctgtgagaatagtaaaagaagtaatacaaaagcttgccaattatgaaattccaccag<br>agaagctcgcaatatatgagcagataacaagaccattacatgagtataaggcgataggtc<br>ctcacgtagctgttgcaaagaaactagctgctaaaggagttaaaataaagccaggaatgg<br>taattggatacatagtacttagaggcgatggtccaattagcaataggcaattctagctg<br>aggaatacgatcccaaaaagcacaagtgacgcagaatattacattgagaaccaggttc<br>ttccagcggtacttaggatattggagggatttggatacagaaaggaagacctcagatacc<br>aaaagacaagacaagtcggcctaacttcctggcttaacattaaaaaatccggtaccggcg<br>gtggcggtccgaagaaggagaagattaggttcttcgacctggtcgccaagaagtactacg<br>agactgacaactacgaagtcgagattaaggagaacaagcgcggcaagtttcgcttcgcca<br>agccaagagcccgtacaccggcaagatcttctatcgcgtgctgggcaaagcctaactcgag |
| 26 | amino acid sequence of Pfu: Ape3192 fusion protein (including poly-His tag) | MGHHHHHHHHHSSGHIEGRHMILDVDYITEEGKPVIRLFKKENGKFKIEHDRTFRPYIY<br>ALLRDDSKIEEVKKITGERHGKIVRIVDVEKVEKKFLGKPITVWKLYLEHPQDVPTIREK<br>VREHPAVVDIFEYDIPFAKRYLIDKGLIPMEGEEELKILAFDIETLYHEGEEFGKGPIIM<br>ISYADENEAKVITWKNIDLPYVEVVSSEREMIKRFLRIIREKDPDIIVTYNGDSFDPYL<br>AKRAEKLGIKLTIGRDSEPKMQRIGDMTAVEVKGRIHFDLYHVITRTINLPTYTLEAVY<br>EAIFGKPKEKVYADEIAKAWESGENLERVAKYSMEDAKATYELGKEFLPMEIQLSRLVGQ<br>PLWDVSRSSTGNLVEWFLLRKAYERNEVAPNKPSEEEYQRRLRESYTGGFVKEPEKGLWE<br>NIVYLDFRALYPSIIITHNVSPDTLNLEGCKNYDIAPQVGHKFCKDIPGFIPSLLGHLLE<br>ERQKIKTKMKETQDPIEKILLDYRQKAIKLLANSFYGYYGYAKARWYCKECAESVTAWGR<br>KYIELVWKELEEKFGFKVLYIDTDGLYATIPGGESEEIKKKALEFVKYINSKLPGLLELE<br>YEGFYKRGFFVTKKRYAVIDEEGKVITRGLEIVRRDWSEIAKETQARVLETILKHGDVEE<br>AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKSGTGGGPKKEKIRFFDLVAKKYYETDNYEVEIKETKRGKFRFAK<br>AKSPYTGKIFYRVLGKA |
| 27 | amino acid sequence of Pfu: Ape3192 fusion protein (after removal of tag) | HMILDVDYITEEGKPVIRLFKKENGKFKIEHDRTFRPYIY<br>ALLRDDSKIEEVKKITGERHGKIVRIVDVEKVEKKFLGKPITVWKLYLEHPQDVPTIREK<br>VREHPAVVDIFEYDIPFAKRYLIDKGLIPMEGEEELKILAFDIETLYHEGEEFGKGPIIM<br>ISYADENEAKVITWKNIDLPYVEVVSSEREMIKRFLRIIREKDPDIIVTYNGDSFDPYL<br>AKRAEKLGIKLTIGRDSEPKMQRIGDMTAVEVKGRIHFDLYHVITRTINLPTYTLEAVY<br>EAIFGKPKEKVYADEIAKAWESGENLERVAKYSMEDAKATYELGKEFLPMEIQLSRLVGQ<br>PLWDVSRSSTGNLVEWFLLRKAYERNEVAPNKPSEEEYQRRLRESYTGGFVKEPEKGLWE<br>NIVYLDFRALYPSIIITHNVSPDTLNLEGCKNYDIAPQVGHKFCKDIPGFIPSLLGHLLE<br>ERQKIKTKMKETQDPIEKILLDYRQKAIKLLANSFYGYYGYAKARWYCKECAESVTAWGR<br>KYIELVWKELEEKFGFKVLYIDTDGLYATIPGGESEEIKKKALEFVKYINSKLPGLLELE |

TABLE OF SEQUENCES

| SEQ ID NO: | Brief Description | Sequence |
|---|---|---|
| | | YEGFYKRGFFVTKKRYAVIDEEGKVITRGLEIVRRDWSEIAKETQARVLETILKHGDVEE<br>AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKSGTGGGGPKKEKIRFFDLVAKKYYETDNYEVEIKETKRGKFRFAK<br>AKSPYTGKIFYRVLGKA |
| 28 | Pae/Ape consensus sequence | KXKXKFXDXXAKXXXETDXYEVXXKXTXRGXXXFAXAKSPYTGXXXYRXLGK |
| 29 | oligo for processivity assay | gttttcccagtcacgacgttgtaaaacgacggcc |
| 30 | Sso7d | MATVKFKYKGEEKQVDISKIKKVWRVGKMISFTYDEGGGKTGRGAVSEKDAPKELLQMLEKQKK |
| 31 | Pfu DNA polymerase | MILDVDYITEEGKPVIRLFKKENGKFKIEHDRTFRPYIY<br>ALLRDDSKIEEVKKITGERHGKIVRIVDVEKVEKKFLGKPITVWKLYLEHPQDVPTTREK<br>VREHPAVVDIFEYDIPFAKRYLIDKGLIPMEGEEELKILAFDIETLYHEGEEFGKGPIIM<br>ISYADENEAKVITWKNIDLPYVEVVSSEREMIKRFLRIIREKDPDIIVTYNGDSFDEPYL<br>AKRAEKLGIKLTIGRDGSEPKMQRIGDMTAVEVKGRIHFDLYHVITRTINLPTYTLEAVY<br>EATFGKPKEKVYADEIAKAWESGENLERVAKYSMEDAKATYELGKEFLPMEIQLSRLVGQ<br>PLWDVSRSSTGNLVEWFLLRKAYERNEVAPNKPSEEEYQRRLRESYTGGFVKEPEKGLWE<br>NIVYLDFRALYPSIIITHNVSPDTLNLEGCKNYDIAPQVGHKECKDIPGEIPSLLGHLLE<br>ERQKIKTKMKETQDPIEKILLDYRQKAIKLLANSFYGYYGYAKARWYCKECAESVTAWGR<br>KYIELVWKELEEKFGEKVLYIDTDGLYATIPGGESEEIKKKALEFVKYINSKLPGLLELE<br>YEGFYKRGFEVTKKRYAVIDEEGKVITRGLEIVRRDWSEIAKETQARVLETILKHGDVEE<br>AVRIVKEVIQKLANYEIPPEKLAIYEQITRPLHEYKAIGPHVAVAKKLAAKGVKIKPGMV<br>IGYIVLRGDGPISNRAILAEEYDPKKHKYDAEYYIENQVLPAVLRILEGFGYRKEDLRYQ<br>KTRQVGLTSWLNIKKS |
| 32 | Taq DNA polymerase | MRGMLPLFEPKGRVLLVDGHHLAYRTFHALKGLTTSRGEPVQAVYGFAKSLLKALKEDG<br>DAVIVVFDAKAPSERHEAYGGYKAGRAPTPEDEPRQLALIKELVDLLGLARLEVPGYEA<br>DDVLASLAKKAEKEGYEVRILTADKDLYQLLSDRIHVLHPEGYLITPAWLWEKYGLRPD<br>QWADYRALTGDESDNLPGVKGIGEKTARKLLEENGSLEALLKNLDRLKPAIREKILAHM<br>DDLKLSWDLAKVRTDLPLEVDFAKRREPDRERLRAFLERLEFGSLLHEFGLLESPKALE<br>EAPWPPPEGAFVGFVLSRKEPMWADLLALAAARGGRVHRAPEPYKALRDLKEARGLLAK<br>DLSVLALREGLGLPPGDDPMLLAYLLDPSNTTPEGVARRYGGEWTEEAGERAALSERLF<br>ANLWGRLEGEERLLWLYREVERPLSAVLAHMEATGVRLDVAYLRALSLEVAEEIARLEA<br>EVERLAGHPFNLNSRDQLERVLFEDELGLPAIGKTEKTGKRSTSAAVLEALREAHPIVEK<br>ILQYRELTKLKSTYIDPLPDLIHPRTGRLHTRENQTATATGRLSSSDPNLQNIPVRTPL<br>GQRIRRAFIAEEGWLLVALDYSQIELRVLAHLSGDENLIRVFQEGRDIHTETASWMFGV<br>PREAVDPLMRRAAKTINFGVLYGMSAHRLSQELAIPYEEAQAFIERYFQSFPKVRAWIE<br>KTLEEGRRRGYVETLFGRRRYVPDLEARVKSVREAAERMAFNMPVQGTAADLMKLAMVK<br>LFPRLEEMGARMLLQVHDELVLEAPKERAEAVARLAKEVMEGVYPLAVPLEVEVGIGED<br>WLSAKE |
| 33 | polynucleotide encoding Pae3192: Taq fusion protein (including poly-His tag) | ATGGGCCATCATCATCATCATCATCATCATCATCACAGCAGCGGCCATATCGAAGGTCG<br>TCATATGTCCAAGAAGCAGAAACTGAAGTTCTACGACATTAAGGCGAAGCAGGCGTTTG<br>AGACCGACCAGTACGAGGTTATTGAGAAGCAGACCGCCCGCGGTCCGATGATGTTCGCC<br>GTGGCCAAATCGCCGTACACCGGCATTAAAGTGTACCGCCTGTTAGGCAACGAAGAAAGG<br>CGGCGGTGTCACTAGTGGGATGCTGCCCCTCTTTGAGCCCAAGGGCCGGGTCCTCCTGG<br>TGGACGGCCACCACCTGGCCTACCGGACCTTCCACGCCCTGAAGGGCCTCACCACCAGC<br>CGGGGGGAGCCGGTGCAGGCGGTCTACGGCTTCGCCAAGAGCCTCCTCAAGGCCCTCAA<br>GGAGGACGGGGACGCGGTGATCGTGGTCTTTGACGCCAAGGCCCCTCCTTCCGCCACG<br>AGGCCTACGGGGGGTACAAGGCGGGCCGGGCCCCCACGCCGGAGGACTTTCCCCGGCAA<br>CTCGCCCTCATCAAGGAGCTGGTGGACCTCCTGGGGCTGGCGCGCCTCGAGGTCCCGGG<br>CTACGAGGCGGACGACGTCCTGGCCAGCCTGGCCAAGAAGGCGGAAAAGGAGGGCTACG<br>AGGTCCGCATCCTCACCGCCGACAAGGACCTTTACCAGCTCCTTTCCGACCGCATCCAC<br>GTCCTCCACCCCGAGGGGTACCTCATCACCCCGGCCTGGCTTTGGGAAAAGTACGGCCT<br>GAGGCCCGACCAGTGGGCCGACTACCGGGCCCTGACCGGGGACGAGTCCGACAACCTTC<br>CCGGGGTCAAGGGCATCGGGGAGAAGACGGCGAGGAAGCTTCTGGAGGAGTGGGGGAGC<br>CTGGAAGCCCTCCTCAAGAACCTGGACCGGCTGAAGCCCGCCATCCGGGAGAAGATCCT<br>GGCCCACATGGACGATCTGAAGCTCTCCTGGGACCTGGCCAAGGTGCGCACCGACCTGC<br>CCCTGGAGGTGGACTTCGCCAAAAGGCGGGAGCCCGACCGGGAGAGGCTTAGGGCCTTT<br>CTGGAGAGGCTTGAGTTTGGCAGCCTCCTCCACGAGTTCGGCCTTCTGGAAAGCCCCAA<br>GGCCCTGGAGGAGGCCCCCTGGCCCCCGCCGGAAGGGGCCTTCGTGGGCTTTGTGCTTT<br>CCCGCAAGGAGCCCATGTGGGCCGATCTTCTGGCCCTGGCCGCCGCAGGGGGGGCCGG<br>GTCCACCGGGCCCCGAGCCTTATAAAGCCCTCAGGGACCTGAAGGAGGCGCGGGGCT<br>TCTCGCAAAGACCTGAGCGTTCTGGCCCTGAGGGAAGGCCTTGGCCTCCCGCCCGGCG<br>ACGACCCCATGCTCCTCGCCTACCTCCTGGACCCTTCCAACACCACCCCCGAGGGGGTG<br>GCCCGGCGCTACGGCGGGAGTGGACGGAGGAGCGGGGAGCGGGCCGCCCTTTCCGA<br>GAGGCTCTTCGCCAACCTGTGGGGAGGCTTGAGGGGAGGAGAGGCTCCTTTGGCTTT<br>ACCGGGAGGTGGAGAGGCCCCTTTCCGCTGTCCTGGCCCACATGGAGGCCACGGGGGTG<br>CGCCTGGACGTGGCCTATCTCAGGGCCTTGTCCCTGGAGGTGGCCGAGGAGATCGCCCG |

TABLE OF SEQUENCES

| SEQ ID NO: | Brief Description | Sequence |
|---|---|---|
| | | CCTCGAGGCCGAGGTCTTCCGCCTGGCCGGCCACCCCTTCAACCTCAACTCCCGGGACC<br>AGCTGGAAAGGGTCCTCTTTGACGAGCTAGGGCTTCCCGCCATCGGCAAGACGGAGAAG<br>ACCGGCAAGCGCTCCACCAGCGCCGCCGTCCTGGAGGCCCTCCGCGAGGCCCACCCCAT<br>CGTGGAGAAGATCCTGCAGTACCGGGAGCTCACCAAGCTGAAGAGCACCTACATTGACC<br>CCTTGCCGGACCTCATCCACCCCAGGACGGGCCGCCTCCACACCCGCTTCAACAAGACG<br>GCCACGGCCACGGGCAGGCTAAGTAGCTCCGATCCCAACCTCCAGAACATCCCCGTCCG<br>CACCCCGCTTGGGCAGAGGATCCGCCGGGCCTTCATCGCCGAGGAGGGTGGCTATTGG<br>TGGCCCTGGACTATAGCCAGATAGAGCTCAGGGTGCTGGCCCACCTCTCCGGCGACGAG<br>AACCTGATCCGGGTCTTCCAGGAGGGGCGGGACATCCACACGGAGACCGCCAGCTGGAT<br>GTTCGGCGTCCCCCGGGAGGCCGTGGACCCCCTGATGCGCCGGGCGGCCAAGACCATCA<br>ACTTCGGGGTCCTCTACGGCATGTCGGCCCACCGCCTCTCCCAGGAGCTAGCCATCCCT<br>TACGAGGAGGCCCAGGCCTTCATTGAGCGCTACTTTCAGAGCTTCCCCAAGGTGCGGGC<br>CTGGATTGAGAAGACCCTGGAGGAGGGCAGGAGGCGGGGGTACGTGGAGACCCTCTTCG<br>GCCGCCGCCGCTACGTGCCAGACCTAGAGGCCCGGGTGAAGAGCGTGCGGGAGGCGGCC<br>GAGCGCATGGCCTTCAACATGCCCGTCCAGGGCACCGCCGCCGACCTCATGAAGCTGAC<br>TATGGTGAAGCTCTTCCCCAGGCTGGAGGAAATGGGGGCCAGGATGCTCCTTCAGGTCC<br>ACGACGAGCTGGTCCTCGAGGCCCCAAAAGAGAGGGCGGAGGCCGTGGCCCGGCTGGCC<br>AAGGAGGTCATGGAGGGGGTGTATCCCCTGGCCGTGCCCCTGGAGGTGGAGGTGGGGAT<br>AGGGGAGGACTGGCTCTCCGCCAAGGAGTGA |
| 34 | amino acid sequence of Pae3192: Taq fusion protein (including poly-His tag) | MGHHHHHHHHHHSSGHIEGRHMSKKQKLKFYDIKAKQAFETDQYEVIEKQTARGPMMFA<br>VAKSPYTGIKVYRLLGKKKGGGVTSGMLPLFEPKGRVLLVDGHHLAYRTFHALKGLTTS<br>RGEPVQAVYGFAKSLLKALKEDGDAVIVVFDAKAPSFRHEAYGGYKAGRAPTPEDFPRQ<br>LALIKELVDLLGLARLEVPGYEADDVLASLAKKAEKEGYEVRILTADKDLYQLLSDRIH<br>VLHPEGYLITPAWLWEKYGLRPDQWADYRALTGDESDNLPGVKGIGEKTARKLLEEWGS<br>LEALLKNLDRLKPAIREKILAHMDDLKLSWDLAKVRTDLPLEVDFAKRREPDRERLRAF<br>LERLEFGSLLHEFGLLESPKALEEAPWPPPEGAFVGFVLSRKEPMWADLLALAAARGGR<br>VHRAPEPYKALRDLKEARGLLAKDLSVLALREGLGLPPGDDPMLLAYLLDPSNTTPEGV<br>ARRYGGEWTEEAGERAALSERLFANLWGRLEGEERLLWLYREVERPLSAVLAHMEATGV<br>RLDVAYLRALSLEVAEEIARLEAEVFRLAGHPFNLNSRDQLERVLFDELGLPAIGKTEK<br>TGKRSTSAAVLEALREAHPIVEKILQYRELTKLKSTYIDPLPDLIHPRTGRLHTRFNQT<br>ATATGRLSSSDPNLQNIPVRTPLGQRIRRAFIAEEGWLLVALDYSQIELRVAHLSGDE<br>NLIRVFQEGRDIHTETASWMFGVPREAVDPLMRRAAKTINFGVLYGMSAHRLSQELAIP<br>YEEAQAFIERYFQSFPKVRAWIEKTLEEGRRRGYVETLFGRRRYVPDLEARVKSVREAA<br>ERMAFNMPVQGTAADLMKLAMVKLFPRLEEMGARMLLQVHDELVLEAPKERAEAVARLA<br>KEVMEGVYPLAVPLEVEVGIGEDWLSAKE |
| 35 | amino acid sequence of Pae3192: Taq fusion protein (after removal of poly-His tag) | HMSKKQKLKFYDIKAKQAFETDQYEVIEKQTARGPMMFA<br>VAKSPYTGIKVYRLLGKKKGGGVTSGMLPLFEPKGRVLLVDGHHLAYRTFHALKGLTTS<br>RGEPVQAVYGFAKSLLKALKEDGDAVIVVFDAKAPSFRHEAYGGYKAGRAPTPEDFPRQ<br>LALIKELVDLLGLARLEVPGYEADDVLASLAKKAEKEGYEVRILTADKDLYQLLSDRIH<br>VLHPEGYLITPAWLWEKYGLRPDQWADYRALTGDESDNLPGVKGIGEKTARKLLEEWGS<br>LEALLKNLDRLKPAIREKILAHMDDLKLSWDLAKVRTDLPLEVDFAKRREPDRERLRAF<br>LERLEFGSLLHEFGLLESPKALEEAPWPPPEGAFVGFVLSRKEPMWADLLALAAARGGR<br>VHRAPEPYKALRDLKEARGLLAKDLSVLALREGLGLPPGDDPMLLAYLLDPSNTTPEGV<br>ARRYGGEWTEEAGERAALSERLFANLWGRLEGEERLLWLYREVERPLSAVLAHMEATGV<br>RLDVAYLRALSLEVAEEIARLEAEVFRLAGHPFNLNSRDQLERVLFDELGLPAIGKTEK<br>TGKRSTSAAVLEALREAHPIVEKILQYRELTKLKSTYIDPLPDLIHPRTGRLHTRFNQT<br>ATATGRLSSSDPNLQNIPVRTPLGQRIRRAFIAEEGWLLVALDYSQIELRVAHLSGDE<br>NLIRVFQEGRDIHTETASWMFGVPREAVDPLMRRAAKTINFGVLYGMSAHRLSQELAIP<br>YEEAQAFIERYFQSFPKVRAWIEKTLEEGRRRGYVETLFGRRRYVPDLEARVKSVREAA<br>ERMAFNMPVQGTAADLMKLAMVKLFPRLEEMGARMLLQVHDELVLEAPKERAEAVARLA<br>KEVMEGVYPLAVPLEVEVGIGEDWLSAKE |
| 36 | polynucleotide encoding Ape3192: Taq fusion protein (inclusing poly-His tag) | ATGGGCCATCATCATCATCATCATCATCATCATCATCACAGCAGCGGCCATATCGAAG<br>GTCGTCATATGCCGAAGAAGGAGAAGATTAAGTTCTTCGACCTGGTCGCCAAGAAGTAC<br>TACGAGACTGACAACTACGAAGTCGAGATTAAGGAGACTAAGCGCGGCAAGTTTCGCTT<br>CGCCAAAGCCAAGAGCCCGTACACCGGCAAGATCTTCTATCGCGTGCTGGGCAAAGCCG<br>GCGGCGGTGTCACTAGTGGGATGCTGCCCCTCTTTGAGCCCAAGGGCCGGGTCCTTCTG<br>GTGGACGGCCACCACCTGGCCTACCGCACCTTCCACGCCCTGAAGGGCCTCACCACCAG<br>CCGGGGGGAGCCGGTGCAGGCGGTCTACGGCTTCGCCAAGAGCCTCCTCAAGGCCCTCA<br>AGGAGGACGGGGACGCGGTGATCGTGGTCTTTGACGCCAAGGCCCCCTCCTTCCGCCAC<br>GAGGCCTACGGGGGGTACAAGGCGGGCCGGGCCCCCACGCCGGAGGACTTTCCCCGGCA<br>ACTCGCCCTCATCAAGGAGCTGGTGGACCTCCTGGGGCTGGCGCGCCTCGAGGTCCCGG<br>GCTACGAGGCGGACGACGTCCTGGCCAGCCTGGCCAAGAAGGCGGAAAAGGAGGGCTAC<br>GAGGTCCGCATCCTCACCGCCGACAAAGACCTTTACCAGCTCCTTTCCGACCGCATCCA<br>CGTCCTCCACCCCGAGGGGTACCTCATCACCCCGGCCTGGCTTTGGGAAAAGTACGGCC<br>TGAGGCCCGACCAGTGGGCCGACTACCGGGCCCTGACCGGGGACGAGTCCGACAACCTT<br>CCCGGGGTCAAGGGCATCGGGGAGAAGACGGCGAGGAAGCTTCTGGAGGAGTGGGGGAG<br>CCTGGAAGCCCTCCTCAAGAACCTGGACCGGCTGAAGCCCGCCATCCGGGAAGATCC<br>TGGCCCACATGGACGATCTGAAGCTCTCCTGGGACCTGGCCAAGGTGCGCACCGACCTG<br>CCCCTGGAGGTGGACTTCGCCAAAAGGCGGGAGCCCGACCGGGAGAGGCTTAGGGCCTT<br>TCTGGAGAGGCTTGAGTTTGGCAGCCTCCTCCACGAGTTCGGCCTTCTGGAAAGCCCCA<br>AGGCCCTGGAGGAGGCCCCCTGGCCCCCGCCGGAAGGGGCCTTCGTGGGCTTTGTGCTT<br>TCCCGCAAGGAGCCCATGTGGGCCGATCTTCTGGCCCTGGCCGCCGCCAGGGGGGCCG |

TABLE OF SEQUENCES

| SEQ ID NO: | Brief Description | Sequence |
|---|---|---|
| | | GGTCCACCGGGCCCCCGAGCCTTATAAAGCCCTCAGGGACCTGAAGGAGGCGCGGGGGC<br>TTCTCGCCAAAGACCTGAGCGTTCTGGCCCTGAGGGAAGGCCTTGGCCTCCCGCCCGGC<br>GACGACCCCATGCTCCTCGCCTACCTCCTGGACCCTTCCAACACCACCCCCGAGGGGGT<br>GGCCCGGCGCTACGGCGGGGAGTGGACGGAGGAGGCGGGGGAGCGGGCCGCCCTTTCCG<br>AGAGGCTCTTCGCCAACCTGTGGGGGAGGCTTGAGGGGGAGGAGAGGCTCCTTTGGCTT<br>TACCGGGAGGTGGAGAGGCCCCTTTCCGCTGTCCTGGCCCACATGGAGGCCACGGGGGT<br>GCGCCTGGACGTGGCCTATCTCAGGGCCTTGTCCCTGGAGGTGGCCGAGGAGATCGCCC<br>GCCTCGAGGCCGAGGTCTTCCGCCTGGCCGGCCACCCCTTCAACCTCAACTCCCGGGAC<br>CAGCTGGAAAGGGTCCTCTTTGACGAGCTAGGGCTTCCCGCCATCGGCAAGACGGAGAA<br>GACCGGCAAGCGCTCCACCAGCGCCGCCGTCCTGGAGGCCCTCCGCGAGGCCCACCCCA<br>TCGTGGAGAAGATCCTGCAGTACCGGGAGCTCACCAAGCTGAAGAGCACCTACATTGAC<br>CCCTTGCCGGACCTCATCCACCCCAGGACGGGCCGCCTCCACACCCGCTTCAACCAGAC<br>GGCCACGGCCACGGGCAGGCTAAGTAGCTCCGATCCCAACCTCCAGAACATCCCCGTCC<br>GCACCCCGCTTGGGCAGAGGATCCGCCGGGCCTTCATCGCCGAGGAGGGGTGGCTATTG<br>GTGGCCCTGGACTATAGCCAGATAGAGCTCAGGGTGCTGGCCCACCTCTCCGGCGACGA<br>GAACCTGATCCGGGTCTTCCAGGAGGGGCGGGACATCCACACGGAGACCGCCAGCTGGA<br>TGTTCGGCGTCCCCCGGGAGGCCGTGGACCCCCTGATGCGCCGGGCGGCCAAGACCATC<br>AACTTCGGGGTCCTCTACGGCATGTCGGCCCGCCTCTCCCAGGAGCTAGCCATCCC<br>TTACGAGGAGGCCCAGGCCTTCATTGAGCGCTACTTTCAGAGCTTCCCCAAGGTGCGGG<br>CCTGGATTGAGAAGACCCTGGAGGAGGGCAGGAGGCGGGGGTACGTGGAGACCCTCTTC<br>GGCCGCCGCCGCTACGTGCCAGACCTAGAGGCCCGGGTGAAGAGCGTGCGGGAGGCGGC<br>CGAGCGCATGGCCTTCAACATGCCCGTCCAGGGCACCGCCGCCGACCTCATGAAGCTGG<br>CTATGGTGAAGCTCTTCCCCAGGCTGGAGGAAATGGGGGCCAGGATGCTCCTTCAGGTC<br>CACGACGAGCTGGTCCTCGAGGCCCCAAAAGAGAGGGCGGAGGCCGTGGCCCGGCTGGC<br>CAAGGAGGTCATGGAGGGGGTGTATCCCCTGGCCGTGCCCCTGGAGGTGGAGGTGGGGA<br>TAGGGGAGGACTGGCTCTCCGCCAAGGAGTGA |
| 37 | amino acid sequence of Ape3192: Taq fusion protein (including poly-His tag) | MGHHHHHHHHHSSGHIEGRHMPKKEKIKFFDLVAKKYYETDNYEVEIKETKRGKFRFA<br>KAKSPYTGKIFYRVLGKAGGGVTSGMLPLFEPKGRVLLVDGHHLAYRTFHALKGLTTSR<br>GEPVQAVYGFAKSLLKALKEDGDAVIVVFDAKAPSFRHEAYGGYKAGRAPTPEDFPRQL<br>ALIKELVDLLGLARLEVPGYEADDVLASLAKKAEKEGYEVRILTADKDLYQLLSDRIHV<br>LHPEGYLITPAWLWEKYGLRPDQWADYRALTGDESDNLPGVKGIGEKTARKLLEEWGSL<br>EALLKNLDRLKPAIREKILAHMDDLKLSWDLAKVRTDLPLEVDFAKRREPDRERLRAFL<br>ERLEFGSLLHEFGLLESPKALEEEAPWPPEGAFVGFVLSRKEPMWADLLALAAARGGRV<br>HRAPEPYKALRDLKEARGLLAKDLSVLALREGLGLPPGDDPMLLAYLLDPSNTTPEGVA<br>RRYGGEWTEEAGERAALSERLFANLWGRLEGEERLLWLYREVERPLSAVLAHMEATGVR<br>LDVAYLRALSLEVAEEIARLEAEVERLAGHPFNLNSRDQLERVLEDELGLPAIGKTEKT<br>GKRSTSAAVLEALREAHPIVEKILQYRELTKLKSTYIDPLPDLIHPRTGRLHTRENQTA<br>TATGRLSSSDPNLQNIPVRTPLGQRIRRAFIAEEGWLLVALDYSQIELRVLAHLSGDEN<br>LIRVFQEGRDIHTETASWMFGVPREAVDPLMRRAAKTINFGVLYGMSAHRLSQELAIPY<br>EEAQAFIERYFQSFPKVRAWIEKTLEEGRRRGYVETLFGRRRYVPDLEARVKSVREAAE<br>RMAFNMPVQGTAADLMKLAMVKLFPRLEEMGARMLLQVHDELVLEAPKERAEAVARLAK<br>EVMEGVYPLAVPLEVEVGIGEDWLSAKE |
| 38 | amino acid sequence of Ape3192: Taq fusion protein (after removal of poly-His tag) | HMPKKEKIKFFDLVAKKYYETDNYEVEIKETKRGKFRFA<br>KAKSPYTGKIFYRVLGKAGGGVTSGMLPLFEPKGRVLLVDGHHLAYRTFHALKGLTTSR<br>GEPVQAVYGFAKSLLKALKEDGDAVIVVFDAKAPSFRHEAYGGYKAGRAPTPEDFPRQL<br>ALIKELVDLLGLARLEVPGYEADDVLASLAKKAEKEGYEVRILTADKDLYQLLSDRIHV<br>LHPEGYLITPAWLWEKYGLRPDQWADYRALTGDESDNLPGVKGIGEKTARKLLEEWGSL<br>EALLKNLDRLKPAIREKILAHMDDLKLSWDLAKVRTDLPLEVDFAKRREPDRERLRAFL<br>ERLEFGSLLHEFGLLESPKALEEEAPWPPEGAFVGFVLSRKEPMWADLLALAAARGGRV<br>HRAPEPYKALRDLKEARGLLAKDLSVLALREGLGLPPGDDPMLLAYLLDPSNTTPEGVA<br>RRYGGEWTEEAGERAALSERLFANLWGRLEGEERLLWLYREVERPLSAVLAHMEATGVR<br>LDVAYLRALSLEVAEEIARLEAEVERLAGHPFNLNSRDQLERVLEDELGLPAIGKTEKT<br>GKRSTSAAVLEALREAHPIVEKILQYRELTKLKSTYIDPLPDLIHPRTGRLHTRENQTA<br>TATGRLSSSDPNLQNIPVRTPLGQRIRRAFIAEEGWLLVALDYSQIELRVLAHLSGDEN<br>LIRVFQEGRDIHTETASWMFGVPREAVDPLMRRAAKTINFGVLYGMSAHRLSQELAIPY<br>EEAQAFIERYFQSFPKVRAWIEKTLEEGRRRGYVETLFGRRRYVPDLEARVKSVREAAE<br>RMAFNMPVQGTAADLMKLAMVKLFPRLEEMGARMLLQVHDELVLEAPKERAEAVARLAK<br>EVMEGVYPLAVPLEVEVGIGEDWLSAKE |
| 39 | polynucleotide encoding Pae3192: Stoffel-Taq fusion protein (including poly-His tag) | ATGGGCCATCATCATCATCATCATCATCATCATCACAGCAGCGGCCATATCGAAGGTCG<br>TCATATGTCCAAGAAGCAGAAACTGAAGTTCTACGACATTAAGGCGAAGCAGGCGTTTG<br>AGACCGACCAGTACGAGGTTATTGAGAAGCAGACCCGCCCGCGGTCCGATGATGTTGCC<br>GTGGCCAAATCGCCGTACACCGGCATTAAAGTGTACCCGCTCGTTAGGCAAGAAGAAGG<br>CGGCGGTGTCACTAGTCCCAAGGCCCTGGAGGAGGCCCCCTGGCCCCCGCCGGAAGGGG<br>CCTTCGTGGGCTTTGTGCTTTCCCGCAAGGAGCCCATGTGGGCCGATCTTCTGGCCCTG<br>GCCGCCGCCAGGGGGGCCGGGTCCACCGGGCCCCCGAGCCTTATAAAGCCCTCAGGGA<br>CCTGAAGGAGGCGCGGGGGCTTCTCGCCAAAGACCTGAGCGTTCTGGCCCTGAGGGAAG<br>GCCTTGGCCTCCCGCCCGGCGACGACCCCATGCTCCTCGCCTACCTCCTGGACCCTTCC<br>AACACCACCCCCGAGGGGGTGGCCCGGCGCTACGGCGGGGAGTGGACGGAGGAGGCGGG<br>GGAGCGGGCCGCCCTTTCCGAGAGGCTCTTCGCCAACCTGTGGGGGAGGCTTGAGGGGG<br>AGGAGAGGCTCCTTTGGCTTTACCGGGAGGTGGAGAGGCCCCTTTCCGCTGTCCTGGCC<br>CACATGGAGGCCACGGGGGTGCGCCTGGACGTGGCCTATCTCAGGGCCTTGTCCCTGGA<br>GGTGGCCGAGGAGATCGCCCGCCTCGAGGCCGAGGTCTTCCGCCTGGCCGGCCACCCCT |

TABLE OF SEQUENCES

| SEQ ID NO: | Brief Description | Sequence |
|---|---|---|
| | | TCAACCTCAACTCCCGGGACCAGCTGGAAAGGGTCCTCTTTGACGAGCTAGGGCTTCCC<br>GCCATCGGCAAGACGGAGAAGACCGGCAAGCGCTCCACCAGCGCCGCCGTCCTGGAGGC<br>CCTCCGCGAGGCCCACCCCATCGTGGAGAAGATCCTGCAGTACCGGGAGCTCACCAAGC<br>TGAAGAGCACCTACATTGACCCCTTGCCGGACCTCATCCACCCCAGGACGGGCCGCCTC<br>CACACCCGCTTCAACCAGACGGCCACGGCCACGGGCAGGCTAAGTAGCTCCGATCCCAA<br>CCTCCAGAACATCCCCGTCCGCACCCCGCTTGGGCAGAGGATCCGCCGGGCCTTCATCG<br>CCGAGGAGGGTGGCTATTGGTGGCCCTGGACTATAGCCAGATAGAGCTCAGGGTGCTG<br>GCCCACCTCTCCGGCGACGAGAACCTGATCCGGGTCTTCCAGGAGGGCGGGACATCCA<br>CACGGAGACCGCCAGCTGGATGTTCGGCGTCCCCCGGGAGGCCGTGGACCCCCTGATGC<br>GCCGGGCGGCCAAGACCATCAACTTCGGGGTCCTCTACGGCATGTCGGCCCACCGCCTC<br>TCCCAGGAGCTAGCCATCCCTTACGAGGAGGCCCAGGCCTTCATTGAGCGCTACTTTCA<br>GAGCTTCCCCAAGGTGCGGGCCTGGATTGAGAAGACCCTGGAGGAGGGCAGGAGGCGGG<br>GGTACGTGGAGACCCTCTTCGGCCGCCGCCGCTACGTGCCAGACCTAGAGGCCCGGGTG<br>AAGAGCGTGCGGGAGGCGGCCGAGCGCATGGCCTTCAACATGCCCGTCCAGGGCACCGC<br>CGCCGACCTCATGAAGCTGGCTATGGTGAAGCTCTTCCCCAGGCTGGAGGAAATGGGGG<br>CCAGGATGCTCCTTCAGGTCCACGACGAGCTGGTCCTCGAGGCCCCAAAAGAGAGGGCG<br>GAGGCCGTGGCCCGGCTGGCCAAGGAGGTCATGGAGGGGGTGTATCCCCTGGCCGTGCC<br>CCTGGAGGTGGAGGTGGGGATAGGGGAGGACTGGCTCTCCGCCAAGGAGTGA |
| 40 | amino acid sequence of Pae3192: Stoffel-Taq fusion protein (including poly-His tag) | MGHHHHHHHHHHSSGHIEGRHMSKKQKLKFYDIKAKQAFETDQYEVIEKQTARGPMMFA<br>VAKSPYTGIKVYRLLGKKKGGGVTSPKALEEAPWPPPEGAFVGFVLSRKEPMWADLLAL<br>AAARGGRVHRAPEPYKALRDLKEARGLLAKDLSVLALREGLGLPPGDDPMLLAYLLDPS<br>NTTPEGVARRYGGEWTEEAGERAALSERLFANLWGRLEGEERLLWLYREVERPLSAVLA<br>HMEATGVRLDVAYLRALSLEVAEEIARLEAEVFRLAGHPFNLNSRDQLERVLFDELGLP<br>AIGKTEKTGKRSTSAAVLEALREAHPIVEKILQYRELTKLKSTYIDPLPDLIHPRTGRL<br>HTRFNQTATATGRLSSSDPNLQNIPVRTPLGQRIRRAFIAEEGWLLVALDYSQIELRVL<br>AHLSGDENLIRVFQEGRDIHTETASWMFGVPREAVDPLMRRAAKTINFGVLYGMSAHRL<br>SQELAIPYEEAQAFIERYFQSFPKVRAWIEKTLEEGRRRGYVETLFGRRRYVPDLEARV<br>KSVREAAERMAFNMPVQGTAADLMKLAMVKLFPRLEEMGARMLLQVHDELVLEAPKERA<br>EAVARLAKEVMEGVYPLAVPLEVEVGIGEDWLSAKE |
| 41 | amino acid sequence of Pae3192: Stoffel-Taq fusion protein (after removal of poly-His tag) | HMSKKQKLKFYDIKAKQAFETDQYEVIEKQTARGPMMFA<br>VAKSPYTGIKVYRLLGKKKGGGVTSPKALEEAPWPPPEGAFVGFVLSRKEPMWADLLAL<br>AAARGGRVHRAPEPYKALRDLKEARGLLAKDLSVLALREGLGLPPGDDPMLLAYLLDPS<br>NTTPEGVARRYGGEWTEEAGERAALSERLFANLWGRLEGEERLLWLYREVERPLSAVLA<br>HMEATGVRLDVAYLRALSLEVAEEIARLEAEVFRLAGHPFNLNSRDQLERVLFDELGLP<br>AIGKTEKTGKRSTSAAVLEALREAHPIVEKILQYRELTKLKSTYIDPLPDLIHPRTGRL<br>HTRFNQTATATGRLSSSDPNLQNIPVRTPLGQRIRRAFIAEEGWLLVALDYSQIELRVL<br>AHLSGDENLIRVFQEGRDIHTETASWMFGVPREAVDPLMRRAAKTINFGVLYGMSAHRL<br>SQELAIPYEEAQAFIERYFQSFPKVRAWIEKTLEEGRRRGYVETLFGRRRYVPDLEARV<br>KSVREAAERMAFNMPVQGTAADLMKLAMVKLFPRLEEMGARMLLQVHDELVLEAPKERA<br>EAVARLAKEVMEGVYPLAVPLEVEVGIGEDWLSAKE |
| 42 | polynucleotide encoding Ape3192: Stoffel-Taq fusion protein (including poly-His tag) | ATGGGCCATCATCATCATCATCATCATCATCATCACAGCAGCGGCCATATCGAAGGTCG<br>TCATATGCCGAAGAAGGAGAAGATTAAGTTCTTCGACCTGGTCGCCAAGAAGTACTACG<br>AGACTGACAACTACGAAGTCGAGATTAAGGAGACTAAGCGCGGCAAGTTTCGCTTCGCC<br>AAAGCCAAGAGCCCGTACACCGGCAAGATCTTTCTATCGCGTGCTGGGCAAAGCCGGCG<br>CGGTGTCACTAGTCCCAAGGCCCTGGAGGAGGCCCCCTGGCCCCGCCGGAAGGGGCCT<br>TCGTGGGCTTTGTGCTTTCCCGCAAGGAGCCCATGTGGGCCGATCTTCTGGCCCTGGCC<br>GCCGCCAGGGGGGGCCGGGTCCACCGGGCCCCCGAGCCTTATAAAGCCCTCAGGGACCT<br>GAAGGAGGCGCGGGGGCTTCTCGCCAAAGACCTGAGCGTTCTGGCCCTGAGGGAAGGCC<br>TTGGCCTCCCGCCCGGCGACGACCCCATGCTCCTCGCCTACCTCCTGGACCCTTCCCAC<br>ACCACCCCCGAGGGGGTGGCCCGGCGCTACGGCGGGAGTGGACGGAGGAGGCGGGGGA<br>GCGGGCCGCCCCTTTCCGAGAGGCTCTTCGCCAACCTGTGGGGAGGCTTGAGGGGAGG<br>AGAGGCTCCTTTGGCTTTACCGGGAGGTGGAGAGGCCCCTTTCCGCTGCCTGTCCTGGCCCAC<br>ATGGAGGCCACGGGGGTGCGCCTGGACGTGGCCTATCTCAGGGCCTTGTCCCTGGAGGT<br>GGCCGAGGAGATCGCCCGCCTCGAGGCCGAGGTCTTCCGCCTGGCCGGCCACCCCTTCA<br>ACCTCAACTCCCGGGACCAGCTGGAAAGGGTCCTCTTTGACGAGCTAGGGCTTCCCGCC<br>ATCGGCAAGACGGAGAAGACCGGCAAGCGCTCCACCAGCGCCGCCGTCCTGGAGGCCCT<br>CCGCGAGGCCCACCCCATCGTGGAGAAGATCCTGCAGTACCGGGAGCTCACCAAGCTGA<br>AGAGCACCTACATTGACCCCTTGCCGGACCTCATCCACCCCAGGACGGGCCGCCTCCAC<br>ACCCGCTTCAACCAGACGGCCACGGCCACGGGCAGGCTAAGTAGCTCCGATCCCAACCT<br>CCAGAACATCCCCGTCCGCACCCCGCTTGGGCAGAGGATCCGCCGGGCCTTCATCGCCG<br>AGGAGGGTGGCTATTGGTGGCCCTGGACTATAGCCAGATAGAGCTCAGGGTGCTGGCC<br>CACCTCTCCGGCGACGAGAACCTGATCCGGGTCTTCCAGGAGGGCGGGACATCCACAC<br>GGAGACCGCCAGCTGGATGTTCGGCGTCCCCCGGGAGGCCGTGGACCCCCTGATGCGCC<br>GGGCGGCCAAGACCATCAACTTCGGGGTCCTCTACGGCATGTCGGCCCACCGCCTCTCC<br>CAGGAGCTAGCCATCCCTTACGAGGAGGCCCAGGCCTTCATTGAGCGCTACTTTCAGAG<br>CTTCCCCAAGGTGCGGGCCTGGATTGAGAAGACCCTGGAGGAGGGCAGGAGGCGGGGT<br>ACGTGGAGACCCTCTTCGGCCGCCGCCGCTACGTGCCAGACCTAGAGGCCCGGGTGAAG<br>AGCGTGCGGGAGGCGGCCGAGCGCATGGCCTTCAACATGCCCGTCCAGGGCACCGCCGC<br>CGACCTCATGAAGCTGGCTATGGTGAAGCTCTTCCCCAGGCTGGAGGAAATGGGGGCCA<br>GGATGCTCCTTCAGGTCCACGACGAGCTGGTCCTCGAGGCCCCAAAAGAGAGGGCGGAG<br>GCCGTGGCCCGGCTGGCCAAGGAGGTCATGGAGGGGGTGTATCCCCTGGCCGTGCCCCT<br>GGAGGTGGAGGTGGGGATAGGGGAGGACTGGCTCTCCGCCAAGGAGTGA |

TABLE OF SEQUENCES

| SEQ ID NO: | Brief Description | Sequence |
|---|---|---|
| 43 | amino acid sequence of Ape3192: Stoffel-Taq fusion protein (including poly-His tag) | MGHHHHHHHHHSSGHIEGRHMPKKEKIKFFDLVAKKYYETDNYEVEIKETKRGKFRFA KAKSPYTGKIFYRVLGKAGGGVTSPKALEEAPWPPPEGAFVGFVLSRKEPMWADLLALA AARGGRVHRAPEPYKALRDLKEARGLLAKDLSVLALREGLGLPPGDDPMLLAYLLDPSN TTPEGVARRYGGEWTEEAGERAALSERLFANLWGRLEGEERLLWLYREVERPLSAVLAH MEATGVRLDVAYLRALSLEVAEEIARLEAEVFRLAGHPFNLNSRDQLERVLFDELGLPA IGKTEKTGKRSTSAAVLEALREAHPIVEKILQYRELTKLKSTYIDPLPDLIHPRTGRLH TRFNQTATATGRLSSSDPNLQNIPVRTPLGQRIRRAFIAEEGWLLVALDYSQIELRVLA HLSGDENLIRVFQEGRDIHTETASWMFGVPREAVDPLMRRAAKTINFGVLYGMSAHRLS QELAIPYEEAQAFIERYFQSFPKVRAWIEKTLEEGRRRGYVETLFGRRRYVPDLEARVK SVREAAERMAFNMPVQGTAADLMKLAMVKLFPRLEEMGARMLLQVHDELVLEAPKERAE AVARLAKEVMEGVYPLAVPLEVEVGIGEDWLSAKE |
| 44 | amino acid sequence of Ape3192: Stoffel-Taq fusion protein (after removal of poly-His tag) | HMPKKEKIKFFDLVAKKYYETDNYEVEIKETKRGKFRFA KAKSPYTGKIFYRVLGKAGGGVTSPKALEEAPWPPPEGAFVGFVLSRKEPMWADLLALA AARGGRVHRAPEPYKALRDLKEARGLLAKDLSVLALREGLGLPPGDDPMLLAYLLDPSN TTPEGVARRYGGEWTEEAGERAALSERLFANLWGRLEGEERLLWLYREVERPLSAVLAH MEATGVRLDVAYLRALSLEVAEEIARLEAEVFRLAGHPFNLNSRDQLERVLFDELGLPA IGKTEKTGKRSTSAAVLEALREAHPIVEKILQYRELTKLKSTYIDPLPDLIHPRTGRLH TRFNQTATATGRLSSSDPNLQNIPVRTPLGQRIRRAFIAEEGWLLVALDYSQIELRVLA HLSGDENLIRVFQEGRDIHTETASWMFGVPREAVDPLMRRAAKTINFGVLYGMSAHRLS QELAIPYEEAQAFIERYFQSFPKVRAWIEKTLEEGRRRGYVETLFGRRRYVPDLEARVK SVREAAERMAFNMPVQGTAADLMKLAMVKLFPRLEEMGARMLLQVHDELVLEAPKERAE AVARLAKEVMEGVYPLAVPLEVEVGIGEDWLSAKE |
| 45 | exemplary PCR "forward" primer | ggaagtacagctcagagttctgcagcaccctgc |
| 46 | exemplary PCR "reverse" primer | gatgcgaaactgaggctggctgtactgtctc |

The invention claimed is:

1. A method of increasing the processivity of a DNA polymerase comprising fusing the DNA polymerase to a polypeptide having at least 95% identity to SEQ ID NO:1, wherein the polypeptide has nucleic acid binding activity.

2. A method of increasing the processivity of a DNA polymerase comprising combining a reaction mixture comprising the DNA polymerase with a polypeptide comprising an amino acid sequence having at least 95% identity to SEQ ID NO:1, wherein the polypeptide has nucleic acid binding activity.

3. The method of claim 1 or 2, wherein the polypeptide comprises the amino acid sequence of SEQ ID NO:1 or a fragment of SEQ ID NO:1 that has nucleic acid binding activity.

4. The method of claim 1, wherein the polypeptide has double-stranded nucleic acid binding activity.

5. The method of claim 1, wherein the DNA polymerase is thermostable.

6. The method of claim 1, wherein the polypeptide has a basic isoelectric point.

7. The method of claim 1, wherein the polypeptide promotes annealing of complementary nucleic acid strands.

8. The method of claim 1, wherein the DNA polymerase lacks 5'-3' exonuclease activity.

9. The method of claim 1, wherein the DNA polymerase is selected from the group consisting of Taq polymerase, Tne polymerase, Tma polymerase, Tfi polymerase, Tth polymerase, and Pfu polymerase.

10. The method of claim 1, wherein the DNA polymerase and the polypeptide are fused by a linker.

11. The method of claim 1, wherein the processivity of the DNA polymerase is increased in a primer extension reaction.

12. The method of claim 11, wherein the primer extension reaction is a polymerase chain reaction (PCR).

13. The method of claim 12, wherein the PCR is hot start PCR.

14. The method of claim 2, wherein the polypeptide has double-stranded nucleic acid binding activity.

15. The method of claim 2, wherein the DNA polymerase is thermostable.

16. The method of claim 2, wherein the polypeptide has a basic isoelectric point.

17. The method of claim 2, wherein the polypeptide promotes annealing of complementary nucleic acid strands.

18. The method of claim 2, wherein the DNA polymerase lacks 5'-3' exonuclease activity.

19. The method of claim 2, wherein the DNA polymerase is selected from the group consisting of Taq polymerase, Tne polymerase, Tma polymerase, Tfi polymerase, Tth polymerase, and Pfu polymerase.

20. The method of claim 2, wherein the processivity of the DNA polymerase is increased in a primer extension reaction.

21. The method of claim 20, wherein the primer extension reaction is a polymerase chain reaction (PCR).

22. The method of claim 21, wherein the PCR is hot start PCR.

* * * * *

SEQUENCE LISTING

<160> NUMBER OF SEQ ID NOS: 53

<210> SEQ ID NO 1
<211> LENGTH: 57
<212> TYPE: PRT
<213> ORGANISM: Pyrobaculum aerophilum

<400> SEQUENCE: 1

Met Ser Lys Lys Gln Lys Leu Lys Phe Tyr Asp Ile Lys Ala Lys Gln
1               5                   10                  15

Ala Phe Glu Thr Asp Gln Tyr Glu Val Ile Glu Lys Gln Thr Ala Arg
            20                  25                  30

Gly Pro Met Met Phe Ala Val Ala Lys Ser Pro Tyr Thr Gly Ile Lys
        35                  40                  45

Val Tyr Arg Leu Leu Gly Lys Lys Lys
    50                  55

<210> SEQ ID NO 2
<211> LENGTH: 174
<212> TYPE: DNA
<213> ORGANISM: Pyrobaculum aerophilum

<400> SEQUENCE: 2
atgtccaaga agcagaaact aaagttctac gacataaagg cgaagcaggc gtttgagact      60
gaccagtacg aggttattga gaagcagact gcccgcggtc cgatgatgtt cgccgtggcc     120
aaatcgccgt acaccggcat aaaagtatac agactgttag gcaagaagaa ataa           174

<210> SEQ ID NO 3
<211> LENGTH: 174

```
<212> TYPE: DNA
<213> ORGANISM: Pyrobaculum aerophilum

<400> SEQUENCE: 3
atgtccaaga agcagaaact aaagttctac gacataaagg cgaagcaggc gtttgagact      60
gaccagtacg aggttattga gaagcagact gcccgcggtc cgatgatgtt cgccgtggcc     120
aaatcgccgt acaccggcat aaaagtatac agactattag gcaagaagaa ataa           174

<210> SEQ ID NO 4
<211> LENGTH: 56
<212> TYPE: PRT
<213> ORGANISM: Pyrobaculum aerophilum

<400> SEQUENCE: 4

Met Ala Lys Gln Lys Leu Lys Phe Tyr Asp Ile Lys Ala Lys Gln Ser
1               5                   10                  15

Phe Glu Thr Asp Lys Tyr Glu Val Ile Glu Lys Glu Thr Ala Arg Gly
                20                  25                  30

Pro Met Leu Phe Ala Val Ala Thr Ser Pro Tyr Thr Gly Ile Lys Val
            35                  40                  45

Tyr Arg Leu Leu Gly Lys Lys Lys
        50                  55

<210> SEQ ID NO 5
<211> LENGTH: 171
<212> TYPE: DNA
<213> ORGANISM: Pyrobaculum aerophilum

<400> SEQUENCE: 5
atggccaaac aaaaactaaa gttctacgac ataaaagcga acagtccttc gaaacggac       60 aaatacgagg tcattgagaa agacggcc cgcgggccga tgttatttgc agtggcaacc      120
tcgccgtaca ctggcataaa ggtgtacaga ctgttaggca agaagaaata a              171

<210> SEQ ID NO 6
<211> LENGTH: 56
<212> TYPE: PRT
<213> ORGANISM: Aeropyrum pernix

<400> SEQUENCE: 6

Met Pro Lys Lys Glu Lys Ile Lys Phe Phe Asp Leu Val Ala Lys Lys
1               5                   10                  15

Tyr Tyr Glu Thr Asp Asn Tyr Glu Val Glu Ile Lys Glu Thr Lys Arg
                20                  25                  30

Gly Lys Phe Arg Phe Ala Lys Ala Lys Ser Pro Tyr Thr Gly Lys Ile
            35                  40                  45

Phe Tyr Arg Val Leu Gly Lys Ala
        50                  55

<210> SEQ ID NO 7
<211> LENGTH: 171
<212> TYPE: DNA
<213> ORGANISM: Aeropyrum pernix

<400> SEQUENCE: 7
atgcccaaga aggagaagat aaagttcttc gacctagtcg ccaagaagta ctacgagact      60
gacaactacg aagtcgagat aaaggagact aagaggggca gtttaggtt cgccaaagcc     120 aagagcccgt acaccggcaa gatcttctat agagtgctag gcaaagccta g              171
```

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atgtccaaga agcagaaact gaagttctac gacattaagg cgaagcaggc gtttgag        57

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
accgaccagt acgaggttat tgagaagcag accgcccgcg gtccgatgat gttcgcc        57

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gtggccaaat cgccgtacac cggcattaaa gtgtaccgcc tgttaggcaa gaagaaataa    60

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtactggtcg gtctcaaacg cctg        24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cgatttggcc acggcgaaca tcat        24

<210> SEQ ID NO 13
<211> LENGTH: 174
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
atgtccaaga agcagaaact gaagttctac gacattaagg cgaagcaggc gtttgagacc    60
gaccagtacg aggttattga gaagcagacc gcccgcggtc cgatgatgtt cgccgtggcc    120
aaatcgccgt acaccggcat taaagtgtac cgcctgttag gcaagaagaa ataa     174

<210> SEQ ID NO 14
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
atgccgaaga aggagaagat taagttcttc gacctggtcg ccaagaagta ctacgag     57

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actgacaact acgaagtcga gattaaggag actaagcgcg gcaagtttcg cttcgcc     57

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
aaagccaaga gcccgtacac cggcaagatc ttctatcgcg tgctgggcaa agcctag     57

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtagttgtca gtctcgtagt actt     24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gctcttggct ttggcgaagc gaaa     24

<210> SEQ ID NO 19
<211> LENGTH: 171
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
atgccgaaga aggagaagat taagttcttc gacctggtcg ccaagaagta ctacgagact      60
gacaactacg aagtcgagat taaggagact aagcgcggca agtttcgctt cgccaaagcc     120
aagagcccgt acaccggcaa gatcttctat cgcgtgctgg gcaaagccta g              171

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtaaaacgac ggccagt                                                     17

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtaaaacgtc ggccagt                                                     17

<210> SEQ ID NO 22
<211> LENGTH: 2588
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
ccatgggcca tcatcatcat catcatcatc atcatcacag cagcggccat atcgaaggtc      60
gtcatatgat tttagatgtg gattacataa ctgaagaagg aaaacctgtt attaggctat     120
tcaaaaaaga gaacggaaaa tttaagatag agcatgatag aacttttaga ccatacattt     180
acgctcttct cagggatgat tcaaagattg aagaagttaa gaaaataacg ggggaaaggc     240
atggaaagat tgtgagaatt gttgatgtag agaaggttga gaaaaagttt ctcggcaagc     300
ctattaccgt gtggaaactt tatttggaac atccccaaga tgttcccact attagagaaa     360
aagttagaga acatccagca gttgtggaca tcttcgaata cgatattcca tttgcaaaga     420
gatacctcat cgacaaaggc ctaataccaa tggaggggga agaagagcta aagattcttg     480
ccttcgatat agaaacctc tatcacgaag gagaagagtt tggaaaaggc ccaattataa      540
tgattagtta tgcagatgaa aatgaagcaa aggtgattac ttggaaaaac atagatcttc     600
catacgttga ggttgtatca agcgagagag atgataaa gagatttctc aggattatca      660
gggagaagga tcctgacatt atagttactt ataatggaga ctcattcgac ttcccatatt     720
tagcgaaaag ggcagaaaaa cttgggatta aattaaccat tggaagagat ggaagcgagc     780
ccaagatgca gagaataggc gatatgacgg ctgtagaagt caaggaagaa atacattcg      840 acttgtatca tgtaataaca aggacaataa atctcccaac atacacacta gaggctgtat     900
atgaagcaat ttttggaaag ccaaaggaga aggtatacgc cgacgagata gcaaaagcct     960
gggaaagtgg agagaacctt gagagagttg ccaaatactc gatggaagat gcaaaggcaa    1020
cttatgaact cggaaagaa ttccttccaa tggaaattca gctttcaaga ttagttggac     1080
```

```
aacctttatg ggatgtttca aggtcaagca cagggaacct tgtagagtgg ttcttactta    1140
ggaaagccta cgaaagaaac gaagtagctc caaacaagcc aagtgaagag gagtatcaaa    1200
gaaggctcag ggagagctac acaggtggat tcgttaaaga gccagaaaag gggttgtggg    1260
aaaacatagt ataccctagat tttagagccc tatatccctc gattataatt acccacaatg    1320
tttctcccga tactctaaat cttgagggat gcaagaacta tgatatcgct cctcaagtag    1380
gccacaagtt ctgcaaggac atccctggtt ttataccaag tctcttggga catttgttag    1440
aggaaagaca aagattaag acaaaaatga aggaaactca agatcctata gaaaaaatac    1500
tccttgacta tagacaaaaa gcgataaaac tcttagcaaa ttctttctac ggatattatg    1560
gctatgcaaa agcaagatgg tactgtaagg agtgtgctga gagcgttact gcctggggaa    1620
gaaagtacat cgagttagta tggaaggagc tcgaagaaaa gtttggattt aaagtcctct    1680
acattgacac tgatggtctc tatgcaacta tcccaggagg agaaagtgag gaaataaaga    1740
aaaaggctct agaatttgta aaatacataa attcaaagct ccctggactg ctagagcttg    1800
aatatgaagg gttttataag agggggattct tcgttacgaa gaagagggtat gcagtaatag    1860 atgaagaagg aaaagtcatt actcgtggtt tagagatagt taggagagat tggagtgaaa    1920
ttgcaaaaga aactcaagct agagttttgg agacaatact aaaacacgga gatgttgaag    1980
aagctgtgag aatagtaaaa gaagtaatac aaaagcttgc caattatgaa attccaccag    2040
agaagctcgc aatatatgag cagataacaa gaccattaca tgagtataag gcgataggtc    2100
ctcacgtagc tgttgcaaag aaactagctg ctaaaggagt taaaataaag ccaggaatgg    2160
taattggata catagtactt agaggcgatg gtccaattag caatagggca attctagctg    2220
aggaatacga tcccaaaaag cacaagtatg acgcagaata ttacattgag aaccaggttc    2280
ttccagcggt acttaggata ttggagggat ttggatacag aaaggaagac ctcagatacc    2340
aaaagacaag acaagtcggc ctaacttcct ggcttaacat taaaaaatcc ggtaccggcg    2400
gtggcggtat gtccaagaag cagaaactga agttctacga cattaaggcg aagcaggcgt    2460
ttgagaccga ccagtacgag gttattgaga agcagaccgc ccgcggtccg atgatgttcg    2520
ccgtggccaa atcgccgtac accggcatta agtgtaccg cctgttaggc aagaagaaat    2580
aactcgag                                                             2588
```

<210> SEQ ID NO 23
<211> LENGTH: 859
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 23

```
Met Gly His His His His His His His His His Ser Ser Gly His
 1               5                  10                  15

Ile Glu Gly Arg His Met Ile Leu Asp Val Asp Tyr Ile Thr Glu Glu
                20                  25                  30

Gly Lys Pro Val Ile Arg Leu Phe Lys Lys Glu Asn Gly Lys Phe Lys
            35                  40                  45

Ile Glu His Asp Arg Thr Phe Arg Pro Tyr Ile Tyr Ala Leu Leu Arg
        50                  55                  60

Asp Asp Ser Lys Ile Glu Glu Val Lys Lys Ile Thr Gly Glu Arg His
 65                  70                  75                  80

Gly Lys Ile Val Arg Ile Val Asp Val Glu Lys Val Glu Lys Lys Phe
```

```
                        85                  90                  95
Leu Gly Lys Pro Ile Thr Val Trp Lys Leu Tyr Leu Glu His Pro Gln
                100                 105                 110

Asp Val Pro Thr Ile Arg Glu Lys Val Arg Glu His Pro Ala Val Val
            115                 120                 125

Asp Ile Phe Glu Tyr Asp Ile Pro Phe Ala Lys Arg Tyr Leu Ile Asp
        130                 135                 140

Lys Gly Leu Ile Pro Met Glu Gly Glu Glu Leu Lys Ile Leu Ala
145                 150                 155                 160

Phe Asp Ile Glu Thr Leu Tyr His Glu Gly Glu Glu Phe Gly Lys Gly
                165                 170                 175

Pro Ile Ile Met Ile Ser Tyr Ala Asp Glu Asn Glu Ala Lys Val Ile
                180                 185                 190

Thr Trp Lys Asn Ile Asp Leu Pro Tyr Val Glu Val Ser Ser Glu
            195                 200                 205

Arg Glu Met Ile Lys Arg Phe Leu Arg Ile Ile Arg Glu Lys Asp Pro
    210                 215                 220

Asp Ile Ile Val Thr Tyr Asn Gly Asp Ser Phe Asp Phe Pro Tyr Leu
225                 230                 235                 240

Ala Lys Arg Ala Glu Lys Leu Gly Ile Lys Leu Thr Ile Gly Arg Asp
                245                 250                 255

Gly Ser Glu Pro Lys Met Gln Arg Ile Gly Asp Met Thr Ala Val Glu
            260                 265                 270

Val Lys Gly Arg Ile His Phe Asp Leu Tyr His Val Ile Thr Arg Thr
        275                 280                 285

Ile Asn Leu Pro Thr Tyr Thr Leu Glu Ala Val Tyr Glu Ala Ile Phe
290                 295                 300

Gly Lys Pro Lys Glu Lys Val Tyr Ala Asp Glu Ile Ala Lys Ala Trp
305                 310                 315                 320

Glu Ser Gly Glu Asn Leu Glu Arg Val Ala Lys Tyr Ser Met Glu Asp
                325                 330                 335

Ala Lys Ala Thr Tyr Glu Leu Gly Lys Glu Phe Leu Pro Met Glu Ile
            340                 345                 350

Gln Leu Ser Arg Leu Val Gly Gln Pro Leu Trp Asp Val Ser Arg Ser
        355                 360                 365

Ser Thr Gly Asn Leu Val Glu Trp Phe Leu Leu Arg Lys Ala Tyr Glu
    370                 375                 380

Arg Asn Glu Val Ala Pro Asn Lys Pro Ser Glu Glu Glu Tyr Gln Arg
385                 390                 395                 400

Arg Leu Arg Glu Ser Tyr Thr Gly Gly Phe Val Lys Glu Pro Glu Lys
                405                 410                 415

Gly Leu Trp Glu Asn Ile Val Tyr Leu Asp Phe Arg Ala Leu Tyr Pro
            420                 425                 430

Ser Ile Ile Ile Thr His Asn Val Ser Pro Asp Thr Leu Asn Leu Glu
        435                 440                 445

Gly Cys Lys Asn Tyr Asp Ile Ala Pro Gln Val Gly His Lys Phe Cys
    450                 455                 460

Lys Asp Ile Pro Gly Phe Ile Pro Ser Leu Leu Gly His Leu Leu Glu
465                 470                 475                 480

Glu Arg Gln Lys Ile Lys Thr Lys Met Lys Glu Thr Gln Asp Pro Ile
                485                 490                 495

Glu Lys Ile Leu Leu Asp Tyr Arg Gln Lys Ala Ile Lys Leu Leu Ala
            500                 505                 510
```

Asn Ser Phe Tyr Gly Tyr Tyr Gly Tyr Ala Lys Ala Arg Trp Tyr Cys
            515                 520                 525

Lys Glu Cys Ala Glu Ser Val Thr Ala Trp Gly Arg Lys Tyr Ile Glu
    530                 535                 540

Leu Val Trp Lys Glu Leu Glu Glu Lys Phe Gly Phe Lys Val Leu Tyr
545                 550                 555                 560

Ile Asp Thr Asp Gly Leu Tyr Ala Thr Ile Pro Gly Gly Ser Glu
            565                 570                 575

Glu Ile Lys Lys Lys Ala Leu Glu Phe Val Lys Tyr Ile Asn Ser Lys
            580                 585                 590

Leu Pro Gly Leu Glu Leu Glu Tyr Glu Gly Phe Tyr Lys Arg Gly
        595                 600                 605

Phe Phe Val Thr Lys Lys Arg Tyr Ala Val Ile Asp Glu Glu Gly Lys
        610                 615                 620

Val Ile Thr Arg Gly Leu Glu Ile Val Arg Arg Asp Trp Ser Glu Ile
625                 630                 635                 640

Ala Lys Glu Thr Gln Ala Arg Val Leu Glu Thr Ile Leu Lys His Gly
                645                 650                 655

Asp Val Glu Glu Ala Val Arg Ile Val Lys Glu Val Ile Gln Lys Leu
            660                 665                 670

Ala Asn Tyr Glu Ile Pro Pro Glu Lys Leu Ala Ile Tyr Glu Gln Ile
            675                 680                 685

Thr Arg Pro Leu His Glu Tyr Lys Ala Ile Gly Pro His Val Ala Val
    690                 695                 700

Ala Lys Lys Leu Ala Ala Lys Gly Val Lys Ile Lys Pro Gly Met Val
705                 710                 715                 720

Ile Gly Tyr Ile Val Leu Arg Gly Asp Gly Pro Ile Ser Asn Arg Ala
                725                 730                 735

Ile Leu Ala Glu Glu Tyr Asp Pro Lys Lys His Lys Tyr Asp Ala Glu
            740                 745                 750

Tyr Tyr Ile Glu Asn Gln Val Leu Pro Ala Val Leu Arg Ile Leu Glu
            755                 760                 765

Gly Phe Gly Tyr Arg Lys Glu Asp Leu Arg Tyr Gln Lys Thr Arg Gln
    770                 775                 780

Val Gly Leu Thr Ser Trp Leu Asn Ile Lys Lys Ser Gly Thr Gly Gly
785                 790                 795                 800

Gly Gly Met Ser Lys Lys Gln Lys Leu Lys Phe Tyr Asp Ile Lys Ala
                805                 810                 815

Lys Gln Ala Phe Glu Thr Asp Gln Tyr Glu Val Ile Glu Lys Gln Thr
            820                 825                 830

Ala Arg Gly Pro Met Met Phe Ala Val Ala Lys Ser Pro Tyr Thr Gly
        835                 840                 845

Ile Lys Val Tyr Arg Leu Leu Gly Lys Lys
    850                 855

<210> SEQ ID NO 24
<211> LENGTH: 839
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 24

His Met Ile Leu Asp Val Asp Tyr Ile Thr Glu Glu Gly Lys Pro Val

```
            1               5                   10                  15
        Ile Arg Leu Phe Lys Lys Glu Asn Gly Lys Phe Lys Ile Glu His Asp
                        20                  25                  30
        Arg Thr Phe Arg Pro Tyr Ile Tyr Ala Leu Leu Arg Asp Asp Ser Lys
                        35                  40                  45
        Ile Glu Glu Val Lys Lys Ile Thr Gly Glu Arg His Gly Lys Ile Val
        50                      55                  60
        Arg Ile Val Asp Val Glu Lys Val Glu Lys Lys Phe Leu Gly Lys Pro
        65                      70                  75                  80
        Ile Thr Val Trp Lys Leu Tyr Leu Glu His Pro Gln Asp Val Pro Thr
                        85                  90                  95
        Ile Arg Glu Lys Val Arg Glu His Pro Ala Val Val Asp Ile Phe Glu
                        100                 105                 110
        Tyr Asp Ile Pro Phe Ala Lys Arg Tyr Leu Ile Asp Lys Gly Leu Ile
                        115                 120                 125
        Pro Met Glu Gly Glu Glu Leu Lys Ile Leu Ala Phe Asp Ile Glu
                        130                 135                 140
        Thr Leu Tyr His Glu Gly Glu Glu Phe Gly Lys Gly Pro Ile Ile Met
        145                     150                 155                 160
        Ile Ser Tyr Ala Asp Glu Asn Glu Ala Lys Val Ile Thr Trp Lys Asn
                        165                 170                 175
        Ile Asp Leu Pro Tyr Val Glu Val Val Ser Ser Glu Arg Glu Met Ile
                        180                 185                 190
        Lys Arg Phe Leu Arg Ile Ile Arg Glu Lys Asp Pro Asp Ile Ile Val
                        195                 200                 205
        Thr Tyr Asn Gly Asp Ser Phe Asp Phe Pro Tyr Leu Ala Lys Arg Ala
        210                     215                 220
        Glu Lys Leu Gly Ile Lys Leu Thr Ile Gly Arg Asp Gly Ser Glu Pro
        225                     230                 235                 240
        Lys Met Gln Arg Ile Gly Asp Met Thr Ala Val Glu Val Lys Gly Arg
                        245                 250                 255
        Ile His Phe Asp Leu Tyr His Val Ile Thr Arg Thr Ile Asn Leu Pro
                        260                 265                 270
        Thr Tyr Thr Leu Glu Ala Val Tyr Glu Ala Ile Phe Gly Lys Pro Lys
                        275                 280                 285
        Glu Lys Val Tyr Ala Asp Glu Ile Ala Lys Ala Trp Glu Ser Gly Glu
                        290                 295                 300
        Asn Leu Glu Arg Val Ala Lys Tyr Ser Met Glu Asp Ala Lys Ala Thr
        305                     310                 315                 320
        Tyr Glu Leu Gly Lys Glu Phe Leu Pro Met Glu Ile Gln Leu Ser Arg
                        325                 330                 335
        Leu Val Gly Gln Pro Leu Trp Asp Val Ser Arg Ser Ser Thr Gly Asn
                        340                 345                 350
        Leu Val Glu Trp Phe Leu Leu Arg Lys Ala Tyr Glu Arg Asn Glu Val
                        355                 360                 365
        Ala Pro Asn Lys Pro Ser Glu Glu Tyr Gln Arg Arg Leu Arg Glu
                        370                 375                 380
        Ser Tyr Thr Gly Gly Phe Val Lys Glu Pro Glu Lys Gly Leu Trp Glu
        385                     390                 395                 400
        Asn Ile Val Tyr Leu Asp Phe Arg Ala Leu Tyr Pro Ser Ile Ile Ile
                        405                 410                 415
        Thr His Asn Val Ser Pro Asp Thr Leu Asn Leu Glu Gly Cys Lys Asn
                        420                 425                 430
```

```
Tyr Asp Ile Ala Pro Gln Val Gly His Lys Phe Cys Lys Asp Ile Pro
        435                 440                 445

Gly Phe Ile Pro Ser Leu Leu Gly His Leu Leu Glu Glu Arg Gln Lys
450                 455                 460

Ile Lys Thr Lys Met Lys Glu Thr Gln Asp Pro Ile Glu Lys Ile Leu
465                 470                 475                 480

Leu Asp Tyr Arg Gln Lys Ala Ile Lys Leu Leu Ala Asn Ser Phe Tyr
                485                 490                 495

Gly Tyr Tyr Gly Tyr Ala Lys Ala Arg Trp Tyr Cys Lys Glu Cys Ala
                500                 505                 510

Glu Ser Val Thr Ala Trp Gly Arg Lys Tyr Ile Glu Leu Val Trp Lys
            515                 520                 525

Glu Leu Glu Glu Lys Phe Gly Phe Lys Val Leu Tyr Ile Asp Thr Asp
            530                 535                 540

Gly Leu Tyr Ala Thr Ile Pro Gly Gly Glu Ser Glu Glu Ile Lys Lys
545                 550                 555                 560

Lys Ala Leu Glu Phe Val Lys Tyr Ile Asn Ser Lys Leu Pro Gly Leu
                565                 570                 575

Leu Glu Leu Glu Tyr Glu Gly Phe Tyr Lys Arg Gly Phe Phe Val Thr
                580                 585                 590

Lys Lys Arg Tyr Ala Val Ile Asp Glu Glu Gly Lys Val Ile Thr Arg
            595                 600                 605

Gly Leu Glu Ile Val Arg Arg Asp Trp Ser Glu Ile Ala Lys Glu Thr
610                 615                 620

Gln Ala Arg Val Leu Glu Thr Ile Leu Lys His Gly Asp Val Glu Glu
625                 630                 635                 640

Ala Val Arg Ile Val Lys Glu Val Ile Gln Lys Leu Ala Asn Tyr Glu
                645                 650                 655

Ile Pro Pro Glu Lys Leu Ala Ile Tyr Glu Gln Ile Thr Arg Pro Leu
                660                 665                 670

His Glu Tyr Lys Ala Ile Gly Pro His Val Ala Val Ala Lys Lys Leu
            675                 680                 685

Ala Ala Lys Gly Val Lys Ile Lys Pro Gly Met Val Ile Gly Tyr Ile
690                 695                 700

Val Leu Arg Gly Asp Gly Pro Ile Ser Asn Arg Ala Ile Leu Ala Glu
705                 710                 715                 720

Glu Tyr Asp Pro Lys Lys His Lys Tyr Asp Ala Glu Tyr Tyr Ile Glu
                725                 730                 735

Asn Gln Val Leu Pro Ala Val Leu Arg Ile Leu Glu Gly Phe Gly Tyr
                740                 745                 750

Arg Lys Glu Asp Leu Arg Tyr Gln Lys Thr Arg Gln Val Gly Leu Thr
            755                 760                 765

Ser Trp Leu Asn Ile Lys Lys Ser Gly Thr Gly Gly Gly Met Ser
770                 775                 780

Lys Lys Gln Lys Leu Lys Phe Tyr Asp Ile Lys Ala Lys Gln Ala Phe
785                 790                 795                 800

Glu Thr Asp Gln Tyr Glu Val Ile Glu Lys Gln Thr Ala Arg Gly Pro
                805                 810                 815

Met Met Phe Ala Val Ala Lys Ser Pro Tyr Thr Gly Ile Lys Val Tyr
                820                 825                 830

Arg Leu Leu Gly Lys Lys Lys
            835
```

<210> SEQ ID NO 25
<211> LENGTH: 2582
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
ccatgggcca tcatcatcat catcatcatc atcatcacag cagcggccat atcgaaggtc      60
gtcatatgat tttagatgtg gattacataa ctgaagaagg aaaacctgtt attaggctat     120
tcaaaaaaga gaacggaaaa tttaagatag agcatgatag aactttagaa ccatacattt     180
acgctcttct cagggatgat tcaaagattg aagaagttaa gaaaataacg ggggaaaggc     240
atggaaagat tgtgagaatt gttgatgtag agaaggttga gaaaaagttt ctcggcaagc     300
ctattaccgt gtggaaactt tatttggaac atccccaaga tgttcccact attagagaaa     360
aagttagaga acatccagca gttgtggaca tcttcgaata cgatattcca tttgcaaaga     420
gatacctcat cgacaaaggc ctaataccaa tggaggggga agaagagcta aagattcttg     480
ccttcgatat agaaaccctc tatcacgaag gagaagagtt tggaaaaggc ccaattataa     540
tgattagtta tgcagatgaa atgaagcaa  aggtgattac ttggaaaaac atagatcttc     600
catacgttga ggttgtatca agcgagagag agatgataaa gagatttctc aggattatca     660
gggagaagga tcctgacatt atagttactt ataatggaga ctcattcgac ttcccatatt     720
tagcgaaaag ggcagaaaaa cttgggatta aattaaccat tggaagagat ggaagcgagc     780
ccaagatgca gagaataggc gatatgacgg ctgtagaagt caagggaaga atacatttcg     840
acttgtatca tgtaataaca aggacaataa atctcccaac atacacacta gaggctgtat     900
atgaagcaat ttttggaaag ccaaaggaga aggtatacgc cgacgagata gcaaaagcct     960
gggaaagtgg agagaacctt gagagagttg ccaaatactc gatggaagat gcaaaggcaa    1020
cttatgaact cgggaaagaa ttccttccaa tggaaattca gctttcaaga ttagttggac    1080
aacctttatg ggatgtttca aggtcaagca cagggaacct tgtagagtgg ttcttactta    1140
ggaaagccta cgaaagaaac gaagtagctc caaacaagcc aagtgaagag gagtatcaaa    1200
gaaggctcag ggagagctac acaggtggat tcgttaaaga gccagaaaag gggttgtggg    1260
aaaacatagt ataccttagat tttagagccc tatatccctc gattataatt acccacaatg    1320
tttctcccga tactctaaat cttgagggat gcaagaacta tgatatcgct cctcaagtag    1380
gccacaagtt ctgcaaggac atccctggtt ttataccaag tctcttggga catttgttag    1440
aggaaagaca aaagattaag acaaaaatga ggaaactca agatcctata gaaaaaatac    1500
tccttgacta tagacaaaaa gcgataaaac tcttagcaaa ttctttctac ggatatttatg    1560
gctatgcaaa agcaagatgg tactgtaagg agtgtgctga gagcgttact gcctggggaa    1620
gaaagtacat cgagttagta tggaaggagc tcgaagaaaa gtttggattt aaagtcctct    1680
acattgacac tgatggtctc tatgcaacta tcccaggagg agaaagtgag gaaataaaga    1740
aaaaggctct agaattgta aaatacataa attcaaagct ccctggactg ctagagcttg    1800
aatatgaagg gtttttataag aggggattct tcgttacgaa gaagaggtat gcagtaatag    1860
atgaagaagg aaaagtcatt actcgtggtt tagagatagt taggagagat tggagtgaaa    1920
ttgcaaaaga aactcaagct agagttttgg agacaatact aaaacacgga gatgttgaag    1980
aagctgtgag aatagtaaaa gaagtaatac aaaagcttgc caattatgaa attccaccag    2040
```

```
agaagctcgc aatatatgag cagataacaa gaccattaca tgagtataag gcgataggtc   2100
ctcacgtagc tgttgcaaag aaactagctg ctaaaggagt taaaataaag ccaggaatgg   2160
taattggata catagtactt agaggcgatg gtccaattag caatagggca attctagctg   2220
aggaatacga tcccaaaaag cacaagtatg acgcagaata ttacattgag aaccaggttc   2280
ttccagcggt acttaggata ttggagggat ttggatacag aaaggaagac ctcagatacc   2340
aaaagacaag acaagtcggc ctaacttcct ggcttaacat taaaaaatcc ggtaccggcg   2400
gtggcggtcc gaagaaggag aagattaggt tcttcgacct ggtcgccaag aagtactacg   2460
agactgacaa ctacgaagtc gagattaagg agactaagcg cggcaagttt cgcttcgcca   2520
aagccaagag cccgtacacc ggcaagatct tctatcgcgt gctgggcaaa gcctaactcg   2580
ag                                                                  2582
```

<210> SEQ ID NO 26
<211> LENGTH: 857
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 26

```
Met Gly His His His His His His His His Ser Ser Gly His
1               5                   10                  15

Ile Glu Gly Arg His Met Ile Leu Asp Val Asp Tyr Ile Thr Glu Glu
            20                  25                  30

Gly Lys Pro Val Ile Arg Leu Phe Lys Lys Glu Asn Gly Lys Phe Lys
        35                  40                  45

Ile Glu His Asp Arg Thr Phe Arg Pro Tyr Ile Tyr Ala Leu Leu Arg
    50                  55                  60

Asp Asp Ser Lys Ile Glu Glu Val Lys Lys Ile Thr Gly Glu Arg His
65                  70                  75                  80

Gly Lys Ile Val Arg Ile Val Asp Val Glu Lys Val Glu Lys Lys Phe
                85                  90                  95

Leu Gly Lys Pro Ile Thr Val Trp Lys Leu Tyr Leu Glu His Pro Gln
            100                 105                 110

Asp Val Pro Thr Ile Arg Glu Lys Val Arg Glu His Pro Ala Val Val
        115                 120                 125

Asp Ile Phe Glu Tyr Asp Ile Pro Phe Ala Lys Arg Tyr Leu Ile Asp
    130                 135                 140

Lys Gly Leu Ile Pro Met Glu Gly Glu Glu Leu Lys Ile Leu Ala
145                 150                 155                 160

Phe Asp Ile Glu Thr Leu Tyr His Glu Gly Glu Glu Phe Gly Lys Gly
                165                 170                 175

Pro Ile Ile Met Ile Ser Tyr Ala Asp Glu Asn Glu Ala Lys Val Ile
            180                 185                 190

Thr Trp Lys Asn Ile Asp Leu Pro Tyr Val Glu Val Val Ser Ser Glu
        195                 200                 205

Arg Glu Met Ile Lys Arg Phe Leu Arg Ile Ile Arg Glu Lys Asp Pro
    210                 215                 220

Asp Ile Ile Val Thr Tyr Asn Gly Asp Ser Phe Asp Phe Pro Tyr Leu
225                 230                 235                 240

Ala Lys Arg Ala Glu Lys Leu Gly Ile Lys Leu Thr Ile Gly Arg Asp
                245                 250                 255
```

```
Gly Ser Glu Pro Lys Met Gln Arg Ile Gly Asp Met Thr Ala Val Glu
            260                 265                 270

Val Lys Gly Arg Ile His Phe Asp Leu Tyr His Val Ile Thr Arg Thr
275                 280                 285

Ile Asn Leu Pro Thr Tyr Thr Leu Glu Ala Val Tyr Glu Ala Ile Phe
    290                 295                 300

Gly Lys Pro Lys Glu Lys Val Tyr Ala Asp Glu Ile Ala Lys Ala Trp
305                 310                 315                 320

Glu Ser Gly Glu Asn Leu Glu Arg Val Ala Lys Tyr Ser Met Glu Asp
                325                 330                 335

Ala Lys Ala Thr Tyr Glu Leu Gly Lys Glu Phe Leu Pro Met Glu Ile
            340                 345                 350

Gln Leu Ser Arg Leu Val Gly Gln Pro Leu Trp Asp Val Ser Arg Ser
            355                 360                 365

Ser Thr Gly Asn Leu Val Glu Trp Phe Leu Leu Arg Lys Ala Tyr Glu
    370                 375                 380

Arg Asn Glu Val Ala Pro Asn Lys Pro Ser Glu Glu Tyr Gln Arg
385                 390                 395                 400

Arg Leu Arg Glu Ser Tyr Thr Gly Gly Phe Val Lys Glu Pro Glu Lys
                405                 410                 415

Gly Leu Trp Glu Asn Ile Val Tyr Leu Asp Phe Arg Ala Leu Tyr Pro
            420                 425                 430

Ser Ile Ile Ile Thr His Asn Val Ser Pro Asp Thr Leu Asn Leu Glu
            435                 440                 445

Gly Cys Lys Asn Tyr Asp Ile Ala Pro Gln Val Gly His Lys Phe Cys
    450                 455                 460

Lys Asp Ile Pro Gly Phe Ile Pro Ser Leu Leu Gly His Leu Leu Glu
465                 470                 475                 480

Glu Arg Gln Lys Ile Lys Thr Lys Met Lys Glu Thr Gln Asp Pro Ile
                485                 490                 495

Glu Lys Ile Leu Leu Asp Tyr Arg Gln Lys Ala Ile Lys Leu Leu Ala
            500                 505                 510

Asn Ser Phe Tyr Gly Tyr Tyr Gly Tyr Ala Lys Ala Arg Trp Tyr Cys
    515                 520                 525

Lys Glu Cys Ala Glu Ser Val Thr Ala Trp Gly Arg Lys Tyr Ile Glu
530                 535                 540

Leu Val Trp Lys Glu Leu Glu Lys Phe Gly Phe Lys Val Leu Tyr
545                 550                 555                 560

Ile Asp Thr Asp Gly Leu Tyr Ala Thr Ile Pro Gly Gly Glu Ser Glu
                565                 570                 575

Glu Ile Lys Lys Lys Ala Leu Glu Phe Val Lys Tyr Ile Asn Ser Lys
            580                 585                 590

Leu Pro Gly Leu Leu Glu Leu Glu Tyr Glu Gly Phe Tyr Lys Arg Gly
    595                 600                 605

Phe Phe Val Thr Lys Lys Arg Tyr Ala Val Ile Asp Glu Glu Gly Lys
610                 615                 620

Val Ile Thr Arg Gly Leu Glu Ile Val Arg Arg Asp Trp Ser Glu Ile
625                 630                 635                 640

Ala Lys Glu Thr Gln Ala Arg Val Leu Glu Thr Ile Leu Lys His Gly
                645                 650                 655

Asp Val Glu Glu Ala Val Arg Ile Val Lys Glu Val Ile Gln Lys Leu
            660                 665                 670

Ala Asn Tyr Glu Ile Pro Pro Glu Lys Leu Ala Ile Tyr Glu Gln Ile
```

```
                    675                 680                 685
Thr Arg Pro Leu His Glu Tyr Lys Ala Ile Gly Pro His Val Ala Val
690                 695                 700

Ala Lys Lys Leu Ala Ala Lys Gly Val Lys Ile Lys Pro Gly Met Val
705                 710                 715                 720

Ile Gly Tyr Ile Val Leu Arg Gly Asp Gly Pro Ile Ser Asn Arg Ala
                725                 730                 735

Ile Leu Ala Glu Glu Tyr Asp Pro Lys Lys His Lys Tyr Asp Ala Glu
                740                 745                 750

Tyr Tyr Ile Glu Asn Gln Val Leu Pro Ala Val Leu Arg Ile Leu Glu
                755                 760                 765

Gly Phe Gly Tyr Arg Lys Glu Asp Leu Arg Tyr Gln Lys Thr Arg Gln
770                 775                 780

Val Gly Leu Thr Ser Trp Leu Asn Ile Lys Lys Ser Gly Thr Gly Gly
785                 790                 795                 800

Gly Gly Pro Lys Lys Glu Lys Ile Arg Phe Phe Asp Leu Val Ala Lys
                805                 810                 815

Lys Tyr Tyr Glu Thr Asp Asn Tyr Glu Val Glu Ile Lys Glu Thr Lys
                820                 825                 830

Arg Gly Lys Phe Arg Phe Ala Lys Ala Lys Ser Pro Tyr Thr Gly Lys
                835                 840                 845

Ile Phe Tyr Arg Val Leu Gly Lys Ala
                850                 855

<210> SEQ ID NO 27
<211> LENGTH: 837
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 27

His Met Ile Leu Asp Val Asp Tyr Ile Thr Glu Glu Gly Lys Pro Val
1               5                   10                  15

Ile Arg Leu Phe Lys Lys Glu Asn Gly Lys Phe Lys Ile Glu His Asp
                20                  25                  30

Arg Thr Phe Arg Pro Tyr Ile Tyr Ala Leu Leu Arg Asp Asp Ser Lys
            35                  40                  45

Ile Glu Glu Val Lys Lys Ile Thr Gly Glu Arg His Gly Lys Ile Val
50                  55                  60

Arg Ile Val Asp Val Glu Lys Val Glu Lys Lys Phe Leu Gly Lys Pro
65                  70                  75                  80

Ile Thr Val Trp Lys Leu Tyr Leu Glu His Pro Gln Asp Val Pro Thr
                85                  90                  95

Ile Arg Glu Lys Val Arg Glu His Pro Ala Val Val Asp Ile Phe Glu
            100                 105                 110

Tyr Asp Ile Pro Phe Ala Lys Arg Tyr Leu Ile Asp Lys Gly Leu Ile
        115                 120                 125

Pro Met Glu Gly Glu Glu Glu Leu Lys Ile Leu Ala Phe Asp Ile Glu
130                 135                 140

Thr Leu Tyr His Glu Gly Glu Glu Phe Gly Lys Gly Pro Ile Ile Met
145                 150                 155                 160

Ile Ser Tyr Ala Asp Glu Asn Glu Ala Lys Val Ile Thr Trp Lys Asn
                165                 170                 175
```

```
Ile Asp Leu Pro Tyr Val Glu Val Ser Ser Glu Arg Glu Met Ile
            180                 185                 190
Lys Arg Phe Leu Arg Ile Ile Arg Glu Lys Asp Pro Asp Ile Ile Val
195                 200                 205
Thr Tyr Asn Gly Asp Ser Phe Asp Phe Pro Tyr Leu Ala Lys Arg Ala
            210                 215                 220
Glu Lys Leu Gly Ile Lys Leu Thr Ile Gly Arg Asp Gly Ser Glu Pro
225                 230                 235                 240
Lys Met Gln Arg Ile Gly Asp Met Thr Ala Val Glu Val Lys Gly Arg
            245                 250                 255
Ile His Phe Asp Leu Tyr His Val Ile Thr Arg Thr Ile Asn Leu Pro
            260                 265                 270
Thr Tyr Thr Leu Glu Ala Val Tyr Glu Ala Ile Phe Gly Lys Pro Lys
            275                 280                 285
Glu Lys Val Tyr Ala Asp Glu Ile Ala Lys Ala Trp Glu Ser Gly Glu
            290                 295                 300
Asn Leu Glu Arg Val Ala Lys Tyr Ser Met Glu Asp Ala Lys Ala Thr
305                 310                 315                 320
Tyr Glu Leu Gly Lys Glu Phe Leu Pro Met Glu Ile Gln Leu Ser Arg
            325                 330                 335
Leu Val Gly Gln Pro Leu Trp Asp Val Ser Arg Ser Ser Thr Gly Asn
            340                 345                 350
Leu Val Glu Trp Phe Leu Leu Arg Lys Ala Tyr Glu Arg Asn Glu Val
            355                 360                 365
Ala Pro Asn Lys Pro Ser Glu Glu Tyr Gln Arg Arg Leu Arg Glu
370                 375                 380
Ser Tyr Thr Gly Gly Phe Val Lys Glu Pro Glu Lys Gly Leu Trp Glu
385                 390                 395                 400
Asn Ile Val Tyr Leu Asp Phe Arg Ala Leu Tyr Pro Ser Ile Ile Ile
            405                 410                 415
Thr His Asn Val Ser Pro Asp Thr Leu Asn Leu Glu Gly Cys Lys Asn
            420                 425                 430
Tyr Asp Ile Ala Pro Gln Val Gly His Lys Phe Cys Lys Asp Ile Pro
            435                 440                 445
Gly Phe Ile Pro Ser Leu Leu Gly His Leu Leu Glu Glu Arg Gln Lys
450                 455                 460
Ile Lys Thr Lys Met Lys Glu Thr Gln Asp Pro Ile Glu Lys Ile Leu
465                 470                 475                 480
Leu Asp Tyr Arg Gln Lys Ala Ile Lys Leu Leu Ala Asn Ser Phe Tyr
            485                 490                 495
Gly Tyr Tyr Gly Tyr Ala Lys Ala Arg Trp Tyr Cys Lys Glu Cys Ala
            500                 505                 510
Glu Ser Val Thr Ala Trp Gly Arg Lys Tyr Ile Glu Leu Val Trp Lys
            515                 520                 525
Glu Leu Glu Glu Lys Phe Gly Phe Lys Val Leu Tyr Ile Asp Thr Asp
            530                 535                 540
Gly Leu Tyr Ala Thr Ile Pro Gly Gly Glu Ser Glu Glu Ile Lys Lys
545                 550                 555                 560
Lys Ala Leu Glu Phe Val Lys Tyr Ile Asn Ser Lys Leu Pro Gly Leu
            565                 570                 575
Leu Glu Leu Glu Tyr Glu Gly Phe Tyr Lys Arg Gly Phe Phe Val Thr
            580                 585                 590
Lys Lys Arg Tyr Ala Val Ile Asp Glu Glu Gly Lys Val Ile Thr Arg
```

-continued

```
                595                 600                 605
Gly Leu Glu Ile Val Arg Arg Asp Trp Ser Glu Ile Ala Lys Glu Thr
        610                 615                 620
Gln Ala Arg Val Leu Glu Thr Ile Leu Lys His Gly Asp Val Glu Glu
625                 630                 635                 640
Ala Val Arg Ile Val Lys Glu Val Ile Gln Lys Leu Ala Asn Tyr Glu
                645                 650                 655
Ile Pro Pro Glu Lys Leu Ala Ile Tyr Glu Gln Ile Thr Arg Pro Leu
            660                 665                 670
His Glu Tyr Lys Ala Ile Gly Pro His Val Ala Val Ala Lys Lys Leu
        675                 680                 685
Ala Ala Lys Gly Val Lys Ile Lys Pro Gly Met Val Ile Gly Tyr Ile
690                 695                 700
Val Leu Arg Gly Asp Gly Pro Ile Ser Asn Arg Ala Ile Leu Ala Glu
705                 710                 715                 720
Glu Tyr Asp Pro Lys Lys His Lys Tyr Asp Ala Glu Tyr Tyr Ile Glu
                725                 730                 735
Asn Gln Val Leu Pro Ala Val Leu Arg Ile Leu Glu Gly Phe Gly Tyr
            740                 745                 750
Arg Lys Glu Asp Leu Arg Tyr Gln Lys Thr Arg Gln Val Gly Leu Thr
        755                 760                 765
Ser Trp Leu Asn Ile Lys Lys Ser Gly Thr Gly Gly Gly Pro Lys
770                 775                 780
Lys Glu Lys Ile Arg Phe Phe Asp Leu Val Ala Lys Lys Tyr Tyr Glu
785                 790                 795                 800
Thr Asp Asn Tyr Glu Val Glu Ile Lys Glu Thr Lys Arg Gly Lys Phe
                805                 810                 815
Arg Phe Ala Lys Ala Lys Ser Pro Tyr Thr Gly Lys Ile Phe Tyr Arg
            820                 825                 830
Val Leu Gly Lys Ala
        835
```

```
<210> SEQ ID NO 28
<211> LENGTH: 52
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)
<223> OTHER INFORMATION: Any amino acid
<220> FEATURE:
<221> NAME/KEY: MOD_RES
<222> LOCATION: (4)
<223> OTHER INFORMATION: Any amino acid
<220> FEATURE:
<221> NAME/KEY: MOD_RES
<222> LOCATION: (7)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (13)..(15)
<223> OTHER INFORMATION: Any amino acid
<220> FEATURE:
<221> NAME/KEY: MOD_RES
<222> LOCATION: (19)
<223> OTHER INFORMATION: Any amino acid
```

```
<220> FEATURE:
<221> NAME/KEY: MOD_RES
<222> LOCATION: (23)..(24)
<223> OTHER INFORMATION: Any amino acid
<220> FEATURE:
<221> NAME/KEY: MOD_RES
<222> LOCATION: (26)
<223> OTHER INFORMATION: Any amino acid
<220> FEATURE:
<221> NAME/KEY: MOD_RES
<222> LOCATION: (28)
<223> OTHER INFORMATION: Any amino acid
<220> FEATURE:
<221> NAME/KEY: MOD_RES
<222> LOCATION: (31)..(33)
<223> OTHER INFORMATION: Any amino acid
<220> FEATURE:
<221> NAME/KEY: MOD_RES
<222> LOCATION: (36)
<223> OTHER INFORMATION: Any amino acid
<220> FEATURE:
<221> NAME/KEY: MOD_RES
<222> LOCATION: (44)..(46)
<223> OTHER INFORMATION: Any amino acid
<220> FEATURE:
<221> NAME/KEY: MOD_RES
<222> LOCATION: (49)
<223> OTHER INFORMATION: Any amino acid

<400> SEQUENCE: 28

Lys Xaa Lys Xaa Lys Phe Xaa Asp Xaa Xaa Ala Lys Xaa Xaa Xaa Glu
 1               5                  10                  15

Thr Asp Xaa Tyr Glu Val Xaa Xaa Lys Xaa Thr Xaa Arg Gly Xaa Xaa
                20                  25                  30

Xaa Phe Ala Xaa Ala Lys Ser Pro Tyr Thr Gly Xaa Xaa Xaa Tyr Arg
            35                  40                  45

Xaa Leu Gly Lys
        50

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gttttcccag tcacgacgtt gtaaaacgac ggcc                              34

<210> SEQ ID NO 30
<211> LENGTH: 64
<212> TYPE: PRT
<213> ORGANISM: Sulfolobus solfataricus

<400> SEQUENCE: 30

Met Ala Thr Val Lys Phe Lys Tyr Lys Gly Glu Glu Lys Gln Val Asp
 1               5                  10                  15

Ile Ser Lys Ile Lys Lys Val Trp Arg Val Gly Lys Met Ile Ser Phe
                20                  25                  30

Thr Tyr Asp Glu Gly Gly Gly Lys Thr Gly Arg Gly Ala Val Ser Glu
            35                  40                  45

Lys Asp Ala Pro Lys Glu Leu Leu Gln Met Leu Glu Lys Gln Lys Lys
        50                  55                  60

<210> SEQ ID NO 31
<211> LENGTH: 775
```

<212> TYPE: PRT
<213> ORGANISM: Pyrococcus furiosus

<400> SEQUENCE: 31

```
Met Ile Leu Asp Val Asp Tyr Ile Thr Glu Glu Gly Lys Pro Val Ile
  1               5                  10                  15

Arg Leu Phe Lys Lys Glu Asn Gly Lys Phe Lys Ile Glu His Asp Arg
             20                  25                  30

Thr Phe Arg Pro Tyr Ile Tyr Ala Leu Leu Arg Asp Asp Ser Lys Ile
         35                  40                  45

Glu Glu Val Lys Lys Ile Thr Gly Glu Arg His Gly Lys Ile Val Arg
     50                  55                  60

Ile Val Asp Val Glu Lys Val Glu Lys Lys Phe Leu Gly Lys Pro Ile
 65                  70                  75                  80

Thr Val Trp Lys Leu Tyr Leu Glu His Pro Gln Asp Val Pro Thr Ile
                 85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400
```

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775

<210> SEQ ID NO 32
<211> LENGTH: 832
<212> TYPE: PRT
<213> ORGANISM: Thermus aquaticus

<400> SEQUENCE: 32

```
Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
        275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415
```

-continued

Trp Gly Arg Leu Glu Gly Glu Arg Leu Leu Trp Leu Tyr Arg Glu
         420                 425                 430

Val Glu Arg Pro Leu Ser Ala Val Leu Ala His Met Glu Ala Thr Gly
         435                 440                 445

Val Arg Leu Asp Val Ala Tyr Leu Arg Ala Leu Ser Leu Glu Val Ala
450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
             485                 490                 495

Glu Leu Gly Leu Pro Ala Ile Gly Lys Thr Glu Lys Thr Gly Lys Arg
             500                 505                 510

Ser Thr Ser Ala Ala Val Leu Glu Ala Leu Arg Glu Ala His Pro Ile
             515                 520                 525

Val Glu Lys Ile Leu Gln Tyr Arg Glu Leu Thr Lys Leu Lys Ser Thr
530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Gly Arg Leu Ser Ser
                 565                 570                 575

Ser Asp Pro Asn Leu Gln Asn Ile Pro Val Arg Thr Pro Leu Gly Gln
             580                 585                 590

Arg Ile Arg Arg Ala Phe Ile Ala Glu Glu Gly Trp Leu Leu Val Ala
             595                 600                 605

Leu Asp Tyr Ser Gln Ile Glu Leu Arg Val Leu Ala His Leu Ser Gly
             610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                 645                 650                 655

Leu Met Arg Arg Ala Ala Lys Thr Ile Asn Phe Gly Val Leu Tyr Gly
                 660                 665                 670

Met Ser Ala His Arg Leu Ser Gln Glu Leu Ala Ile Pro Tyr Glu Glu
                 675                 680                 685

Ala Gln Ala Phe Ile Glu Arg Tyr Phe Gln Ser Phe Pro Lys Val Arg
690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                 725                 730                 735

Val Lys Ser Val Arg Glu Ala Ala Glu Arg Met Ala Phe Asn Met Pro
             740                 745                 750

Val Gln Gly Thr Ala Ala Asp Leu Met Lys Leu Ala Met Val Lys Leu
             755                 760                 765

Phe Pro Arg Leu Glu Glu Met Gly Ala Arg Met Leu Leu Gln Val His
             770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                 805                 810                 815

Leu Glu Val Glu Val Gly Ile Gly Glu Asp Trp Leu Ser Ala Lys Glu
             820                 825                 830

<210> SEQ ID NO 33
<211> LENGTH: 2745
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

| | | | | | |
|---|---|---|---|---|---|
| atgggccatc | atcatcatca | tcatcatcat | catcacagca | gcggccatat | cgaaggtcgt | 60 |
| catatgtcca | agaagcagaa | actgaagttc | tacgacatta | aggcgaagca | ggcgtttgag | 120 |
| accgaccagt | acgaggttat | tgagaagcag | accgcccgcg | gtccgatgat | gttcgccgtg | 180 |
| gccaaatcgc | cgtacaccgg | cattaaagtg | taccgcctgt | taggcaagaa | gaaaggcggc | 240 |
| ggtgtcacta | gtgggatgct | gcccctcttt | gagcccaagg | gccgggtcct | cctggtggac | 300 |
| ggccaccacc | tggcctaccg | caccttccac | gccctgaagg | gcctcaccac | cagccggggg | 360 |
| gagccggtgc | aggcggtcta | cggcttcgcc | aagagcctcc | tcaaggccct | caaggaggac | 420 |
| ggggacgcgg | tgatcgtggt | ctttgacgcc | aaggccccct | ccttccgcca | cgaggcctac | 480 |
| gggggtaca | aggcgggccg | gccccccacg | ccggaggact | tccccggca | actcgccctc | 540 |
| atcaaggagc | tggtggacct | cctggggctg | gcgcgcctcg | aggtcccggg | ctacgaggcg | 600 |
| gacgacgtcc | tggccagcct | ggccaagaag | gcggaaaagg | agggctacga | ggtccgcatc | 660 |
| ctcaccgccg | acaaagacct | ttaccagctc | ctttccgacc | gcatccacgt | cctccacccc | 720 |
| gagggtacc | tcatcacccc | ggcctggctt | tgggaaaagt | acggcctgag | gcccgaccag | 780 |
| tgggccgact | accgggccct | gaccggggac | gagtccgaca | accttcccgg | ggtcaagggc | 840 |
| atcggggaga | gacggcgag | gaagcttctg | gaggagtggg | ggagcctgga | agccctcctc | 900 |
| aagaacctgg | accggctgaa | gcccgccatc | cgggagaaga | tcctggccca | catggacgat | 960 |
| ctgaagctct | cctgggacct | ggccaaggtg | cgcaccgacc | tgcccctgga | ggtggacttc | 1020 |
| gccaaaaggc | gggagcccga | ccgggagagg | cttagggcct | ttctggagag | gcttgagttt | 1080 |
| ggcagcctcc | tccacgagtt | cggccttctg | gaaagcccca | aggccctgga | ggaggccccc | 1140 |
| tggcccccgc | cggaagggc | cttcgtgggc | tttgtgcttt | cccgcaagga | gcccatgtgg | 1200 |
| gccgatcttc | tggccctggc | cgccgccagg | ggggccgggg | tccaccgggc | ccccgagcct | 1260 |
| tataaagccc | tcagggacct | gaaggaggcg | cgggggcttc | tcgccaaaga | cctgagcgtt | 1320 |
| ctggccctga | gggaaggcct | tggcctcccg | cccggcgacg | accccatgct | cctcgcctac | 1380 |
| ctcctggacc | cttccaacac | cacccccgag | gggtggccc | ggcgctacgg | cggggagtgg | 1440 |
| acggaggagg | cggggagcg | ggccgccctt | tccgagaggc | tcttcgccaa | cctgtggggg | 1500 |
| aggcttgagg | ggggaggagag | gctcctttgg | ctttaccggg | aggtggagag | gcccctttcc | 1560 |
| gctgtcctgg | cccacatgga | ggccacgggg | gtgcgcctgg | acgtggccta | tctcagggcc | 1620 |
| ttgtccctgg | aggtggccga | ggagatcgcc | cgcctcgagg | ccgaggtctt | ccgcctggcc | 1680 |
| ggccacccct | tcaacctcaa | ctccgggac | cagctggaaa | gggtcctctt | tgacgagcta | 1740 |
| gggcttcccg | ccatcggcaa | gacggagaag | accggcaagc | gctccaccag | cgccgccgtc | 1800 |
| ctggaggccc | tccgcgaggc | ccaccccatc | gtgagaaga | tcctgcagta | ccgggagctc | 1860 |
| accaagctga | agagcaccta | cattgacccc | ttgccggacc | tcatccaccc | caggacgggc | 1920 |
| cgcctccaca | cccgcttcaa | ccagacggcc | acggccacgg | gcaggctaag | tagctccgat | 1980 |
| cccaacctcc | agaacatccc | cgtccgcacc | ccgcttgggc | agaggatccg | ccgggccttc | 2040 |

```
atcgccgagg aggggtggct attggtggcc ctggactata gccagataga gctcagggtg   2100
ctggcccacc tctccggcga cgagaacctg atccgggtct tccaggaggg gcgggacatc   2160
cacacggaga ccgccagctg gatgttcggc gtccccgggg aggccgtgga ccccctgatg   2220
cgccgggcgg ccaagaccat caacttcggg gtcctctacg gcatgtcggc caccgcctc    2280 tcccaggagc tagccatccc ttacgaggag gcccaggcct tcattgagcg ctactttcag   2340
agcttcccca aggtgcgggc ctggattgag aagaccctgg aggagggcag gaggcggggg   2400
tacgtggaga ccctcttcgg ccgccgccgc tacgtgccag acctagaggc ccgggtgaag   2460
agcgtgcggg aggcggccga gcgcatggcc ttcaacatgc ccgtccaggg caccgccgcc   2520
gacctcatga agctgactat ggtgaagctc ttccccaggc tggaggaaat ggggggccagg  2580 atgctccttc aggtccacga cgagctggtc ctcgaggccc caaaagagag ggcggaggcc   2640
gtggcccggc tggccaagga ggtcatggag ggggtgtatc ccctggccgt gcccctggag   2700
gtggaggtgg ggatagggga ggactggctc tccgccaagg agtga                   2745
```

<210> SEQ ID NO 34
<211> LENGTH: 914
<212> TYPE: PRT
<213> ORGANISM: Artificial Sequence
<220> FEATURE:
<223> OTHER INFORMATION: Description of Artificial Sequence: Synthetic
      fusion protein <400> SEQUENCE: 34

```
Met Gly His His His His His His His His Ser Ser Gly His
  1               5                  10                  15

Ile Glu Gly Arg His Met Ser Lys Lys Gln Lys Leu Lys Phe Tyr Asp
             20                  25                  30

Ile Lys Ala Lys Gln Ala Phe Glu Thr Asp Gln Tyr Glu Val Ile Glu
         35                  40                  45

Lys Gln Thr Ala Arg Gly Pro Met Met Phe Ala Val Ala Lys Ser Pro
     50                  55                  60

Tyr Thr Gly Ile Lys Val Tyr Arg Leu Leu Gly Lys Lys Gly Gly
 65                  70                  75                  80

Gly Val Thr Ser Gly Met Leu Pro Leu Phe Glu Pro Lys Gly Arg Val
                 85                  90                  95

Leu Leu Val Asp Gly His His Leu Ala Tyr Arg Thr Phe His Ala Leu
            100                 105                 110

Lys Gly Leu Thr Thr Ser Arg Gly Glu Pro Val Gln Ala Val Tyr Gly
        115                 120                 125

Phe Ala Lys Ser Leu Leu Lys Ala Leu Lys Glu Asp Gly Asp Ala Val
    130                 135                 140

Ile Val Val Phe Asp Ala Lys Ala Pro Ser Phe Arg His Glu Ala Tyr
145                 150                 155                 160

Gly Gly Tyr Lys Ala Gly Arg Ala Pro Thr Pro Glu Asp Phe Pro Arg
                165                 170                 175

Gln Leu Ala Leu Ile Lys Glu Leu Val Asp Leu Leu Gly Leu Ala Arg
            180                 185                 190

Leu Glu Val Pro Gly Tyr Glu Ala Asp Asp Val Leu Ala Ser Leu Ala
        195                 200                 205

Lys Lys Ala Glu Lys Glu Gly Tyr Glu Val Arg Ile Leu Thr Ala Asp
    210                 215                 220

Lys Asp Leu Tyr Gln Leu Leu Ser Asp Arg Ile His Val Leu His Pro
225                 230                 235                 240
```

```
Glu Gly Tyr Leu Ile Thr Pro Ala Trp Leu Trp Lys Tyr Gly Leu
                245                 250                 255

Arg Pro Asp Gln Trp Ala Asp Tyr Arg Ala Leu Thr Gly Asp Glu Ser
            260                 265                 270

Asp Asn Leu Pro Gly Val Lys Gly Ile Gly Glu Lys Thr Ala Arg Lys
        275                 280                 285

Leu Leu Glu Glu Trp Gly Ser Leu Glu Ala Leu Leu Lys Asn Leu Asp
    290                 295                 300

Arg Leu Lys Pro Ala Ile Arg Glu Lys Ile Leu Ala His Met Asp Asp
305                 310                 315                 320

Leu Lys Leu Ser Trp Asp Leu Ala Lys Val Arg Thr Asp Leu Pro Leu
                325                 330                 335

Glu Val Asp Phe Ala Lys Arg Arg Glu Pro Asp Arg Glu Arg Leu Arg
            340                 345                 350

Ala Phe Leu Glu Arg Leu Glu Phe Gly Ser Leu Leu His Glu Phe Gly
        355                 360                 365

Leu Leu Glu Ser Pro Lys Ala Leu Glu Glu Ala Pro Trp Pro Pro Pro
    370                 375                 380

Glu Gly Ala Phe Val Gly Phe Val Leu Ser Arg Lys Glu Pro Met Trp
385                 390                 395                 400

Ala Asp Leu Leu Ala Leu Ala Ala Ala Arg Gly Gly Arg Val His Arg
                405                 410                 415

Ala Pro Glu Pro Tyr Lys Ala Leu Arg Asp Leu Lys Glu Ala Arg Gly
            420                 425                 430

Leu Leu Ala Lys Asp Leu Ser Val Leu Ala Leu Arg Glu Gly Leu Gly
        435                 440                 445

Leu Pro Pro Gly Asp Asp Pro Met Leu Leu Ala Tyr Leu Leu Asp Pro
    450                 455                 460

Ser Asn Thr Thr Pro Glu Gly Val Ala Arg Arg Tyr Gly Gly Glu Trp
465                 470                 475                 480

Thr Glu Glu Ala Gly Glu Arg Ala Ala Leu Ser Glu Arg Leu Phe Ala
                485                 490                 495

Asn Leu Trp Gly Arg Leu Glu Gly Glu Glu Arg Leu Leu Trp Leu Tyr
            500                 505                 510

Arg Glu Val Glu Arg Pro Leu Ser Ala Val Leu Ala His Met Glu Ala
        515                 520                 525

Thr Gly Val Arg Leu Asp Val Ala Tyr Leu Arg Ala Leu Ser Leu Glu
    530                 535                 540

Val Ala Glu Glu Ile Ala Arg Leu Glu Ala Glu Val Phe Arg Leu Ala
545                 550                 555                 560

Gly His Pro Phe Asn Leu Asn Ser Arg Asp Gln Leu Glu Arg Val Leu
                565                 570                 575

Phe Asp Glu Leu Gly Leu Pro Ala Ile Gly Lys Thr Glu Lys Thr Gly
            580                 585                 590

Lys Arg Ser Thr Ser Ala Ala Val Leu Glu Ala Leu Arg Glu Ala His
        595                 600                 605

Pro Ile Val Glu Lys Ile Leu Gln Tyr Arg Glu Leu Thr Lys Leu Lys
    610                 615                 620

Ser Thr Tyr Ile Asp Pro Leu Pro Asp Leu Ile His Pro Arg Thr Gly
625                 630                 635                 640

Arg Leu His Thr Arg Phe Asn Gln Thr Ala Thr Ala Thr Gly Arg Leu
                645                 650                 655
```

```
Ser Ser Ser Asp Pro Asn Leu Gln Asn Ile Pro Val Arg Thr Pro Leu
            660                 665                 670

Gly Gln Arg Ile Arg Arg Ala Phe Ile Ala Glu Glu Gly Trp Leu Leu
            675                 680                 685

Val Ala Leu Asp Tyr Ser Gln Ile Glu Leu Arg Val Leu Ala His Leu
            690                 695                 700

Ser Gly Asp Glu Asn Leu Ile Arg Val Phe Gln Glu Gly Arg Asp Ile
705                 710                 715                 720

His Thr Glu Thr Ala Ser Trp Met Phe Gly Val Pro Arg Glu Ala Val
            725                 730                 735

Asp Pro Leu Met Arg Arg Ala Ala Lys Thr Ile Asn Phe Gly Val Leu
            740                 745                 750

Tyr Gly Met Ser Ala His Arg Leu Ser Gln Glu Leu Ala Ile Pro Tyr
            755                 760                 765

Glu Glu Ala Gln Ala Phe Ile Glu Arg Tyr Phe Gln Ser Phe Pro Lys
            770                 775                 780

Val Arg Ala Trp Ile Glu Lys Thr Leu Glu Glu Gly Arg Arg Arg Gly
785                 790                 795                 800

Tyr Val Glu Thr Leu Phe Gly Arg Arg Arg Tyr Val Pro Asp Leu Glu
            805                 810                 815

Ala Arg Val Lys Ser Val Arg Glu Ala Ala Glu Arg Met Ala Phe Asn
            820                 825                 830

Met Pro Val Gln Gly Thr Ala Ala Asp Leu Met Lys Leu Ala Met Val
            835                 840                 845

Lys Leu Phe Pro Arg Leu Glu Glu Met Gly Ala Arg Met Leu Leu Gln
850                 855                 860

Val His Asp Glu Leu Val Leu Glu Ala Pro Lys Glu Arg Ala Glu Ala
865                 870                 875                 880

Val Ala Arg Leu Ala Lys Glu Val Met Glu Gly Val Tyr Pro Leu Ala
            885                 890                 895

Val Pro Leu Glu Val Glu Val Gly Ile Gly Glu Asp Trp Leu Ser Ala
            900                 905                 910

Lys Glu

<210> SEQ ID NO 35
<211> LENGTH: 894
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 35

His Met Ser Lys Lys Gln Lys Leu Lys Phe Tyr Asp Ile Lys Ala Lys
1               5                   10                  15

Gln Ala Phe Glu Thr Asp Gln Tyr Glu Val Ile Glu Lys Gln Thr Ala
            20                  25                  30

Arg Gly Pro Met Met Phe Ala Val Ala Lys Ser Pro Tyr Thr Gly Ile
            35                  40                  45

Lys Val Tyr Arg Leu Leu Gly Lys Lys Gly Gly Gly Val Thr Ser
            50                  55                  60

Gly Met Leu Pro Leu Phe Glu Pro Lys Gly Arg Val Leu Leu Val Asp
65                  70                  75                  80

Gly His His Leu Ala Tyr Arg Thr Phe His Ala Leu Lys Gly Leu Thr
                85                  90                  95
```

Thr Ser Arg Gly Glu Pro Val Gln Ala Val Tyr Gly Phe Ala Lys Ser
            100                 105                 110

Leu Leu Lys Ala Leu Lys Glu Asp Gly Asp Ala Val Ile Val Val Phe
        115                 120                 125

Asp Ala Lys Ala Pro Ser Phe Arg His Glu Ala Tyr Gly Gly Tyr Lys
    130                 135                 140

Ala Gly Arg Ala Pro Thr Pro Glu Asp Phe Pro Arg Gln Leu Ala Leu
145                 150                 155                 160

Ile Lys Glu Leu Val Asp Leu Leu Gly Leu Ala Arg Leu Glu Val Pro
                165                 170                 175

Gly Tyr Glu Ala Asp Asp Val Leu Ala Ser Leu Ala Lys Lys Ala Glu
            180                 185                 190

Lys Glu Gly Tyr Glu Val Arg Ile Leu Thr Ala Asp Lys Asp Leu Tyr
        195                 200                 205

Gln Leu Leu Ser Asp Arg Ile His Val Leu His Pro Glu Gly Tyr Leu
    210                 215                 220

Ile Thr Pro Ala Trp Leu Trp Glu Lys Tyr Gly Leu Arg Pro Asp Gln
225                 230                 235                 240

Trp Ala Asp Tyr Arg Ala Leu Thr Gly Asp Glu Ser Asp Asn Leu Pro
                245                 250                 255

Gly Val Lys Gly Ile Gly Glu Lys Thr Ala Arg Lys Leu Leu Glu Glu
            260                 265                 270

Trp Gly Ser Leu Glu Ala Leu Leu Lys Asn Leu Asp Arg Leu Lys Pro
        275                 280                 285

Ala Ile Arg Glu Lys Ile Leu Ala His Met Asp Asp Leu Lys Leu Ser
    290                 295                 300

Trp Asp Leu Ala Lys Val Arg Thr Asp Leu Pro Leu Glu Val Asp Phe
305                 310                 315                 320

Ala Lys Arg Arg Glu Pro Asp Arg Glu Arg Leu Arg Ala Phe Leu Glu
                325                 330                 335

Arg Leu Glu Phe Gly Ser Leu Leu His Glu Phe Gly Leu Leu Glu Ser
            340                 345                 350

Pro Lys Ala Leu Glu Glu Ala Pro Trp Pro Pro Pro Glu Gly Ala Phe
        355                 360                 365

Val Gly Phe Val Leu Ser Arg Lys Glu Pro Met Trp Ala Asp Leu Leu
    370                 375                 380

Ala Leu Ala Ala Ala Arg Gly Gly Arg Val His Arg Ala Pro Glu Pro
385                 390                 395                 400

Tyr Lys Ala Leu Arg Asp Leu Lys Glu Ala Arg Gly Leu Leu Ala Lys
                405                 410                 415

Asp Leu Ser Val Leu Ala Leu Arg Glu Gly Leu Gly Leu Pro Pro Gly
            420                 425                 430

Asp Asp Pro Met Leu Leu Ala Tyr Leu Leu Asp Pro Ser Asn Thr Thr
        435                 440                 445

Pro Glu Gly Val Ala Arg Arg Tyr Gly Gly Glu Trp Thr Glu Glu Ala
    450                 455                 460

Gly Glu Arg Ala Ala Leu Ser Glu Arg Leu Phe Ala Asn Leu Trp Gly
465                 470                 475                 480

Arg Leu Glu Gly Glu Glu Arg Leu Leu Trp Leu Tyr Arg Glu Val Glu
                485                 490                 495

Arg Pro Leu Ser Ala Val Leu Ala His Met Glu Ala Thr Gly Val Arg
            500                 505                 510

Leu Asp Val Ala Tyr Leu Arg Ala Leu Ser Leu Glu Val Ala Glu Glu 515                 520                 525
Ile Ala Arg Leu Glu Ala Glu Val Phe Arg Leu Ala Gly His Pro Phe
530                 535                 540

Asn Leu Asn Ser Arg Asp Gln Leu Glu Arg Val Leu Phe Asp Glu Leu
545                 550                 555                 560

Gly Leu Pro Ala Ile Gly Lys Thr Glu Lys Thr Gly Lys Arg Ser Thr
                565                 570                 575

Ser Ala Ala Val Leu Glu Ala Leu Arg Glu Ala His Pro Ile Val Glu
                580                 585                 590

Lys Ile Leu Gln Tyr Arg Glu Leu Thr Lys Leu Lys Ser Thr Tyr Ile
                595                 600                 605

Asp Pro Leu Pro Asp Leu Ile His Pro Arg Thr Gly Arg Leu His Thr
610                 615                 620

Arg Phe Asn Gln Thr Ala Thr Ala Thr Gly Arg Leu Ser Ser Ser Asp
625                 630                 635                 640

Pro Asn Leu Gln Asn Ile Pro Val Arg Thr Pro Leu Gly Gln Arg Ile
                645                 650                 655

Arg Arg Ala Phe Ile Ala Glu Glu Gly Trp Leu Leu Val Ala Leu Asp
                660                 665                 670

Tyr Ser Gln Ile Glu Leu Arg Val Leu Ala His Leu Ser Gly Asp Glu
                675                 680                 685

Asn Leu Ile Arg Val Phe Gln Glu Gly Arg Asp Ile His Thr Glu Thr
690                 695                 700

Ala Ser Trp Met Phe Gly Val Pro Arg Glu Ala Val Asp Pro Leu Met
705                 710                 715                 720

Arg Arg Ala Ala Lys Thr Ile Asn Phe Gly Val Leu Tyr Gly Met Ser
                725                 730                 735

Ala His Arg Leu Ser Gln Glu Leu Ala Ile Pro Tyr Glu Glu Ala Gln
                740                 745                 750

Ala Phe Ile Glu Arg Tyr Phe Gln Ser Phe Pro Lys Val Arg Ala Trp
                755                 760                 765

Ile Glu Lys Thr Leu Glu Glu Gly Arg Arg Gly Tyr Val Glu Thr
770                 775                 780

Leu Phe Gly Arg Arg Arg Tyr Val Pro Asp Leu Glu Ala Arg Val Lys
785                 790                 795                 800

Ser Val Arg Glu Ala Ala Glu Arg Met Ala Phe Asn Met Pro Val Gln
                805                 810                 815

Gly Thr Ala Ala Asp Leu Met Lys Leu Ala Met Val Lys Leu Phe Pro
                820                 825                 830

Arg Leu Glu Glu Met Gly Ala Arg Met Leu Leu Gln Val His Asp Glu
                835                 840                 845

Leu Val Leu Glu Ala Pro Lys Glu Arg Ala Glu Ala Val Ala Arg Leu
850                 855                 860

Ala Lys Glu Val Met Glu Gly Val Tyr Pro Leu Ala Val Pro Leu Glu
865                 870                 875                 880

Val Glu Val Gly Ile Gly Glu Asp Trp Leu Ser Ala Lys Glu
                885                 890

<210> SEQ ID NO 36
<211> LENGTH: 2742
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

```
atgggccatc atcatcatca tcatcatcat catcacagca gcggccatat cgaaggtcgt    60
catatgccga agaaggagaa gattaagttc ttcgacctgg tcgccaagaa gtactacgag   120
actgacaact acgaagtcga gattaaggag actaagcgcg gcaagtttcg cttcgccaaa   180
gccaagagcc cgtacaccgg caagatcttc tatcgcgtgc tgggcaaagc cggcggcggt   240
gtcactagtg ggatgctgcc cctctttgag cccaagggcc gggtcctcct ggtggacggc   300
caccacctgg cctaccgcac cttccacgcc ctgaagggcc tcaccaccag ccggggggag   360
ccggtgcagg cggtctacgg cttcgccaag agcctcctca aggccctcaa ggaggacggg   420
gacgcggtga tcgtggtctt tgacgccaag gcccctcct tccgccacga ggcctacggg   480
gggtacaagg cgggccgggc ccccacgccg gaggactttc cccggcaact cgccctcatc   540
aaggagctgg tggacctcct ggggctggcg cgcctcgagg tcccgggcta cgaggcggac   600
gacgtcctgg ccagcctggc caagaaggcg gaaaaggagg gctacgaggt ccgcatcctc   660
accgccgaca agaccttta ccagctcctt tccgaccgca tccacgtcct ccaccccgag   720
gggtacctca tcaccccggc ctggctttgg gaaaagtacg gcctgaggcc cgaccagtgg   780
gccgactacc gggccctgac cggggacgag tccgacaacc ttcccggggt caagggcatc   840
ggggagaaga cggcgaggaa gcttctggag gagtggggga gcctggaagc cctcctcaag   900
aacctggacc ggctgaagcc cgccatccgg gagaagatcc tggcccacat ggacgatctg   960
aagctctcct gggaccctgg caaggtgcgc accgacctgc ccctggaggt ggacttcgcc  1020
aaaaggcggg agcccgaccg ggagaggctt agggcctttc tggagaggct tgagtttggc  1080
agcctcctcc acgagttcgg ccttctggaa agccccaagg ccctggagga ggcccctgg  1140
cccccgccgg aaggggcctt cgtgggcttt gtgctttccc gcaaggagcc catgtgggcc  1200
gatcttctgg ccctggccgc cgccaggggg ggccgggtcc accggccccc cgagccttat  1260
aaagccctca gggacctgaa ggaggcgcgg gggcttctcg ccaaagacct gagcgttctg  1320
gccctgaggg aaggccttgg cctcccgccc ggcgacgacc ccatgctcct cgcctacctc  1380
ctggacccctt ccaacaccac ccccgagggg gtggcccggc gctacggcgg ggagtggacg  1440
gaggaggcgg gggagcgggc cgcccttttcc gagaggctct cgccaacct gtggggagg  1500
cttgaggggg aggagaggct cctttggctt taccgggagg tggagaggcc cctttccgct  1560
gtcctggccc acatggaggc cacggggtg cgcctggacg tggcctatct cagggccttg  1620
tccctggagg tggccgagga gatcgcccgc ctcgaggccg aggtcttccg cctgccggc  1680
caccccttca acctcaactc ccgggaccag ctggaaaggg tcctctttga cgagctaggg  1740
cttcccgcca tcggcaagac ggagaagacc ggcaagcgct ccaccagcgc cgccgtcctg  1800
gaggccctcc gcgaggccca ccccatcgtg gagaagatcc tgcagtaccg ggagctcacc  1860
aagctgaaga gcacctacat tgaccccttg ccggacctca tccaccccag gacgggccgc  1920
ctccacaccc gcttcaacca gacggccacg gccacgggca ggctaagtag ctccgatccc  1980
aacctccaga acatccccgt ccgcacccgc cttgggcaga ggatccgccg ggccttcatc  2040
gccgaggagg ggtggctatt ggtggccctg gactatagcc agatagagct cagggtgctg  2100
gcccacctct ccggcgacga gaacctgatc cgggtcttcc aggaggggcg ggacatccac  2160
acggagaccg ccagctggat gttcggcgtc cccgggagg ccgtgaccc cctgatgcgc  2220
cgggcggcca agaccatcaa cttcggggtc ctctacggca tgtcggccca ccgcctctcc  2280
```

-continued

```
caggagctag ccatccctta cgaggaggcc caggccttca ttgagcgcta ctttcagagc    2340
ttccccaagg tgcgggcctg gattgagaag accctggagg agggcaggag gcgggggtac    2400
gtggagaccc tcttcggccg ccgccgctac gtgccagacc tagaggcccg ggtgaagagc    2460
gtgcgggagg cggccgagcg catggccttc aacatgcccg tccagggcac cgccgccgac    2520
ctcatgaagc tggctatggt gaagctcttc cccaggctgg aggaaatggg ggccaggatg    2580
ctccttcagg tccacgacga gctggtcctc gaggccccaa agagagggc ggaggccgtg    2640 gcccggctgg ccaaggaggt catggagggg gtgtatcccc tggccgtgcc cctggaggtg    2700
gaggtgggga taggggagga ctggctctcc gccaaggagt ga                      2742
```

<210> SEQ ID NO 37
<211> LENGTH: 913
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 37

```
Met Gly His His His His His His His His His Ser Ser Gly His
1               5                   10                  15

Ile Glu Gly Arg His Met Pro Lys Lys Glu Lys Ile Lys Phe Phe Asp
            20                  25                  30

Leu Val Ala Lys Lys Tyr Tyr Glu Thr Asp Asn Tyr Glu Val Glu Ile
        35                  40                  45

Lys Glu Thr Lys Arg Gly Lys Phe Arg Phe Ala Lys Ala Lys Ser Pro
    50                  55                  60

Tyr Thr Gly Lys Ile Phe Tyr Arg Val Leu Gly Lys Ala Gly Gly Gly
65                  70                  75                  80

Val Thr Ser Gly Met Leu Pro Leu Phe Glu Pro Lys Gly Arg Val Leu
                85                  90                  95

Leu Val Asp Gly His His Leu Ala Tyr Arg Thr Phe His Ala Leu Lys
            100                 105                 110

Gly Leu Thr Thr Ser Arg Gly Glu Pro Val Gln Ala Val Tyr Gly Phe
        115                 120                 125

Ala Lys Ser Leu Leu Lys Ala Leu Lys Glu Asp Gly Asp Ala Val Ile
    130                 135                 140

Val Val Phe Asp Ala Lys Ala Pro Ser Phe Arg His Glu Ala Tyr Gly
145                 150                 155                 160

Gly Tyr Lys Ala Gly Arg Ala Pro Thr Pro Glu Asp Phe Pro Arg Gln
                165                 170                 175

Leu Ala Leu Ile Lys Glu Leu Val Asp Leu Leu Gly Leu Ala Arg Leu
            180                 185                 190

Glu Val Pro Gly Tyr Glu Ala Asp Asp Val Leu Ala Ser Leu Ala Lys
        195                 200                 205

Lys Ala Glu Lys Glu Gly Tyr Glu Val Arg Ile Leu Thr Ala Asp Lys
    210                 215                 220

Asp Leu Tyr Gln Leu Leu Ser Asp Arg Ile His Val Leu His Pro Glu
225                 230                 235                 240

Gly Tyr Leu Ile Thr Pro Ala Trp Leu Trp Glu Lys Tyr Gly Leu Arg
                245                 250                 255

Pro Asp Gln Trp Ala Asp Tyr Arg Ala Leu Thr Gly Asp Glu Ser Asp
            260                 265                 270

Asn Leu Pro Gly Val Lys Gly Ile Gly Glu Lys Thr Ala Arg Lys Leu
```

-continued

```
            275                 280                 285
Leu Glu Glu Trp Gly Ser Leu Glu Ala Leu Leu Lys Asn Leu Asp Arg
        290                 295                 300
Leu Lys Pro Ala Ile Arg Glu Lys Ile Leu Ala His Met Asp Asp Leu
305                 310                 315                 320
Lys Leu Ser Trp Asp Leu Ala Lys Val Arg Thr Asp Leu Pro Leu Glu
                325                 330                 335
Val Asp Phe Ala Lys Arg Arg Glu Pro Asp Arg Glu Arg Leu Arg Ala
                340                 345                 350
Phe Leu Glu Arg Leu Glu Phe Gly Ser Leu Leu His Glu Phe Gly Leu
        355                 360                 365
Leu Glu Ser Pro Lys Ala Leu Glu Glu Ala Pro Trp Pro Pro Pro Glu
        370                 375                 380
Gly Ala Phe Val Gly Phe Val Leu Ser Arg Lys Glu Pro Met Trp Ala
385                 390                 395                 400
Asp Leu Leu Ala Leu Ala Ala Arg Gly Gly Arg Val His Arg Ala
                405                 410                 415
Pro Glu Pro Tyr Lys Ala Leu Arg Asp Leu Lys Glu Ala Arg Gly Leu
                420                 425                 430
Leu Ala Lys Asp Leu Ser Val Leu Ala Leu Arg Glu Gly Leu Gly Leu
        435                 440                 445
Pro Pro Gly Asp Asp Pro Met Leu Leu Ala Tyr Leu Leu Asp Pro Ser
450                 455                 460
Asn Thr Thr Pro Glu Gly Val Ala Arg Arg Tyr Gly Gly Glu Trp Thr
465                 470                 475                 480
Glu Glu Ala Gly Glu Arg Ala Ala Leu Ser Glu Arg Leu Phe Ala Asn
                485                 490                 495
Leu Trp Gly Arg Leu Glu Gly Glu Glu Arg Leu Leu Trp Leu Tyr Arg
                500                 505                 510
Glu Val Glu Arg Pro Leu Ser Ala Val Leu Ala His Met Glu Ala Thr
        515                 520                 525
Gly Val Arg Leu Asp Val Ala Tyr Leu Arg Ala Leu Ser Leu Glu Val
        530                 535                 540
Ala Glu Glu Ile Ala Arg Leu Glu Ala Glu Val Phe Arg Leu Ala Gly
545                 550                 555                 560
His Pro Phe Asn Leu Asn Ser Arg Asp Gln Leu Glu Arg Val Leu Phe
                565                 570                 575
Asp Glu Leu Gly Leu Pro Ala Ile Gly Lys Thr Glu Lys Thr Gly Lys
                580                 585                 590
Arg Ser Thr Ser Ala Ala Val Leu Glu Ala Leu Arg Glu Ala His Pro
        595                 600                 605
Ile Val Glu Lys Ile Leu Gln Tyr Arg Glu Leu Thr Lys Leu Lys Ser
        610                 615                 620
Thr Tyr Ile Asp Pro Leu Pro Asp Leu Ile His Pro Arg Thr Gly Arg
625                 630                 635                 640
Leu His Thr Arg Phe Asn Gln Thr Ala Thr Ala Thr Gly Arg Leu Ser
                645                 650                 655
Ser Ser Asp Pro Asn Leu Gln Asn Ile Pro Val Arg Thr Pro Leu Gly
                660                 665                 670
Gln Arg Ile Arg Arg Ala Phe Ile Ala Glu Glu Gly Trp Leu Leu Val
        675                 680                 685
Ala Leu Asp Tyr Ser Gln Ile Glu Leu Arg Val Leu Ala His Leu Ser
        690                 695                 700
```

```
Gly Asp Glu Asn Leu Ile Arg Val Phe Gln Glu Gly Arg Asp Ile His
705                 710                 715                 720

Thr Glu Thr Ala Ser Trp Met Phe Gly Val Pro Arg Glu Ala Val Asp
            725                 730                 735

Pro Leu Met Arg Arg Ala Ala Lys Thr Ile Asn Phe Gly Val Leu Tyr
            740                 745                 750

Gly Met Ser Ala His Arg Leu Ser Gln Glu Leu Ala Ile Pro Tyr Glu
        755                 760                 765

Glu Ala Gln Ala Phe Ile Glu Arg Tyr Phe Gln Ser Phe Pro Lys Val
    770                 775                 780

Arg Ala Trp Ile Glu Lys Thr Leu Glu Glu Gly Arg Arg Arg Gly Tyr
785                 790                 795                 800

Val Glu Thr Leu Phe Gly Arg Arg Tyr Val Pro Asp Leu Glu Ala
            805                 810                 815

Arg Val Lys Ser Val Arg Glu Ala Ala Glu Arg Met Ala Phe Asn Met
            820                 825                 830

Pro Val Gln Gly Thr Ala Ala Asp Leu Met Lys Leu Ala Met Val Lys
            835                 840                 845

Leu Phe Pro Arg Leu Glu Glu Met Gly Ala Arg Met Leu Leu Gln Val
            850                 855                 860

His Asp Glu Leu Val Leu Glu Ala Pro Lys Glu Arg Ala Glu Ala Val
865                 870                 875                 880

Ala Arg Leu Ala Lys Glu Val Met Glu Gly Val Tyr Pro Leu Ala Val
            885                 890                 895

Pro Leu Glu Val Glu Val Gly Ile Gly Glu Asp Trp Leu Ser Ala Lys
            900                 905                 910

Glu

<210> SEQ ID NO 38
<211> LENGTH: 893
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 38

His Met Pro Lys Lys Glu Lys Ile Lys Phe Phe Asp Leu Val Ala Lys
1               5                   10                  15

Lys Tyr Tyr Glu Thr Asp Asn Tyr Glu Val Glu Ile Lys Glu Thr Lys
            20                  25                  30

Arg Gly Lys Phe Arg Phe Ala Lys Ala Lys Ser Pro Tyr Thr Gly Lys
        35                  40                  45

Ile Phe Tyr Arg Val Leu Gly Lys Ala Gly Gly Val Thr Ser Gly
    50                  55                  60

Met Leu Pro Leu Phe Glu Pro Lys Gly Arg Val Leu Val Asp Gly
65              70                  75              80

His His Leu Ala Tyr Arg Thr Phe His Ala Leu Lys Gly Leu Thr Thr
                85                  90                  95

Ser Arg Gly Glu Pro Val Gln Ala Val Tyr Gly Phe Ala Lys Ser Leu
            100                 105                 110

Leu Lys Ala Leu Lys Glu Asp Gly Asp Ala Val Ile Val Val Phe Asp
        115                 120                 125

Ala Lys Ala Pro Ser Phe Arg His Glu Ala Tyr Gly Gly Tyr Lys Ala
    130                 135                 140
```

```
Gly Arg Ala Pro Thr Pro Glu Asp Phe Pro Arg Gln Leu Ala Leu Ile
145                 150                 155                 160

Lys Glu Leu Val Asp Leu Leu Gly Leu Ala Arg Leu Glu Val Pro Gly
                165                 170                 175

Tyr Glu Ala Asp Asp Val Leu Ala Ser Leu Ala Lys Lys Ala Glu Lys
            180                 185                 190

Glu Gly Tyr Glu Val Arg Ile Leu Thr Ala Asp Lys Asp Leu Tyr Gln
        195                 200                 205

Leu Leu Ser Asp Arg Ile His Val Leu His Pro Glu Gly Tyr Leu Ile
210                 215                 220

Thr Pro Ala Trp Leu Trp Glu Lys Tyr Gly Leu Arg Pro Asp Gln Trp
225                 230                 235                 240

Ala Asp Tyr Arg Ala Leu Thr Gly Asp Glu Ser Asp Asn Leu Pro Gly
                245                 250                 255

Val Lys Gly Ile Gly Glu Lys Thr Ala Arg Lys Leu Leu Glu Glu Trp
            260                 265                 270

Gly Ser Leu Glu Ala Leu Leu Lys Asn Leu Asp Arg Leu Lys Pro Ala
        275                 280                 285

Ile Arg Glu Lys Ile Leu Ala His Met Asp Asp Leu Lys Leu Ser Trp
290                 295                 300

Asp Leu Ala Lys Val Arg Thr Asp Leu Pro Leu Glu Val Asp Phe Ala
305                 310                 315                 320

Lys Arg Arg Glu Pro Asp Arg Glu Arg Leu Arg Ala Phe Leu Glu Arg
                325                 330                 335

Leu Glu Phe Gly Ser Leu Leu His Glu Phe Gly Leu Leu Glu Ser Pro
            340                 345                 350

Lys Ala Leu Glu Glu Ala Pro Trp Pro Pro Glu Gly Ala Phe Val
        355                 360                 365

Gly Phe Val Leu Ser Arg Lys Glu Pro Met Trp Ala Asp Leu Leu Ala
370                 375                 380

Leu Ala Ala Ala Arg Gly Gly Arg Val His Arg Ala Pro Glu Pro Tyr
385                 390                 395                 400

Lys Ala Leu Arg Asp Leu Lys Glu Ala Arg Gly Leu Leu Ala Lys Asp
                405                 410                 415

Leu Ser Val Leu Ala Leu Arg Glu Gly Leu Gly Leu Pro Pro Gly Asp
            420                 425                 430

Asp Pro Met Leu Leu Ala Tyr Leu Leu Asp Pro Ser Asn Thr Thr Pro
        435                 440                 445

Glu Gly Val Ala Arg Arg Tyr Gly Gly Glu Trp Thr Glu Glu Ala Gly
450                 455                 460

Glu Arg Ala Ala Leu Ser Glu Arg Leu Phe Ala Asn Leu Trp Gly Arg
465                 470                 475                 480

Leu Glu Gly Glu Glu Arg Leu Leu Trp Leu Tyr Arg Glu Val Glu Arg
                485                 490                 495

Pro Leu Ser Ala Val Leu Ala His Met Glu Ala Thr Gly Val Arg Leu
            500                 505                 510

Asp Val Ala Tyr Leu Arg Ala Leu Ser Leu Glu Val Ala Glu Glu Ile
        515                 520                 525

Ala Arg Leu Glu Ala Glu Val Phe Arg Leu Ala Gly His Pro Phe Asn
530                 535                 540

Leu Asn Ser Arg Asp Gln Leu Glu Arg Val Leu Phe Asp Glu Leu Gly
545                 550                 555                 560
```

```
Leu Pro Ala Ile Gly Lys Thr Glu Lys Thr Gly Lys Arg Ser Thr Ser
                565                 570                 575
Ala Ala Val Leu Glu Ala Leu Arg Glu Ala His Pro Ile Val Glu Lys
            580                 585                 590
Ile Leu Gln Tyr Arg Glu Leu Thr Lys Leu Lys Ser Thr Tyr Ile Asp
        595                 600                 605
Pro Leu Pro Asp Leu Ile His Pro Arg Thr Gly Arg Leu His Thr Arg
    610                 615                 620
Phe Asn Gln Thr Ala Thr Ala Thr Gly Arg Leu Ser Ser Ser Asp Pro
625                 630                 635                 640
Asn Leu Gln Asn Ile Pro Val Arg Thr Pro Leu Gly Gln Arg Ile Arg
                645                 650                 655
Arg Ala Phe Ile Ala Glu Glu Gly Trp Leu Leu Val Ala Leu Asp Tyr
            660                 665                 670
Ser Gln Ile Glu Leu Arg Val Leu Ala His Leu Ser Gly Asp Glu Asn
        675                 680                 685
Leu Ile Arg Val Phe Gln Glu Gly Arg Asp Ile His Thr Glu Thr Ala
    690                 695                 700
Ser Trp Met Phe Gly Val Pro Arg Glu Ala Val Asp Pro Leu Met Arg
705                 710                 715                 720
Arg Ala Ala Lys Thr Ile Asn Phe Gly Val Leu Tyr Gly Met Ser Ala
                725                 730                 735
His Arg Leu Ser Gln Glu Leu Ala Ile Pro Tyr Glu Glu Ala Gln Ala
            740                 745                 750
Phe Ile Glu Arg Tyr Phe Gln Ser Phe Pro Lys Val Arg Ala Trp Ile
        755                 760                 765
Glu Lys Thr Leu Glu Glu Gly Arg Arg Arg Gly Tyr Val Glu Thr Leu
    770                 775                 780
Phe Gly Arg Arg Arg Tyr Val Pro Asp Leu Glu Ala Arg Val Lys Ser
785                 790                 795                 800
Val Arg Glu Ala Ala Glu Arg Met Ala Phe Asn Met Pro Val Gln Gly
                805                 810                 815
Thr Ala Ala Asp Leu Met Lys Leu Ala Met Val Lys Leu Phe Pro Arg
            820                 825                 830
Leu Glu Glu Met Gly Ala Arg Met Leu Leu Gln Val His Asp Glu Leu
        835                 840                 845
Val Leu Glu Ala Pro Lys Glu Arg Ala Glu Ala Val Ala Arg Leu Ala
    850                 855                 860
Lys Glu Val Met Glu Gly Val Tyr Pro Leu Ala Val Pro Leu Glu Val
865                 870                 875                 880
Glu Val Gly Ile Gly Glu Asp Trp Leu Ser Ala Lys Glu
                885                 890

<210> SEQ ID NO 39
<211> LENGTH: 1881
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atgggccatc atcatcatca tcatcatcat catcacagca gcggccatat cgaaggtcgt      60
catatgtcca agaagcagaa actgaagttc tacgacatta aggcgaagca ggcgtttgag     120
accgaccagt acgaggttat tgagaagcag accgcccgcg gtccgatgat gttcgccgtg     180
```

```
gccaaatcgc cgtacaccgg cattaaagtg taccgcctgt taggcaagaa gaaaggcggc    240
ggtgtcacta gtcccaaggc cctggaggag cccccctggc cccgccggaa aggggccttc    300
gtgggctttg tgctttcccg caaggagccc atgtgggccg atcttctggc cctggccgcc    360 gccaggggg gccgggtcca ccgggccccc gagccttata aagccctcag ggacctgaag    420
gaggcgcggg ggcttctcgc caaagacctg agcgttctgg ccctgaggga aggccttggc    480
ctcccgcccg cgacgaccc catgctcctc gcctacctcc tggacccttc caacaccacc    540 cccgagggg tggcccggcg ctacggcggg gagtggacgg aggaggcggg ggagcgggcc    600 gcccttccg agaggctctt cgccaacctg tggggaggc ttgaggggga ggagaggctc    660
ctttggcttt accgggaggt ggagaggccc ctttccgctg tcctggccca catggaggcc    720 acggggtgc gcctgacgt ggcctatctc agggccttgt ccctggaggt ggccgaggag    780
atcgcccgcc tcgaggccga ggtcttccgc ctggccggcc accccttcaa cctcaactcc    840
cgggaccagc tggaaagggt cctctttgac gagctagggc ttcccgccat cggcaagacg    900
gagaagaccg gcaagcgctc caccagcgcc gccgtcctgg aggccctccg cgaggcccac    960
cccatcgtgg agaagatcct gcagtaccgg gagctcacca agctgaagag cacctacatt    1020
gaccccttgc cggacctcat cccccccagg acgggccgcc tccacacccg cttcaaccag    1080
acggccacgg ccacgggcag gctaagtagc tccgatccca acctccagaa catcccgtc    1140 cgcacccgc ttgggcagag gatccgccgg gccttcatcg ccgaggaggg gtggctattg    1200
gtggccctgg actatagcca gatagagctc agggtgctgg cccacctctc cggcgacgag    1260
aacctgatcc gggtcttcca ggaggggcgg gacatccaca cggagaccgc cagctggatg    1320
ttcggcgtcc cccgggaggc cgtggacccc ctgatgcgcc gggcggccaa gaccatcaac    1380 ttcgggtcc tctacggcat gtcggcccac cgcctctccc aggagctagc catcccttac    1440
gaggaggccc aggccttcat tgagcgctac tttcagagct tccccaaggt gcgggcctgg    1500
attgagaaga ccctggagga gggcaggagg cgggggtacg tggagaccct cttcggccgc    1560
cgccgctacg tgccagacct agaggcccgg gtgaagagcg tgcggaggc ggccgagcgc    1620 atggccttca acatgcccgt ccagggcacc gccgccgacc tcatgaagct ggctatggtg    1680
aagctcttcc ccaggctgga ggaaatgggg gccaggatgc tccttcaggt ccacgacgag    1740
ctggtcctcg aggccccaaa agagagggcg gaggccgtgg cccggctggc caaggaggtc    1800 atggagggg tgtatcccct ggccgtgccc ctggaggtgg aggtggggat aggggaggac    1860
tggctctccg ccaaggagtg a                                               1881
```

<210> SEQ ID NO 40
<211> LENGTH: 626
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 40

Met Gly His His His His His His His His His Ser Ser Gly His
1               5                   10                  15

Ile Glu Gly Arg His Met Ser Lys Lys Gln Lys Leu Lys Phe Tyr Asp
            20                  25                  30

Ile Lys Ala Lys Gln Ala Phe Glu Thr Asp Gln Tyr Glu Val Ile Glu
        35                  40                  45

```
Lys Gln Thr Ala Arg Gly Pro Met Met Phe Ala Val Ala Lys Ser Pro
     50                  55                  60

Tyr Thr Gly Ile Lys Val Tyr Arg Leu Leu Gly Lys Lys Lys Gly Gly
 65                  70                  75                  80

Gly Val Thr Ser Pro Lys Ala Leu Glu Glu Ala Pro Trp Pro Pro Pro
                 85                  90                  95

Glu Gly Ala Phe Val Gly Phe Val Leu Ser Arg Lys Glu Pro Met Trp
                100                 105                 110

Ala Asp Leu Leu Ala Leu Ala Ala Arg Gly Gly Arg Val His Arg
            115                 120                 125

Ala Pro Glu Pro Tyr Lys Ala Leu Arg Asp Leu Lys Glu Ala Arg Gly
    130                 135                 140

Leu Leu Ala Lys Asp Leu Ser Val Leu Ala Leu Arg Glu Gly Leu Gly
145                 150                 155                 160

Leu Pro Pro Gly Asp Asp Pro Met Leu Leu Ala Tyr Leu Leu Asp Pro
                165                 170                 175

Ser Asn Thr Thr Pro Glu Gly Val Ala Arg Arg Tyr Gly Gly Glu Trp
            180                 185                 190

Thr Glu Glu Ala Gly Glu Arg Ala Ala Leu Ser Glu Arg Leu Phe Ala
    195                 200                 205

Asn Leu Trp Gly Arg Leu Glu Gly Glu Glu Arg Leu Leu Trp Leu Tyr
    210                 215                 220

Arg Glu Val Glu Arg Pro Leu Ser Ala Val Leu Ala His Met Glu Ala
225                 230                 235                 240

Thr Gly Val Arg Leu Asp Val Ala Tyr Leu Arg Ala Leu Ser Leu Glu
                245                 250                 255

Val Ala Glu Glu Ile Ala Arg Leu Glu Ala Glu Val Phe Arg Leu Ala
            260                 265                 270

Gly His Pro Phe Asn Leu Asn Ser Arg Asp Gln Leu Glu Arg Val Leu
    275                 280                 285

Phe Asp Glu Leu Gly Leu Pro Ala Ile Gly Lys Thr Glu Lys Thr Gly
    290                 295                 300

Lys Arg Ser Thr Ser Ala Ala Val Leu Glu Ala Leu Arg Glu Ala His
305                 310                 315                 320

Pro Ile Val Glu Lys Ile Leu Gln Tyr Arg Glu Leu Thr Lys Leu Lys
                325                 330                 335

Ser Thr Tyr Ile Asp Pro Leu Pro Asp Leu Ile His Pro Arg Thr Gly
            340                 345                 350

Arg Leu His Thr Arg Phe Asn Gln Thr Ala Thr Ala Thr Gly Arg Leu
    355                 360                 365

Ser Ser Ser Asp Pro Asn Leu Gln Asn Ile Pro Val Arg Thr Pro Leu
370                 375                 380

Gly Gln Arg Ile Arg Arg Ala Phe Ile Ala Glu Gly Trp Leu Leu
385                 390                 395                 400

Val Ala Leu Asp Tyr Ser Gln Ile Glu Leu Arg Val Leu Ala His Leu
                405                 410                 415

Ser Gly Asp Glu Asn Leu Ile Arg Val Phe Gln Glu Gly Arg Asp Ile
            420                 425                 430

His Thr Glu Thr Ala Ser Trp Met Phe Gly Val Pro Arg Glu Ala Val
    435                 440                 445

Asp Pro Leu Met Arg Arg Ala Ala Lys Thr Ile Asn Phe Gly Val Leu
    450                 455                 460

Tyr Gly Met Ser Ala His Arg Leu Ser Gln Glu Leu Ala Ile Pro Tyr
```

```
                465                 470                 475                 480
Glu Glu Ala Gln Ala Phe Ile Glu Arg Tyr Phe Gln Ser Phe Pro Lys
                    485                 490                 495
Val Arg Ala Trp Ile Glu Lys Thr Leu Glu Glu Gly Arg Arg Arg Gly
                500                 505                 510
Tyr Val Glu Thr Leu Phe Gly Arg Arg Tyr Val Pro Asp Leu Glu
                515                 520                 525
Ala Arg Val Lys Ser Val Arg Glu Ala Ala Glu Arg Met Ala Phe Asn
            530                 535                 540
Met Pro Val Gln Gly Thr Ala Ala Asp Leu Met Lys Leu Ala Met Val
545                 550                 555                 560
Lys Leu Phe Pro Arg Leu Glu Met Gly Ala Arg Met Leu Leu Gln
                    565                 570                 575
Val His Asp Glu Leu Val Leu Glu Ala Pro Lys Glu Arg Ala Glu Ala
            580                 585                 590
Val Ala Arg Leu Ala Lys Glu Val Met Glu Gly Val Tyr Pro Leu Ala
            595                 600                 605
Val Pro Leu Glu Val Glu Val Gly Ile Gly Glu Asp Trp Leu Ser Ala
        610                 615                 620
Lys Glu
625

<210> SEQ ID NO 41
<211> LENGTH: 606
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 41

His Met Ser Lys Lys Gln Lys Leu Lys Phe Tyr Asp Ile Lys Ala Lys
  1               5                  10                  15
Gln Ala Phe Glu Thr Asp Gln Tyr Glu Val Ile Glu Lys Gln Thr Ala
                 20                  25                  30
Arg Gly Pro Met Met Phe Ala Val Ala Lys Ser Pro Tyr Thr Gly Ile
             35                  40                  45
Lys Val Tyr Arg Leu Leu Gly Lys Lys Gly Gly Gly Val Thr Ser
         50                  55                  60
Pro Lys Ala Leu Glu Glu Ala Pro Trp Pro Pro Glu Gly Ala Phe
 65                  70                  75                  80
Val Gly Phe Val Leu Ser Arg Lys Glu Pro Met Trp Ala Asp Leu Leu
                 85                  90                  95
Ala Leu Ala Ala Ala Arg Gly Gly Arg Val His Arg Ala Pro Glu Pro
                100                 105                 110
Tyr Lys Ala Leu Arg Asp Leu Lys Glu Ala Arg Gly Leu Leu Ala Lys
            115                 120                 125
Asp Leu Ser Val Leu Ala Leu Arg Glu Gly Leu Gly Leu Pro Pro Gly
        130                 135                 140
Asp Asp Pro Met Leu Leu Ala Tyr Leu Leu Asp Pro Ser Asn Thr Thr
145                 150                 155                 160
Pro Glu Gly Val Ala Arg Arg Tyr Gly Gly Glu Trp Thr Glu Glu Ala
                165                 170                 175
Gly Glu Arg Ala Ala Leu Ser Glu Arg Leu Phe Ala Asn Leu Trp Gly
            180                 185                 190
```

```
Arg Leu Glu Gly Glu Arg Leu Leu Trp Leu Tyr Arg Glu Val Glu
            195                 200                 205

Arg Pro Leu Ser Ala Val Leu Ala His Met Glu Ala Thr Gly Val Arg
        210                 215                 220

Leu Asp Val Ala Tyr Leu Arg Ala Leu Ser Leu Glu Val Ala Glu Glu
225                 230                 235                 240

Ile Ala Arg Leu Glu Ala Glu Val Phe Arg Leu Ala Gly His Pro Phe
                245                 250                 255

Asn Leu Asn Ser Arg Asp Gln Leu Glu Arg Val Leu Phe Asp Glu Leu
            260                 265                 270

Gly Leu Pro Ala Ile Gly Lys Thr Glu Lys Thr Gly Lys Arg Ser Thr
        275                 280                 285

Ser Ala Ala Val Leu Glu Ala Leu Arg Glu Ala His Pro Ile Val Glu
    290                 295                 300

Lys Ile Leu Gln Tyr Arg Glu Leu Thr Lys Leu Lys Ser Thr Tyr Ile
305                 310                 315                 320

Asp Pro Leu Pro Asp Leu Ile His Pro Arg Thr Gly Arg Leu His Thr
                325                 330                 335

Arg Phe Asn Gln Thr Ala Thr Ala Thr Gly Arg Leu Ser Ser Ser Asp
            340                 345                 350

Pro Asn Leu Gln Asn Ile Pro Val Arg Thr Pro Leu Gly Gln Arg Ile
        355                 360                 365

Arg Arg Ala Phe Ile Ala Glu Glu Gly Trp Leu Leu Val Ala Leu Asp
    370                 375                 380

Tyr Ser Gln Ile Glu Leu Arg Val Leu Ala His Leu Ser Gly Asp Glu
385                 390                 395                 400

Asn Leu Ile Arg Val Phe Gln Glu Gly Arg Asp Ile His Thr Glu Thr
                405                 410                 415

Ala Ser Trp Met Phe Gly Val Pro Arg Glu Ala Val Asp Pro Leu Met
            420                 425                 430

Arg Arg Ala Ala Lys Thr Ile Asn Phe Gly Val Leu Tyr Gly Met Ser
        435                 440                 445

Ala His Arg Leu Ser Gln Glu Leu Ala Ile Pro Tyr Glu Glu Ala Gln
    450                 455                 460

Ala Phe Ile Glu Arg Tyr Phe Gln Ser Phe Pro Lys Val Arg Ala Trp
465                 470                 475                 480

Ile Glu Lys Thr Leu Glu Glu Gly Arg Arg Gly Tyr Val Glu Thr
                485                 490                 495

Leu Phe Gly Arg Arg Arg Tyr Val Pro Asp Leu Glu Ala Arg Val Lys
            500                 505                 510

Ser Val Arg Glu Ala Ala Glu Arg Met Ala Phe Asn Met Pro Val Gln
        515                 520                 525

Gly Thr Ala Ala Asp Leu Met Lys Leu Ala Met Val Lys Leu Phe Pro
    530                 535                 540

Arg Leu Glu Glu Met Gly Ala Arg Met Leu Leu Gln Val His Asp Glu
545                 550                 555                 560

Leu Val Leu Glu Ala Pro Lys Glu Arg Ala Glu Ala Val Ala Arg Leu
                565                 570                 575

Ala Lys Glu Val Met Glu Gly Val Tyr Pro Leu Ala Val Pro Leu Glu
            580                 585                 590

Val Glu Val Gly Ile Gly Glu Asp Trp Leu Ser Ala Lys Glu
        595                 600                 605
```

<210> SEQ ID NO 42
<211> LENGTH: 1878
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
atgggccatc atcatcatca tcatcatcat catcacagca gcggccatat cgaaggtcgt    60
catatgccga agaaggagaa gattaagttc ttcgacctgg tcgccaagaa gtactacgag   120
actgacaact acgaagtcga gattaaggag actaagcgcg gcaagtttcg cttcgccaaa   180
gccaagagcc cgtacaccgg caagatcttc tatcgcgtgc tgggcaaagc cggcggcggt   240
gtcactagtc ccaaggccct ggaggaggcc cctggcccc gccggaagg ggccttcgtg    300
ggctttgtgc tttcccgcaa ggagcccatg tgggccgatc ttctggccct ggccgccgcc   360
agggggggcc gggtccaccg gccccccgag ccttataaag ccctcaggga cctgaaggag   420
gcgcggggc ttctcgccaa agacctgagc gttctggccc tgaggaagg ccttggcctc    480
ccgcccggcg acgacccat gctcctcgcc tacctcctgg accccttccaa caccaccccc   540
gagggggtgg cccggcgcta cggcgggag tggacggagg aggcggggga gcggccgcc    600
ctttccgaga ggctcttcgc caacctgtgg gggaggcttg aggggagga gaggctcctt   660
tggctttacc gggaggtgga gaggcccctt tccgctgtcc tggcccacat ggaggccacg   720
ggggtgcgcc tggacgtggc ctatctcagg gccttgtccc tggaggtggc cgaggagatc   780
gcccgcctcg aggccgaggt cttccgcctg gccggccacc ccttcaacct caactcccgg   840
gaccagctgg aaagggtcct ctttgacgag ctagggcttc cgccatcgg caagacggag   900
aagaccggca gcgctccac cagcgccgcc gtcctggagg ccctccgcga ggcccacccc   960
atcgtggaga agatcctgca gtaccgggag ctcaccaagc tgaagagcac ctacattgac  1020
cccttgccgg acctcatcca ccccaggacg ggccgcctcc acacccgctt caaccagacg  1080
gccacggcca cgggcaggct aagtagctcc gatcccaacc tccagaacat ccccgtccgc  1140
accccgcttg gcagaggat ccgccgggcc ttcatcgccg aggaggggtg gctattggtg   1200
gccctggact atagccagat agagctcagg gtgctggccc acctctccgg cgacgagaac  1260
ctgatccggg tcttccagga ggggcgggac atccacacgg agaccgccag ctggatgttc  1320
ggcgtccccc gggaggccgt ggaccccctg atgcgccggg cggccaagac catcaacttc  1380
ggggtcctct acggcatgtc ggcccaccgc ctctcccagg agctagccat cccttacgag  1440
gaggcccagg ccttcattga gcgctacttt cagagcttcc ccaaggtgcg ggcctggatt  1500
gagaagaccc tggaggaggg caggaggcgg gggtacgtgg agaccctctt cggccgccgc  1560
cgctacgtgc cagacctaga ggcccgggtg aagagcgtgc gggaggcggc cgagcgcatg  1620
gccttcaaca tgcccgtcca gggcaccgcc gccgacctca tgaagctggc tatggtgaag  1680
ctcttcccca ggctggagga aatgggggcc aggatgctcc ttcaggtcca cgacgagctg  1740
gtcctcgagg ccccaaaaga gagggcggag gccgtggccc ggctggccaa ggaggtcatg  1800
gagggggtgt atcccctggc cgtgcccctg gaggtggagg tggggatagg ggaggactgg  1860
ctctccgcca aggagtga                                                1878
```

<210> SEQ ID NO 43
<211> LENGTH: 625
<212> TYPE: PRT
<213> ORGANISM: Artificial Sequence
<220> FEATURE:
<223> OTHER INFORMATION: Description of Artificial Sequence: Synthetic fusion protein

<400> SEQUENCE: 43

```
Met Gly His His His His His His His His Ser Ser Gly His
1               5                   10                  15

Ile Glu Gly Arg His Met Pro Lys Lys Glu Lys Ile Lys Phe Phe Asp
                20                  25                  30

Leu Val Ala Lys Lys Tyr Tyr Glu Thr Asp Asn Tyr Glu Val Glu Ile
                35                  40                  45

Lys Glu Thr Lys Arg Gly Lys Phe Arg Phe Ala Lys Ala Lys Ser Pro
    50                  55                  60

Tyr Thr Gly Lys Ile Phe Tyr Arg Val Leu Gly Lys Ala Gly Gly Gly
65                  70                  75                  80

Val Thr Ser Pro Lys Ala Leu Glu Glu Ala Pro Trp Pro Pro Pro Glu
                85                  90                  95

Gly Ala Phe Val Gly Phe Val Leu Ser Arg Lys Glu Pro Met Trp Ala
                100                 105                 110

Asp Leu Leu Ala Leu Ala Ala Arg Gly Gly Arg Val His Arg Ala
        115                 120                 125

Pro Glu Pro Tyr Lys Ala Leu Arg Asp Leu Lys Glu Ala Arg Gly Leu
    130                 135                 140

Leu Ala Lys Asp Leu Ser Val Leu Ala Leu Arg Glu Gly Leu Gly Leu
145                 150                 155                 160

Pro Pro Gly Asp Asp Pro Met Leu Leu Ala Tyr Leu Leu Asp Pro Ser
                165                 170                 175

Asn Thr Thr Pro Glu Gly Val Ala Arg Arg Tyr Gly Gly Glu Trp Thr
                180                 185                 190

Glu Glu Ala Gly Glu Arg Ala Ala Leu Ser Glu Arg Leu Phe Ala Asn
            195                 200                 205

Leu Trp Gly Arg Leu Glu Gly Glu Glu Arg Leu Leu Trp Leu Tyr Arg
            210                 215                 220

Glu Val Glu Arg Pro Leu Ser Ala Val Leu Ala His Met Glu Ala Thr
225                 230                 235                 240

Gly Val Arg Leu Asp Val Ala Tyr Leu Arg Ala Leu Ser Leu Glu Val
                245                 250                 255

Ala Glu Glu Ile Ala Arg Leu Glu Ala Glu Val Phe Arg Leu Ala Gly
                260                 265                 270

His Pro Phe Asn Leu Asn Ser Arg Asp Gln Leu Glu Arg Val Leu Phe
            275                 280                 285

Asp Glu Leu Gly Leu Pro Ala Ile Gly Lys Thr Glu Lys Thr Gly Lys
            290                 295                 300

Arg Ser Thr Ser Ala Ala Val Leu Glu Ala Leu Arg Glu Ala His Pro
305                 310                 315                 320

Ile Val Glu Lys Ile Leu Gln Tyr Arg Glu Leu Thr Lys Leu Lys Ser
                325                 330                 335

Thr Tyr Ile Asp Pro Leu Pro Asp Leu Ile His Pro Arg Thr Gly Arg
                340                 345                 350

Leu His Thr Arg Phe Asn Gln Thr Ala Thr Ala Thr Gly Arg Leu Ser
            355                 360                 365

Ser Ser Asp Pro Asn Leu Gln Asn Ile Pro Val Arg Thr Pro Leu Gly
370                 375                 380

Gln Arg Ile Arg Arg Ala Phe Ile Ala Glu Glu Gly Trp Leu Leu Val
```

```
              385                 390                 395                 400
        Ala Leu Asp Tyr Ser Gln Ile Glu Leu Arg Val Leu Ala His Leu Ser
                        405                 410                 415

Gly Asp Glu Asn Leu Ile Arg Val Phe Gln Glu Gly Arg Asp Ile His
                        420                 425                 430

Thr Glu Thr Ala Ser Trp Met Phe Gly Val Pro Arg Glu Ala Val Asp
                        435                 440                 445

Pro Leu Met Arg Arg Ala Ala Lys Thr Ile Asn Phe Gly Val Leu Tyr
                    450                 455                 460

Gly Met Ser Ala His Arg Leu Ser Gln Glu Leu Ala Ile Pro Tyr Glu
        465                 470                 475                 480

Glu Ala Gln Ala Phe Ile Glu Arg Tyr Phe Gln Ser Phe Pro Lys Val
                        485                 490                 495

Arg Ala Trp Ile Glu Lys Thr Leu Glu Glu Gly Arg Arg Arg Gly Tyr
                        500                 505                 510

Val Glu Thr Leu Phe Gly Arg Arg Arg Tyr Val Pro Asp Leu Glu Ala
                        515                 520                 525

Arg Val Lys Ser Val Arg Glu Ala Ala Glu Arg Met Ala Phe Asn Met
                    530                 535                 540

Pro Val Gln Gly Thr Ala Ala Asp Leu Met Lys Leu Ala Met Val Lys
        545                 550                 555                 560

Leu Phe Pro Arg Leu Glu Glu Met Gly Ala Arg Met Leu Leu Gln Val
                        565                 570                 575

His Asp Glu Leu Val Leu Glu Ala Pro Lys Glu Arg Ala Glu Ala Val
                        580                 585                 590

Ala Arg Leu Ala Lys Glu Val Met Glu Gly Val Tyr Pro Leu Ala Val
                    595                 600                 605

Pro Leu Glu Val Glu Val Gly Ile Gly Glu Asp Trp Leu Ser Ala Lys
                    610                 615                 620

Glu
        625

<210> SEQ ID NO 44
<211> LENGTH: 605
<212> TYPE: PRT
<213> ORGANISM: Artificial Sequence
<220> FEATURE:
<223> OTHER INFORMATION: Description of Artificial Sequence: Synthetic
      fusion protein

<400> SEQUENCE: 44

His Met Pro Lys Lys Glu Lys Ile Lys Phe Phe Asp Leu Val Ala Lys
        1                   5                   10                  15

Lys Tyr Tyr Glu Thr Asp Asn Tyr Glu Val Glu Ile Leu Glu Thr Lys
                        20                  25                  30

Arg Gly Lys Phe Arg Phe Ala Lys Ala Lys Ser Pro Tyr Thr Gly Lys
                    35                  40                  45

Ile Phe Tyr Arg Val Leu Gly Lys Ala Gly Gly Val Thr Ser Pro
                50                  55                  60

Lys Ala Leu Glu Glu Ala Pro Trp Pro Pro Glu Gly Ala Phe Val
        65                  70                  75                  80

Gly Phe Val Leu Ser Arg Lys Glu Pro Met Trp Ala Asp Leu Leu Ala
                        85                  90                  95

Leu Ala Ala Ala Arg Gly Gly Arg Val His Arg Ala Pro Glu Pro Tyr
                    100                 105                 110
```

```
Lys Ala Leu Arg Asp Leu Lys Glu Ala Arg Gly Leu Leu Ala Lys Asp
            115                 120                 125

Leu Ser Val Leu Ala Leu Arg Glu Gly Leu Gly Leu Pro Pro Gly Asp
130                 135                 140

Asp Pro Met Leu Leu Ala Tyr Leu Leu Asp Pro Ser Asn Thr Thr Pro
145                 150                 155                 160

Glu Gly Val Ala Arg Arg Tyr Gly Gly Glu Trp Thr Glu Glu Ala Gly
            165                 170                 175

Glu Arg Ala Ala Leu Ser Glu Arg Leu Phe Ala Asn Leu Trp Gly Arg
            180                 185                 190

Leu Glu Gly Glu Glu Arg Leu Leu Trp Leu Tyr Arg Glu Val Glu Arg
            195                 200                 205

Pro Leu Ser Ala Val Leu Ala His Met Glu Ala Thr Gly Val Arg Leu
        210                 215                 220

Asp Val Ala Tyr Leu Arg Ala Leu Ser Leu Glu Val Ala Glu Glu Ile
225                 230                 235                 240

Ala Arg Leu Glu Ala Glu Val Phe Arg Leu Ala Gly His Pro Phe Asn
                245                 250                 255

Leu Asn Ser Arg Asp Gln Leu Glu Arg Val Leu Phe Asp Glu Leu Gly
            260                 265                 270

Leu Pro Ala Ile Gly Lys Thr Glu Lys Thr Gly Lys Arg Ser Thr Ser
        275                 280                 285

Ala Ala Val Leu Glu Ala Leu Arg Glu Ala His Pro Ile Val Glu Lys
        290                 295                 300

Ile Leu Gln Tyr Arg Glu Leu Thr Lys Leu Lys Ser Thr Tyr Ile Asp
305                 310                 315                 320

Pro Leu Pro Asp Leu Ile His Pro Arg Thr Gly Arg Leu His Thr Arg
                325                 330                 335

Phe Asn Gln Thr Ala Thr Ala Thr Gly Arg Leu Ser Ser Ser Asp Pro
            340                 345                 350

Asn Leu Gln Asn Ile Pro Val Arg Thr Pro Leu Gly Gln Arg Ile Arg
            355                 360                 365

Arg Ala Phe Ile Ala Glu Glu Gly Trp Leu Leu Val Ala Leu Asp Tyr
        370                 375                 380

Ser Gln Ile Glu Leu Arg Val Leu Ala His Leu Ser Gly Asp Glu Asn
385                 390                 395                 400

Leu Ile Arg Val Phe Gln Glu Gly Arg Asp Ile His Thr Glu Thr Ala
                405                 410                 415

Ser Trp Met Phe Gly Val Pro Arg Glu Ala Val Asp Pro Leu Met Arg
            420                 425                 430

Arg Ala Ala Lys Thr Ile Asn Phe Gly Val Leu Tyr Gly Met Ser Ala
        435                 440                 445

His Arg Leu Ser Gln Glu Leu Ala Ile Pro Tyr Glu Glu Ala Gln Ala
        450                 455                 460

Phe Ile Glu Arg Tyr Phe Gln Ser Phe Pro Lys Val Arg Ala Trp Ile
465                 470                 475                 480

Glu Lys Thr Leu Glu Glu Gly Arg Arg Arg Gly Tyr Val Glu Thr Leu
                485                 490                 495

Phe Gly Arg Arg Arg Tyr Val Pro Asp Leu Glu Ala Arg Val Lys Ser
            500                 505                 510

Val Arg Glu Ala Ala Glu Arg Met Ala Phe Asn Met Pro Val Gln Gly
        515                 520                 525

Thr Ala Ala Asp Leu Met Lys Leu Ala Met Val Lys Leu Phe Pro Arg
```

```
                530                 535                 540
Leu Glu Glu Met Gly Ala Arg Met Leu Leu Gln Val His Asp Glu Leu
545                 550                 555                 560

Val Leu Glu Ala Pro Lys Glu Arg Ala Glu Ala Val Ala Arg Leu Ala
                565                 570                 575

Lys Glu Val Met Glu Gly Val Tyr Pro Leu Ala Val Pro Leu Glu Val
                580                 585                 590

Glu Val Gly Ile Gly Asp Trp Leu Ser Ala Lys Glu
                595                 600                 605

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggaagtacag ctcagagttc tgcagcaccc ctgc                              34

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gatgcgaaac tgaggctggc tgtactgtct c                                 31

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Lys Gln Lys
  1

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 48

His His His His His His His His His His
  1               5                  10

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49
```

```
Gly Thr Gly Gly Gly Gly
  1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Gly Val Thr Ser
  1               5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Gln Lys Lys
  1

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 52

Ala Lys Ser Pro Tyr Thr Gly
  1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 53

Ser Pro Tyr Thr Gly
  1               5
```